US009598467B2

(12) United States Patent
McCaffrey et al.

(10) Patent No.: US 9,598,467 B2
(45) Date of Patent: *Mar. 21, 2017

(54) RECOMBINANT HCV E2 GLYCOPROTEIN

(71) Applicant: The Macfarlane Burnet Institute for Medical Research and Public Health Limited, Melbourne, Victoria (AU)

(72) Inventors: Kathleen McCaffrey, Utrecht (NL); Heidi Drummer, Glenroy (AU); Pantelis Poumbourios, Williamstown (AU)

(73) Assignee: THE MACFARLANE BURNET INSTITUTE FOR MEDICAL RESEARCH AND PUBLIC HEALTH LIMITED, Melbourne (AU)

( * ) Notice: Subject to any disclaimer, the term of this patent is extended or adjusted under 35 U.S.C. 154(b) by 296 days.

This patent is subject to a terminal disclaimer.

(21) Appl. No.: 13/967,059

(22) Filed: Aug. 14, 2013

(65) Prior Publication Data

US 2014/0120127 A1    May 1, 2014

Related U.S. Application Data

(63) Continuation of application No. 12/438,657, filed as application No. PCT/AU2007/001221 on Aug. 24, 2007, now Pat. No. 8,535,686.

(30) Foreign Application Priority Data

Aug. 25, 2006  (AU) ................. 2006904635
Nov. 1, 2006    (AU) ................. 2006906090
Nov. 10, 2006   (AU) ................. 2006906282

(51) Int. Cl.
*C07K 14/005*    (2006.01)
*A61K 39/12*     (2006.01)
*A61K 39/29*     (2006.01)
*C07K 16/10*     (2006.01)
*A61K 38/00*     (2006.01)
*A61K 39/00*     (2006.01)

(52) U.S. Cl.
CPC ............ *C07K 14/005* (2013.01); *A61K 39/12* (2013.01); *A61K 39/29* (2013.01); *C07K 16/109* (2013.01); *A61K 38/00* (2013.01); *A61K 39/00* (2013.01); *A61K 2039/505* (2013.01); *A61K 2039/545* (2013.01); *A61K 2039/55577* (2013.01); *C07K 2317/34* (2013.01); *C07K 2317/76* (2013.01); *C07K 2319/00* (2013.01); *C12N 2770/24222* (2013.01); *C12N 2770/24234* (2013.01)

(58) Field of Classification Search
CPC ............ C07K 16/109; C07K 14/1833; C07K 2319/00; G01N 2333/186; G01N 33/5767; G01N 2333/162; C07D 403/12; C07D 405/12; C07D 405/14; C07D 409/12; C07D 409/14; C07D 413/12; C07D 413/14; C07D 241/36; C12Q 1/707; C12Q 2600/156; C12N 2770/24211; C12N 2770/24262; C12N 2501/335; A61K 39/12; A61K 39/29; A61K 49/183

See application file for complete search history.

(56) References Cited

U.S. PATENT DOCUMENTS 8,535,686 B2 * 9/2013 McCaffrey et al. ........ 424/228.1
2002/0119495 A1 * 8/2002 Nakano et al. ................ 435/7.1

FOREIGN PATENT DOCUMENTS

| EP | 0 804 584 B1 | 6/2002 |
| WO | WO 00/26418 A1 | 5/2000 |
| WO | WO 01/21807 A1 | 3/2001 |
| WO | WO 02/22155 A1 | 3/2002 |
| WO | WO 03/022880 A2 | 3/2003 |
| WO | WO 2005/067643 A2 | 7/2005 |

OTHER PUBLICATIONS

Kronenberger et al. J. Viral. Hepat. Jul. 11, 2004, (4), pp. 310-318.*
Lin et al. J. Clin. Microbiol. Aug. 2005, vol. 43, No. 8, pp. 3917-3924.*
Yi et al. Virol. 1997, vol. 231, pp. 119-129.*
McCaffrey et al. J. Virol. Sep. 2007, vol. 81, No. 17, pp. 9584-9590.*
Allander et al. Virology, 2000, vol. 277, pp. 358-367.*
Shimizu et al. Virology, 1996, vol. 409-412.*
International Search Report, issued on Oct. 9, 2007, for application No. PCT/AU2007/001221.
McCaffrey et al., "Expression and Characterization of a Minimal Hepatitis C Virus Glycoportein E2 Core Domain That Retains CD81 Binding," *Journal of Virology*, vol. 81, No. 17, pp. 9584-9590 (Sep. 2007).
Lechmann et al., "Vaccine Development for Hepatitis C," *Seminars in Liver Disease*, vol. 20, No. 2, pp. 211-226 (2000).
Forns et al., "Characterization of Modified Hepatitis C Virus E2 Proteins Expressed on the Cell Surface," *Virology*, vol. 274, pp. 75-85 (2000).
Wu et al., "Single Amino Acit Changes Can Influence Titer, Heparin Binding and Tissue Tropism in Different Adeno-Associated Virus Serotypes," Journal of Virology, vol. 80, No. 22, pp. 11393-11397, Nov. 2006.
Supplementary European Search Report issued on Jun. 17, 2010 in application No. EP 07784854.

(Continued)

*Primary Examiner* — Bao Li
(74) *Attorney, Agent, or Firm* — Foley & Lardner LLP

(57) ABSTRACT

The invention provides modified hepatitis C virus (HCV) E2 glycoproteins comprising the HCV-E2 receptor-binding domain (RBD) including the HVR1, HVR2 and igVR variable regions wherein in at least one of said variable regions at least a part of the variable region is replaced with a flexible linker sequence. The invention also provides vaccine compositions comprising the modified glycoproteins as well as methods of use thereof.

17 Claims, 36 Drawing Sheets

(56) References Cited

OTHER PUBLICATIONS

Roccasecca et al., "Binding of Hepatitis C Virus E2 Glycoprotein to CD81 Is Strain Specific and Is Modulated by a Complex Interplay between Hypervariable Regions 1 and 2," *Journal of Virology*, vol. 77, No. 3, pp. 1856-1867, Feb. 2003.

Mondelli et al., "Variability or conservation of hepatitis C virus hypervariable region 1? Implications for immune responses," *J. Biosci.*, vol. 28, No. 3, pp. 305-310, Apr. 2003.

Office Action issued on Mar. 2, 2012 in U.S. Appl. No. 12/436,657 (U.S. Pat. No. 8,535,686).

Office Action issued on Jul. 16, 2012 in U.S. Appl. No. 12/436,657 (U.S. Pat. No. 8,535,686).

Office Action issued on Mar. 20, 2013 in U.S. Appl. No. 12/436,657 (U.S. Pat. No. 8,535,686).

Notice of Allowance issued on May 23, 2013 in U.S. Appl. No. 12/436,657 (U.S. Pat. No. 8,535,686).

Du De Wei et al., "The Fusion Expression and Purification of HCV Envelop Protein E2 and Preparation of its Polyclonal Antibody," *Chinese General Practice*, vol. 8, No. 22, pp. 1834-1836, Nov. 30, 2005.

\* cited by examiner

```
                                                                       AP33
                                                      HVR1            Y   Y
1a._.H77C.AF011751        ETHVTGGNAGRTTAGLVGLLTPGAKQNIQLINTNGSWHINSTALNCNESLNTGWLAGLFY
1b.JP.HCV-N.S62220        HTLTTGGHAAHLTSGFAGLFTPGPSQRIQLINTNGSWHINRTALNCNDSLQTGFLAALSY
4a.EG.ED43.Y11604         ETHVSGAAVGRSTAGLANLFSSGSKQNLQLINSNGSWHINRTALNCNDSLNTGFLASLFY
6a.HK.EUHK2.Y12083        QTMIA-HGVSQTTSGFASLLTPGAKQNIQLINTNGSWHINRTALNCNDSLQTGFLASLFY
3a._.CB.AF046866          VTYTTGGSAAHATRGLTSLFSVGAQQKLQLVNTNGSWHINSTALNCNESINTGFIAGLFY
5a.ZA.SA13.AF064490       NTRTVGGSAAQGARGLASLFTPGPQQNLQLINTNGSWHINRTALNCNDSLQTGFVAGLLY
2a.JP.JFH-1.AB047639      GTTTVGGAVARSTNVIAGVFSHGPQQNIQLINTNGSWHINRTALNCNDSLNTGFLAALFY
                           *    ..: :  :...:: *..*.:***:*.****** ******.*::**:*.* *
                                                      HVR2 Y
1a._.H77C.AF011751        QHKFNSSGCPERLASCRRLTDFAQGWGPISYAN-GSGL-DERPYCWHYPPRPCGIVPAKS
1b.JP.HCV-N.S62220        TYRFNSSGCPGRMASCRSIDKFDQGWGPITYAD-PKDP-DQRPYCWHYAPQQCGIIPRSE
4a.EG.ED43.Y11604         THKFNSSGCSERLACCKSLDSYGQGWGPLGVAN-ISGSSDDRPYCWHYAPRPCGIVPASS
6a.HK.EUHK2.Y12083        THKFNSSGCPERMAACKPLAEFRQGWGQITHKN-VSGPSDDRPYCWHYAPRPCEVVPARS
3a._.CB.AF046866          YHRFNSTGCPQRLSSCKPITFFKQGWGPLTDAN-ISGPSDDKPYCWHYAPRPCKVVPASG
5a.ZA.SA13.AF064490       YHKFNSTGCPQRMASCRPLAAPDQGWGTISYAA-VSGPSDDKPYCWHYPPRPCGIVPARG
2a.JP.JFH-1.AB047639      TNRFNSSGCGRLSACRNIEAFRIGWGTLQYEDNVTNPEDMRPYCWHYPPKPCGVVPARS
                          :***:**. *::.*:  :   ***  :      .. * :******.*: *  ::*

1a._.H77C.AF011751        VCGPVYCFTPSPVVVGTTDRSGAPTYSWGANDTDVFVLNNTRPPLGNWFGCTWMNSTGFT
1b.JP.HCV-N.S62220        ACGPVYCSTPSPVVVGTTDRFGAPTYNWGDNETDVLLLNNTRPPQGNWFGCTWMNSTGFT
4a.EG.ED43.Y11604         VCGPVYCFTPSPVVVGTTDHVGVPTYTWGENETDVFLLNSTRPPHGAWFGCVWMNSTGFT
6a.HK.EUHK2.Y12083        VCGPVYCFTPSPVVVGTTDKRGNPTYTWGENETDVFMLESLRPPTGGWFGCTWMNSTGFT
3a._.CB.AF046866          VCGPVYCFTPSPVVVGTTDAKGVPTYTWGANDTDVFLLESLRPPGGRWFGCTWMNSTGFV
5a.ZA.SA13.AF064490       VCGPVYCFTPSPVVVGTTDRKGNPTYSWGENETDIFLLNNTRPPTGNWFGCTWMNSTGFV
2a.JP.JFH-1.AB047639      VCGPVYCFTPSPVVVGTTDRRGVPTYTWGENETDVFLLNSTRPPQGSWFGCTWMNSTGFT
                          .****** *********** * *** .** *:**:::*:. *** * ****.*******.
                                                   igVR Y
1a._.H77C.AF011751        KVCGAPPCVIGGVG-----NNTLLCPTDCFRKHPEATYSRCGSGPWITPRCMVDYPYRLW
1b.JP.HCV-N.S62220        KTCGAPPCNIGGVG-----NNTLTCPTDCFRKHPEATYSKCGSGPWLTPRCMVDYPYRLW
4a.EG.ED43.Y11604         KTCGAPPCEVNTNN-----GTWHCPTDCFRKHPETTYAKCGSGPWITPRCLIDYPYRLW
6a.HK.EUHK2.Y12083        KTCGAPPCQIVPGNYNS-SANELLCPTDCFRKHPEATYQRCGSGPWVTPRCLVDYAYRLW
3a._.CB.AF046866          KTCGASPCDIYGGGNSGNESDLFCPTDCFRKHPEATYSRCGAGPWLTPRCMVDYPYRLW
5a.ZA.SA13.AF064490       KTCGAPPCNLGPTG-----NNSLKCPTDCFRKHPDATYTKCGSGPWLTPRCLVHYPYRLW
2a.JP.JFH-1.AB047639      KTCGAPPCRTRADFN----ASTDLLCPTDCFRKHPDATYIKCGSGPWLTPKCLVHYPYRLW
                          *.***.**             * :*********:** :**:***:**:*.:.*.****

1a._.H77C.AF011751        HYPCTINYTIFKVRMYVGGVEHRLEAACNWTRGERCDLEDRDRSELSPLLLSTTQWQVLP
1b.JP.HCV-N.S62220        HYPCTVNFSIFKVRMYVGGVEHRLNAACNWTRGERCDLDDRDRSELSPLLLSTTEWQVLP
4a.EG.ED43.Y11604         HFPCTANPSVFNIRTFVGGIEHRMQAACNWTRGEVCGLEHRDRVELSPLLLTTTAWQILP
6a.HK.EUHK2.Y12083        HYPCTVNFTLHKVRMFVGGTEHRFDVACNWTRGERCELHDRNRIEMSPLLFSTTQLSILP
3a._.CB.AF046866          HYPCTVNFTLFKVRMFVGGFEHRFTAACNWTRGERCDIEDRDRSEQHPLLHSTTELAILP
5a.ZA.SA13.AF064490       HYPCTLNYTIPKVRMYIGGLEHRLEVACNWTRGERCDLEDRDRAELSPLLHTTTQWAILP
2a.JP.JFH-1.AB047639      HYPCTVNFTIPKIRMYVGGVEHRLTAACNFTRGDRCDLEDRDRSQLSPLLHSTTEWAILP
                          *:*** *::.::* ::**  ***: .***:***: * :..:* : *** :**    TMD
1a._.H77C.AF011751        CSFTTLPALSTGLIHLHQNIVDVQYLYGVGSSIASWAIKWEYVVLLFLLLADARVCSCLW
1b.JP.HCV-N.S62220        CSFTTLPALSTGLIHLHQNIVDVQYLYGIGSAVVSFAIKWEYVVLLFLLLADARVCACLW
4a.EG.ED43.Y11604         CSFTTLPALSTGLIHLHQNIVDVQYLYGVGSSWALKWEYVVLAPLLLADARVSAYLW
6a.HK.EUHK2.Y12083        CSFSTMPALSTGLIHLHQNIVDVQYLYGVSTNVTSWVVKWEYIVLMFLVLADARICTCLW
3a._.CB.AF046866          CSFTPMPALSTGLIHLHQNIVDVQYLYGVGSGMVGWALKWEFVILIFLLLADRRVCVALW
5a.ZA.SA13.AF064490       CSFTPTPALSTGLIHLHQNIVDTQYLYGLSSSIVSWAVKWEYIVLAFLLLADARICTCLW
2a.JP.JFH-1.AB047639      CTYSDLPALSTGLLHLHQNIVDVQYMYGLSPAITKYVVRWEWVVLLFLLLADARVCACLW
                          *:::  *******:*********.**:** .          .:::**:::* **:*** *:.  **

1a._.H77C.AF011751        MMLLISQAEA
1b.JP.HCV-N.S62220        MMLLIARAEA
4a.EG.ED43.Y11604         MMFMVSQVEA
6a.HK.EUHK2.Y12083        LMLLISTVEA
3a._.CB.AF046866          LMLMITQAEA
5a.ZA.SA13.AF064490       IMLLVCQAEA
2a.JP.JFH-1.AB047639      MLILLGQAEA
                          :::: .**
```

Figure 2

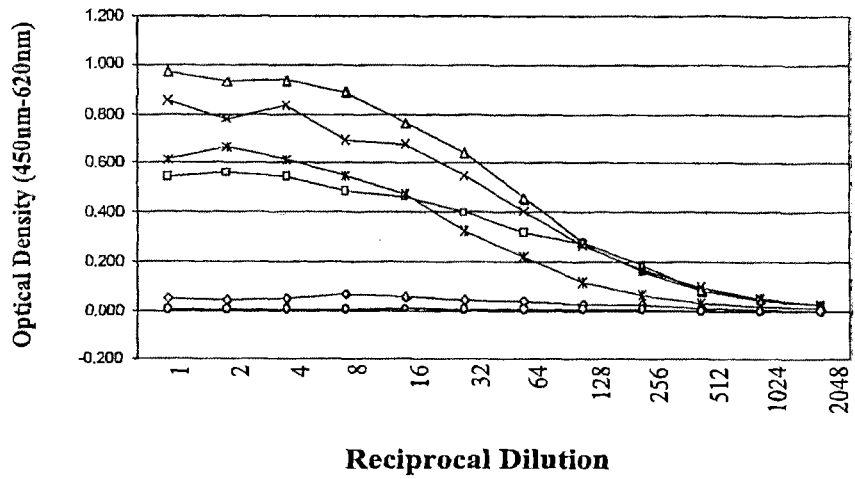
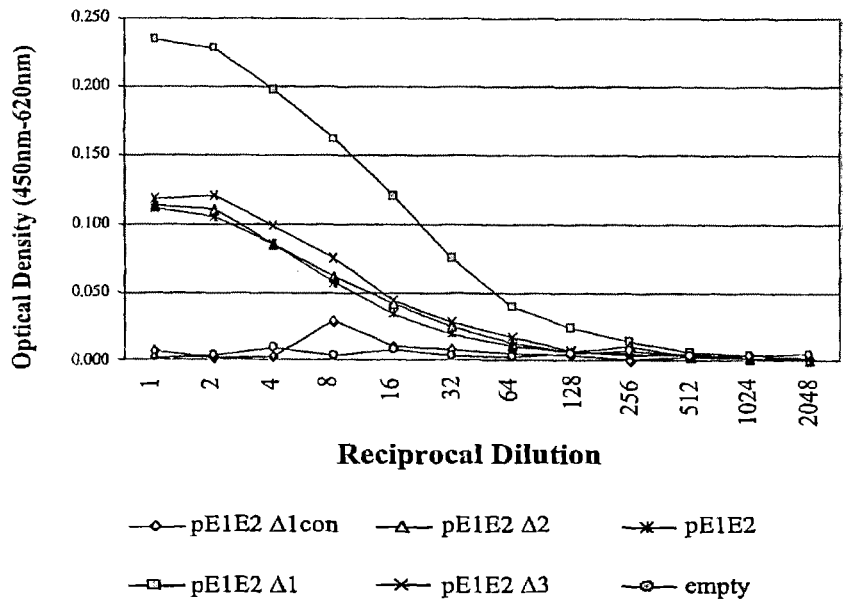
Figure 5.

A.
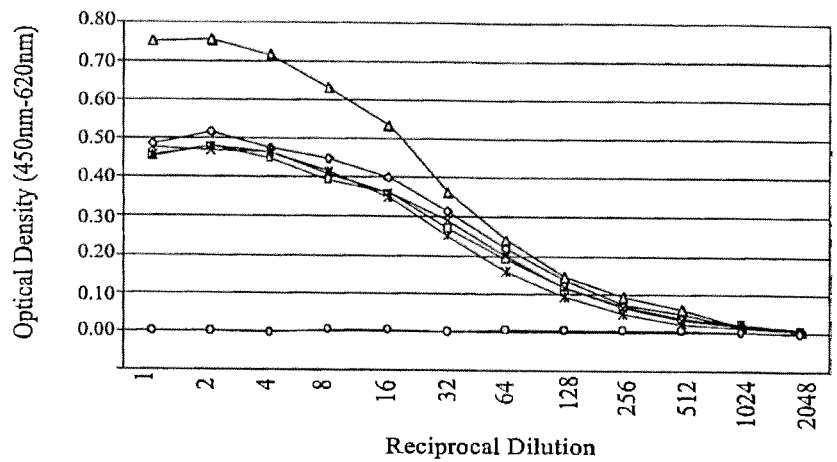
B.
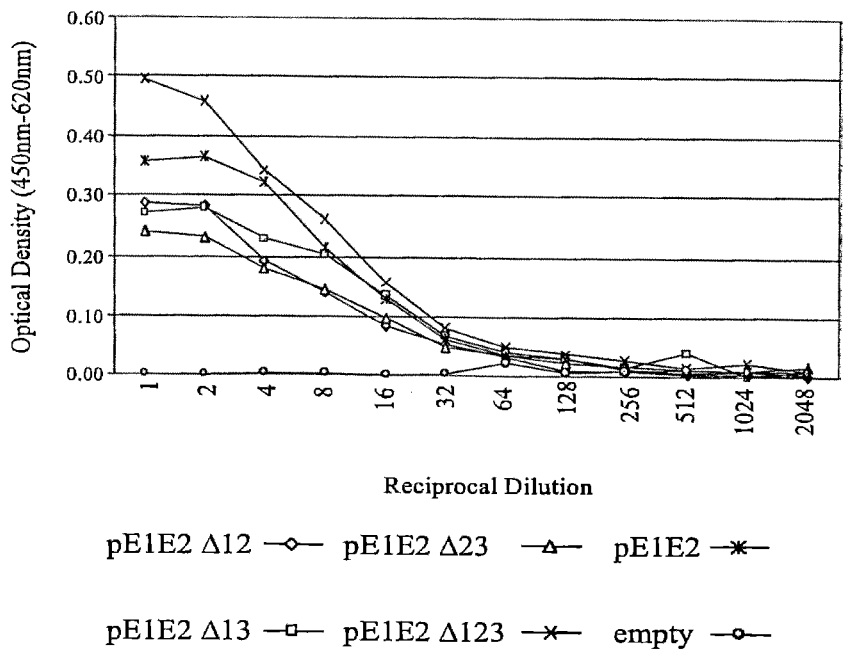
Figure 13.

A.
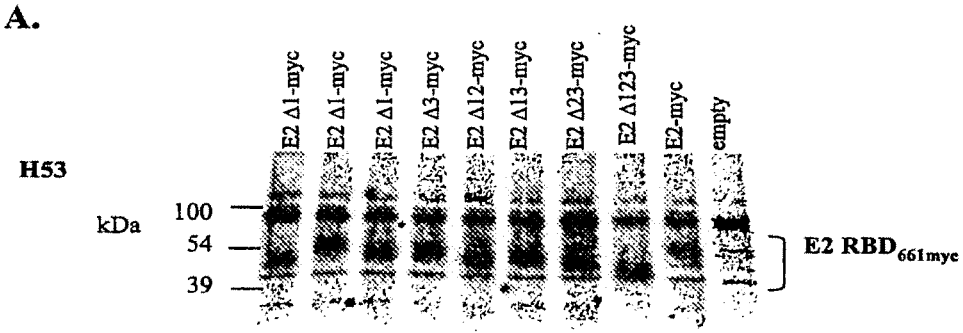
B.
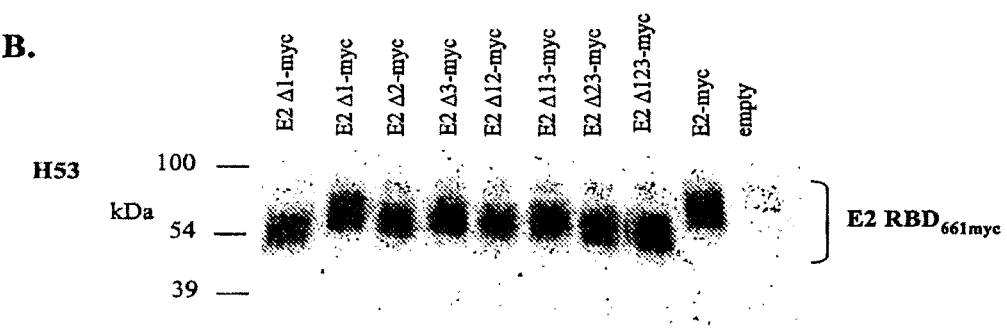
Figure 14.

A.
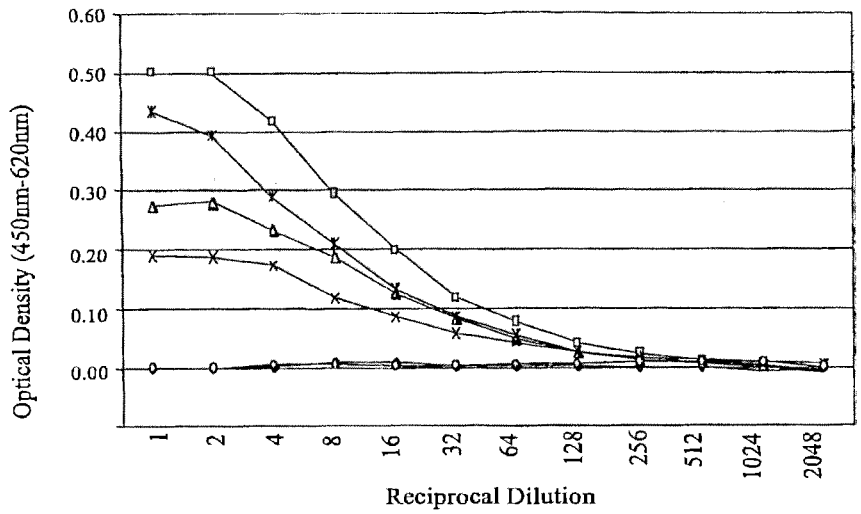
B.
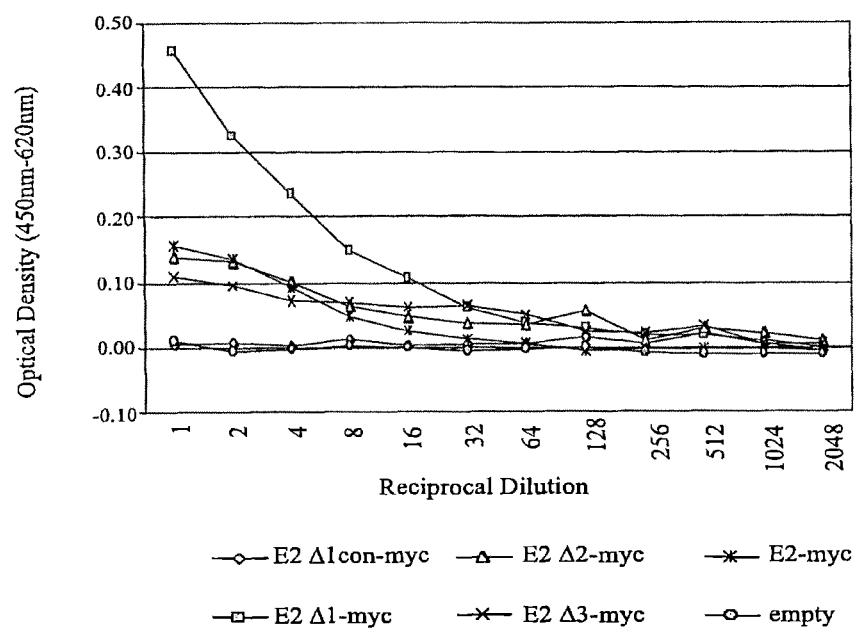
Figure 15.

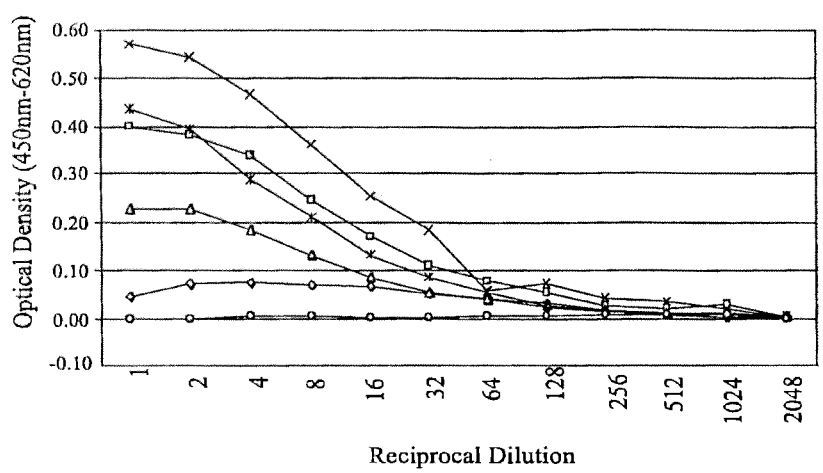
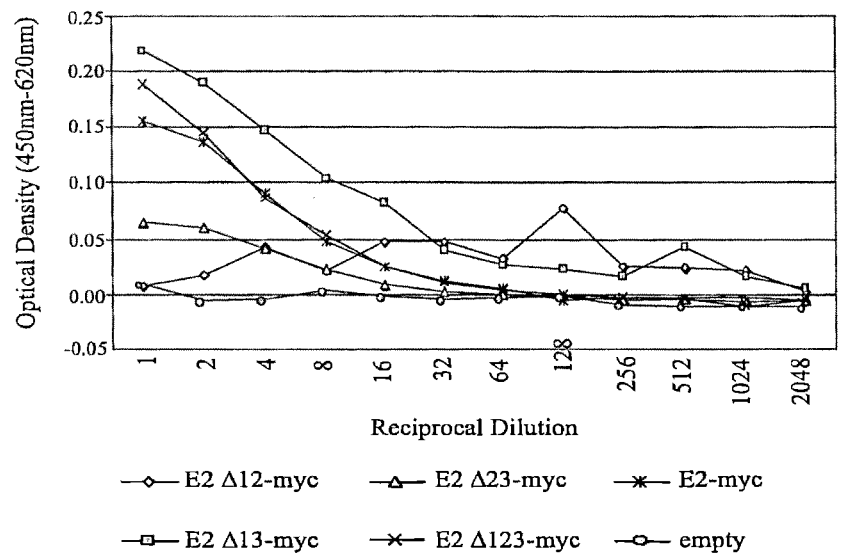
Figure 16.

Lane:

| Lane | Protein | Lane | Protein |
|---|---|---|---|
| 1. | E2-his | 5. | E2Δ13-his |
| 2. | E2Δ1-his | 6. | E2Δ2-his |
| 3. | E2Δ12-his | 7. | E2Δ23-his |
| 4. | E2Δ123-his | 8. | E2Δ3-his |

A.
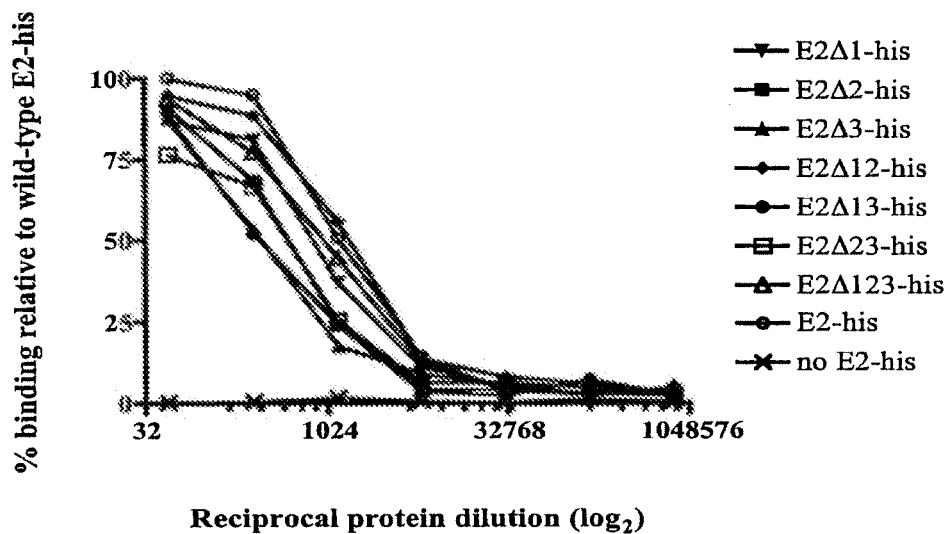
B.
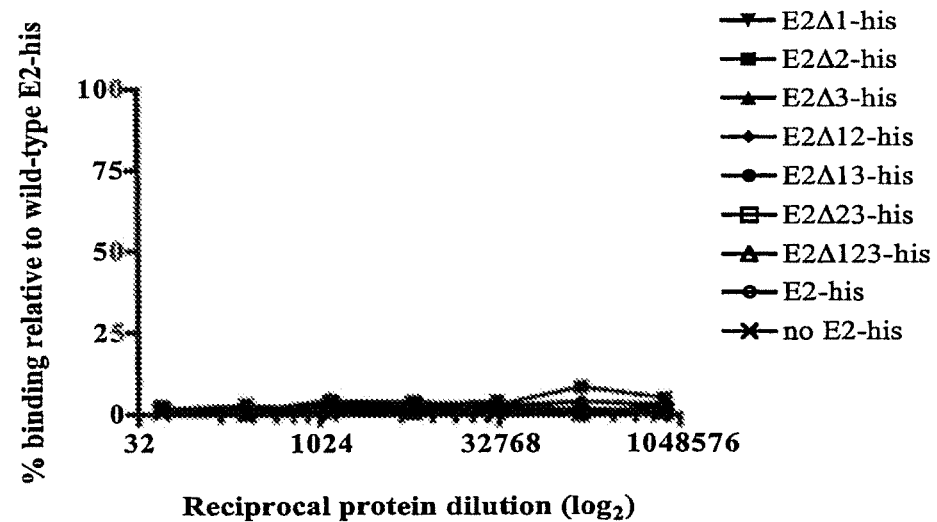
Figure 30

Figure 31

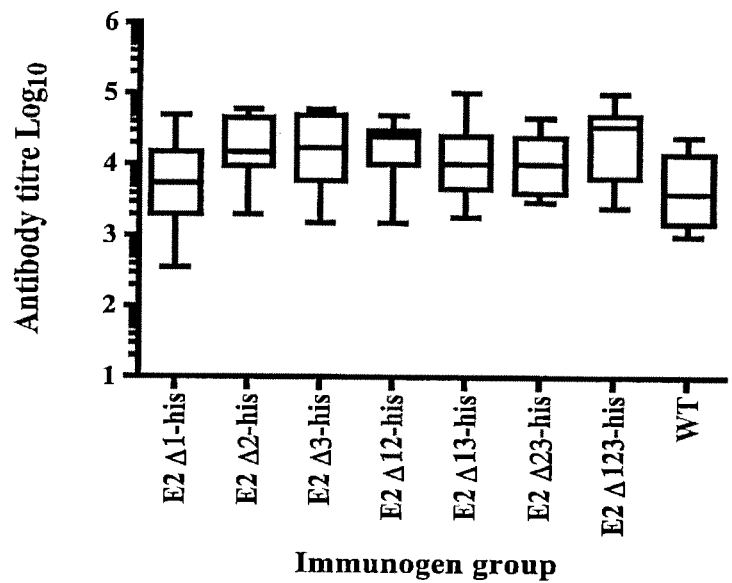
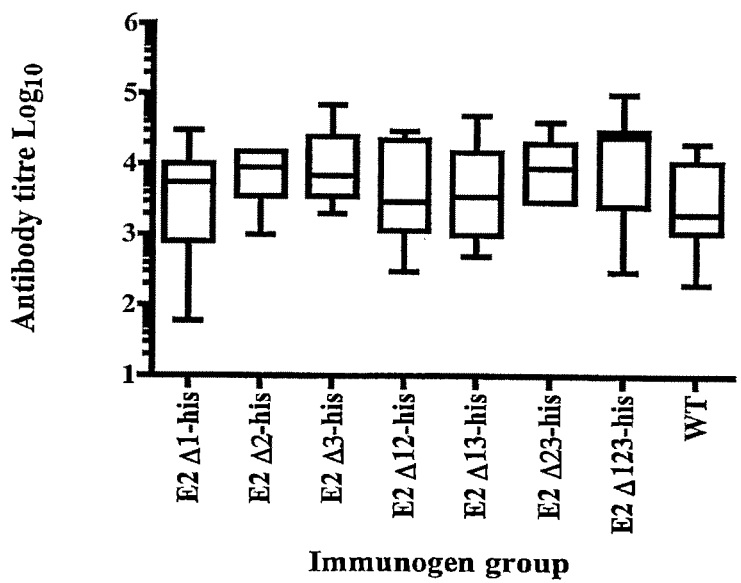
Figure 35

RECOMBINANT HCV E2 GLYCOPROTEIN

FIELD OF INVENTION

The present invention relates to a new and improved treatment for viral hepatitis C (HCV) infection. The present invention particularly relates to vaccine compositions for prevention and therapeutic treatment of HCV infection based on administering a recombinant HCV polyprotein.

BACKGROUND OF THE INVENTION

According to the World Health Organisation, hepatitis C virus (HCV) infects approximately 170 million to 200 million people worldwide. While governments have increased education about how HCV is transmitted, and despite prevention programs, HCV continues to proliferate. Approximately 80% of those who are infected with HCV remain carriers of the virus. In Australia about 16,000 new cases of HCV infection are reported each year, the new infections being most prevalent amongst injection drug users. HCV is the most common blood-borne viral infection, causing the death of a substantial proportion of the population.

HCV is known to infect the liver and certain immune cells of a sufferer. As a result, HCV leads to serious liver disease such as fibrosis, cirrhosis, steatosis and heptocellular carcinoma (liver cancer) more frequently than other forms of hepatitis. HCV is a leading cause for the requirement of liver transplants. It is generally believed that the acute phase of the infection is often unrecognised due to the sub-clinical nature of the infection, and 80% of individuals progress to a chronic condition. Chronic infection is a result of the immune system's failure to generate an adequate immune response against the virus.

Currently there is no vaccine for HCV and the only available therapy for treatment of HCV has relied on development of antiviral drugs and drug combinations. The general idea behind antiviral drug design is to identify viral proteins, or parts of proteins, that can be disabled or inhibited. A standard treatment of choice for patients suffering moderate or severe fibrosis includes a combination of alpha-interferon and ribavirin. The antiviral effects of combination alpha-interferon and ribavirin therapy cause a rapid decrease in HCV levels in the blood, even after a single dose. Conventional alpha-interferon treatment for HCV however suffers several drawbacks. For example, (i) when alpha-interferon treatment is stopped after a few weeks or months of treatment, the viral load level is known to re-establish rapidly; (ii) treatment with alpha-interferon/ribavirin is associated with severe side effects, including flu-like symptoms, reduced red or white cell counts, bone marrow suppression, neuropsychiatric effects, particularly depression and anemia; (iii) effective treatment requires patient adherence to a frequent dosing regimen since alpha-interferon is absorbed and eliminated from the body rapidly; and (v) high cost of such treatments.

Some of the above drawbacks, referring particularly to item (iii) above, have been addressed by subjecting alpha-interferon to 'pegylation' in which polyethylene glycol molecules are attached to the interferon. The administration of pegylated interferon in combination with ribavirin increases the half-life of interferon and has the advantage of decreasing the frequency of dosing, hence patient compliance. Such treatment however has proven to be efficacious in less than 50% of treated patients. Given the increasing number of chronic sufferers of HCV, there is a need to develop a vaccine for both prophylactic and therapeutic purposes.

Development of a successful vaccine to protect against HCV infection has been elusive. One proposed reason for this difficulty is that HCV, being an RNA virus, is genetically unstable allowing it to achieve a high rate of viral mutation to evade the body's immune response. It is therefore a challenge for researchers to identify a portion of the virus that is conserved.

HCV has been classified in a separate genus (Hepacivirus) of the Flaviviridae family. HCV is non-cytopathic and rather triggers an immune response that either rapidly clears the infection or initiates an inflammatory response leading to chronic infection and liver injury. Spontaneously resolving infections that permanently clear HCV RNA without treatment occur in ~30% of acute cases suggesting a natural immunity to HCV and is thus encouraging for the prospect of vaccine development. However, the determinants for this outcome of HCV infection are unknown.

The HCV virion contains a positive-sense single stranded RNA genome of about 9.5 kb. The genome encodes a single polyprotein of 3,010 to 3,030 amino acids. The structural proteins comprise a core protein forming the viral nucleocapsid and two envelope glycoproteins, E1 and E2. Some recent efforts towards the development of a HCV vaccine have focused on HCV envelope glycoproteins E1 and E2. It has been found that E1 and E2 form non-covalently associated heterodimers on the surface of the virion that mediate both viral attachment and entry and thus present targets for the host immune response.

Recent studies have suggested that envelope glycoprotein E2 binds to CD81 on the surface of CD4+ T cells. During the binding process, E2 undergoes rapid conformational change. To date no research has been able to provide a suitable modified envelope glycoprotein, which can exhibit "wild-type" levels of CD81 binding.

Throughout this specification, including the claims, all numbering of polypeptide residues of the HCV envelope glycoproteins E1 and E2 is based on the prototype HCV-H77 polyprotein sequence, Genbank Accession No. AF 009606. The mature form of glycoprotein E1 is encompassed by polyprotein residues 191 and 383, and the mature form of glycoprotein E2 is encompassed by polyprotein residues 384 and 746.

The receptor-binding domain (RBD) of E2 is encompassed by polyprotein residues 384-661 ($E2_{661}$). Recombinant forms of $E2_{661}$ RBD are efficiently secreted from transfected cells and are able to interact with CD81 and other cell surface molecules. The E2 RBD contains two variable regions, HVR1 (384-410) and HVR2 (474-482).

Variable region 1, located at the N-terminus of E2, is the most variable region in the HCV genome, is highly immunogenic and rapidly accumulates neutralization escape mutations. Despite the high level of amino acid variability in HVR1, there is an overall conservation of basic residues that are important for viral entry.

Variable region 2 is located within the region flanked by Cys-459 to Cys-486. Although originally described as a 7-residue sequence, comparison of E2 sequences from different HCV genotypes suggests it may extend from residues 461-481. In comparison to HVR1, the sequence of HVR2 is relatively stable within HCV infected people, although an accumulation of mutations at this location has been shown to correlate with responsiveness to interferon-α treatment.

In work leading to the present invention, the inventors have observed that alignment of E2 sequences representing the six major genotypes of HCV reveals a previously undescribed variable region between polyprotein residues 570-580 that is relatively conserved within a genotype but varies across genotypes due to amino acid insertions and deletions. Accordingly, amino acids 570-580 have been denoted the intergenotypic variable region (igVR). Examination of the corresponding region from all 6 genotypes of HCV, and divergent isolates therein, show that igVR is also flanked by conserved cysteine residues (Cys-569 and Cys-581), suggesting that these sequences form disulfide-constrained loops.

To date no vaccine treatment for HCV using the adaptive immune response route has been successful. Given the drawbacks of current and experimental therapies for treatment of HCV, there is an unmet need for providing a cell-mediated immune response to treat HCV infection.

It is one object of the present invention to provide an immunotherapeutic approach to prevent or treat HCV infection. A further object of the present invention is to provide an immunotherapeutic approach to prevent or treat HCV infection. A further object of the present invention is to provide a modified E2 glycoprotein, which approaches 'wild-type' binding levels to natural cellular receptors of HCV infection.

International Patent Publication No. WO 02/22155 (Hawaii Biotechnology Group, Inc.) discloses a truncated HCV E2 polypeptide which lacks the HVR1 region and is capable of secretion into growth medium when expressed in recombinant form in a host cell. The polypeptide may also lack its C-terminus after residue 662. International Patent Publication No. WO 03/022880 (XTL Biopharmaceuticals Ltd.) also discloses a truncated version of the E2 protein lacking HVR1 region.

The foregoing discussion is intended to introduce the field of the present invention and should not be construed in any way an admission of the state of common general knowledge in this art. Bibliographic details of publications referred to in this specification are set out at the end of the description. The reference to any prior art document in the specification is not, and should not be taken as, an acknowledgement or any form of suggestion that the document forms part of the common general knowledge.

SUMMARY OF THE INVENTION

Throughout this specification and the claims which follow, unless the context requires otherwise, the word "comprise", and or variations such as "comprises" or "comprising", will be understood to imply the inclusion of a stated integer or step or group of integers or steps but not the exclusion of any other integer or step or group of integers or steps.

In one aspect, the present invention provides a modified hepatitis C virus (HCV) E2 glycoprotein comprising the HCV-E2 receptor-binding domain (RBD) including the HVR1, HVR2 and igVR variable regions, wherein in at least one of said variable regions at least a part of the variable region is replaced with a flexible linker sequence.

In another aspect, the present invention provides a modified hepatitis C virus (HCV) E2 glycoprotein comprising the HCV-E2 receptor-binding domain (RBD) including the HVR1, HVR2 and igVR variable regions, wherein at least a part of the HVR2 variable region is removed or is replaced with a flexible linker sequence.

In yet another aspect, the present invention provides a modified hepatitis C virus (HCV) E2 glycoprotein comprising the HCV-E2 receptor-binding domain (RBD) including the HVR1, HVR2 and igVR variable regions, wherein at least a part of the igVR variable region is removed or is replaced with a flexible linker sequence.

The modified HCV E2 glycoproteins as broadly described above are glycoproteins which substantially approach HCV virion wild-type conformation, and retain the ability to bind to the HCV receptor CD81 and conformation-dependent antibodies.

The present invention also provides a composition comprising a modified HCV E2 glycoprotein as broadly described above, together with a pharmaceutically acceptable carrier or diluent.

Such a composition may be formulated as a vaccine composition, preferably including an adjuvant.

In yet another aspect, the present invention also provides a method of eliciting an immune response in a patient, which comprises administration to the patient of an effective amount of a modified HCV E2 glycoprotein as broadly described above.

In this aspect, the invention includes a method for prophylactic or therapeutic treatment of HCV infection in a patient, which comprises administration to the patient of an effective amount of a modified HCV E2 glycoprotein as broadly described above.

In a further aspect, this invention provides the use of a modified HCV E2 glycoprotein as broadly described above in, or in the manufacture of a medicament for, eliciting an immune response in a patient.

In this further aspect, this invention includes the use of a modified HCV E2 glycoprotein as broadly described above in, or in the manufacture of a medicament for, prophylactic or therapeutic treatment of HCV infection in a patient.

In yet a further aspect, this invention provides an agent for eliciting an immune response in a patient, which comprises a modified HCV E2 glycoprotein as broadly described above.

In this further aspect, the invention includes an agent for prophylactic or therapeutic treatment of HCV infection in a patient, which comprises a modified HCV E2 glycoprotein as broadly described above.

The present invention also provides an isolated antibody raised against a modified HCV E2 glycoprotein as broadly described above. The antibody may be monoclonal or polyclonal.

In this aspect, the invention also provides a method for prophylactic or therapeutic treatment of HCV infection in a patient, which comprises administration to the patient of an effective amount of an antibody as described above.

The invention also provides the use of an antibody as described above in, or in the manufacture of a medicament for, prophylactic or therapeutic treatment of HCV infection in a patient.

In this aspect also, the invention provides an agent for prophylactic or therapeutic treatment of HCV infection in a patient, which comprises an antibody as described above.

Further, the invention provides a method of detecting HCV infection in a patient, comprising contacting a biological sample from the patient with an antibody as described above under conditions which allow formation of an antibody-antigen complex, and detecting said complex, wherein formation of said complex is indicative of the presence of HCV in the sample.

BRIEF DESCRIPTION OF THE DRAWINGS

FIG. 2 shows a ClustalX alignment of diverse HCV E2 glycoprotein sequences from genotypes 1-6. The two recognized hypervariable regions, HVR1 and HVR2, and the novel variable region igVR are highlighted (grey). The conserved cysteine residues that flank the HVR2 and igVR regions, as well as the first conserved cysteine residue proposed to anchor the N-terminal region to the rest of the E2 glycoprotein, are also indicated (bold type). The positions of the CD81-binding determinants (boxed) and the epitope for the broadly neutralizing antibody AP33 are indicated. N-linked glycosylation sites associated with variable regions are also shown (tree). Predicted transmembrane domain is underlined.

FIG. 5 shows the ability of HCV E1E2 containing single variable region deletions to bind CD81-LEL. A. Ability of intracellular forms of E2 to bind to CD81-LEL. Metabolically-labelled cell lysates of 293T cells transfected with wild-type (pE1E2), pE1E2 with a deletion of a variable region, or empty vector were applied to CD81 MBP-LEL (residues 113-201) coated enzyme immunoassay plates at progressive two-fold dilutions. Bound E2 was detected using anti-E2 conformation-dependent antibody H53 and rabbit anti-mouse horseradish peroxidase (HRP) conjugate. Absorbance values (optical density) were read at 450 nm and the 620 nm background subtracted. B. Virion-incorporated E2 glycoprotein binding to CD81-LEL. Lysates of metabolically-labelled HCV glycoprotein-pseudotyped HIV-1 particles were applied to CD81 MBP-LEL (residues 113-201) coated enzyme immunoassay plates at progressive two-fold dilutions. Bound E2 was detected as described for A. Data is representative of two independent experiments.

FIG. 13 shows the ability of E2 containing multiple variable region deletions to bind to CD81-LEL. A. Metabolically-labelled cell lysates of 293T cells transfected with wild-type (pE1E2), pE1E2 containing multiple variable region deletions, or empty (pCDNA4) vector were applied to CD81 MBP-LEL (residues 113-201) coated enzyme immunoassay plates at progressive two-fold dilutions. Bound E2 was detected using anti-E2 conformation-dependent monoclonal antibody H53 and rabbit anti-mouse horseradish peroxidase (HRP) conjugate. Absorbance values were read at 450 nm-620 nm (background). B. Ability of virion-incorporated forms of E2 containing multiple variable region deletions to bind CD81-LEL. Lysates of metabolically-labelled E1E2-pseudotyped HIV-1 particles were applied to CD81 MBP-LEL (residues 113-201) coated enzyme immunoassay plates at progressive two-fold dilutions. Bound E2 was detected as described above. Absorbance values were read at 450 nm-620 nm (background). Data is representative of two independent experiments.

FIG. 14 shows the expression of E2 RBD (residues 384-661) containing single and multiple variable region deletions in cell lysates. A. Metabolically labelled cell lysates of 293T cells transfected with either wild-type (E2-myc), E2-myc containing single or multiple variable region deletions, or empty vector were immunoprecipitated with anti-E2 conformation-dependent antibody H53. B. Secretion of E2 RBD (residues 384-661) containing single and multiple variable region deletions in supernatant fluid. The supernatant fluid from metabolically-labelled 293T cells transfected with either wild-type (E2-myc), E2-myc containing single or multiple variable region deletions, or empty vector were immunoprecipitated with the anti-E2 conformation dependent antibody, H53. All samples were separated on 10-15% SDS-PAGE gradient gels and visualized using a phosphoimager. Data for the single variable region deletion is from one experiment.

FIG. 15 shows the ability of E2 RBD (residues 384-661) containing single variable region deletions to bind CD81-LEL. A. Cell lysates from metabolically-labelled 293T cells transfected with wild-type (E2-myc), E2-myc containing single variable region deletions, or empty vector were applied to CD81 MBP-LEL (residues 113-201) coated enzyme immunoassay plates at progressive two-fold dilutions. Bound E2 was detected using anti-E2 conformation-dependent antibody H53 and rabbit anti-mouse horseradish peroxidase (HRP) conjugate. Absorbance values were read at 450 nm-620 nm (background). B. Ability of secreted E2 RBD (residues 384-661) containing single variable region deletions to bind CD81-LEL. Tissue-culture fluid from metabolically-labelled 293T cells transfected with wild-type (E2-myc), E2-myc containing single variable region deletions were applied to CD81 MBP-LEL (residues 113-201) coated enzyme immunoassay plates at progressive two-fold dilutions. Bound E2 was detected using anti-E2 conformation-dependent antibody H53 and rabbit anti-mouse horseradish peroxidase (HRP) conjugate. Absorbance values were read at 450 nm-620 nm (background). Data is from a single experiment.

FIG. 16 shows the ability of E2 RBD (residues 384-661) containing multiple variable region deletions to bind CD81-LEL. A. Cell lysates from metabolically-labelled 293T cells transfected with wild-type (E2-myc), E2-myc containing multiple variable region deletions, or empty vector were applied to CD81 MBP-LEL (residues 113-201) coated enzyme immunoassay plates at progressive two-fold dilutions. Absorbance values were read at 450 nm-620 nm (background). B. Ability of secreted E2 RBD (residues 384-661) containing multiple variable region deletions to bind CD81-LEL. Supernatant fluid from metabolically-labelled 293T cells transfected with wild-type (E2-myc), E2-myc containing multiple variable region deletions or empty vector were applied to CD81 MBP-LEL (residues 113-201) coated enzyme immunoassay plates at progressive two-fold dilutions. Absorbance values were read at 450 nm-620 nm (background). Data is from a single experiment.

FIG. 19 discloses SEQ ID NOS 110-112, 109, 109, 95, 95, 109, 95, 109, 95, 95, 95, 109, 95 and 95, respectively, in order of appearance.

FIG. 20 discloses SEQ ID NOS 113, 114, 113, 114, 113, 114 and 113-115, respectively, in order of appearance.

FIG. 21 discloses SEQ ID NOS 110-112 and 116-118, respectively, in order of appearance.

FIG. 22 discloses SEQ ID NOS 110-112, 109, 109, 95, 95, 109, 95, 109, 95, 95, 95, 109, 95, and 95, respectively, in order of appearance.

FIG. 30 shows the ability of HCV E2-his proteins to bind to a recombinant form of the CD81 large extracellular loop (CD81-LEL). Enzyme immunoassay plates were coated with maltose binding protein fused to (A) wild-type large extracellular loop of CD81 (residues 113-201) (CD81-LEL) or (B) CD81-LEL containing an F186S mutation in the E2 binding site of CD81-LEL. Plates were blocked with bovine serum albumin and then incubated with serial dilutions of E2-his proteins (in 50 µl PBS containing 5 mg/ml bovine serum albumin and 0.05% Tween20) for 2 h. The bound E2-his proteins were detected using an E2 specific monoclonal antibody and rabbit anti-mouse immunoglobulins coupled to horseradish peroxidase (Dako). Plates were developed using tetramethylbenzidine hydrochloride substrate and stopped by the addition of 1M HCl. Absorbance was measured at 450 nm and the background at 620 nm subtracted. Percentage binding was calculated by dividing the absorbance value for each protein by the maximal absorbance obtained for wild-type E2-his and multiplied by 100.

FIG. 31 shows the immunoreactivity towards homologous E2-his antigen of mouse sera obtained after 2 immunizations with E2-his proteins. E2-his proteins were captured on 96 well Maxisorb microtitre plates (Num) precoated with galanthis nivalis (GNA) lectin. Serial dilutions of immune mouse sera were incubated with the captured corresponding E2 protein variant used for the immunization and bound immunoglobulins detected with rabbit anti-mouse immunoglobulin coupled to horseradish peroxidase. The assay was developed using tetramethylbenzidine hydrochloride substrate and stopped by the addition of 1M HCl. Absorbance values were measured at 450 nm and the background at 620 nm subtracted in a Fluostar plate reader (BMG technologies). The antibody titres of individual sera were determined as the serum dilution giving 5-times the background absorbance. The maximum (upper error bar), 75$^{th}$ and 25$^{th}$ percentile (upper and lower edges of box, respectively), median (horizontal line within box) and minimum (lower error bar) titres for each immunogen group are shown.

FIG. 35 shows the immunoreactivity towards Con1 E2$_{RBD}$-his (A) and JFH1 E2$_{RBD}$-myc (B) antigens of mouse sera obtained after 3 immunizations with E2 protein variants. Con1 and JFH1 RBD proteins were captured on 96 well Maxisorb microtitre plates and antibody titres determined for individual sera as described in FIG. 31. The maximum (upper error bar), $75^{th}$ and $25^{th}$ percentile (upper and lower edges of box, respectively), median (horizontal line within box) and minimum (lower error bar) titres for each immunogen group are shown.

DETAILED DESCRIPTION OF THE INVENTION

Figure 1:
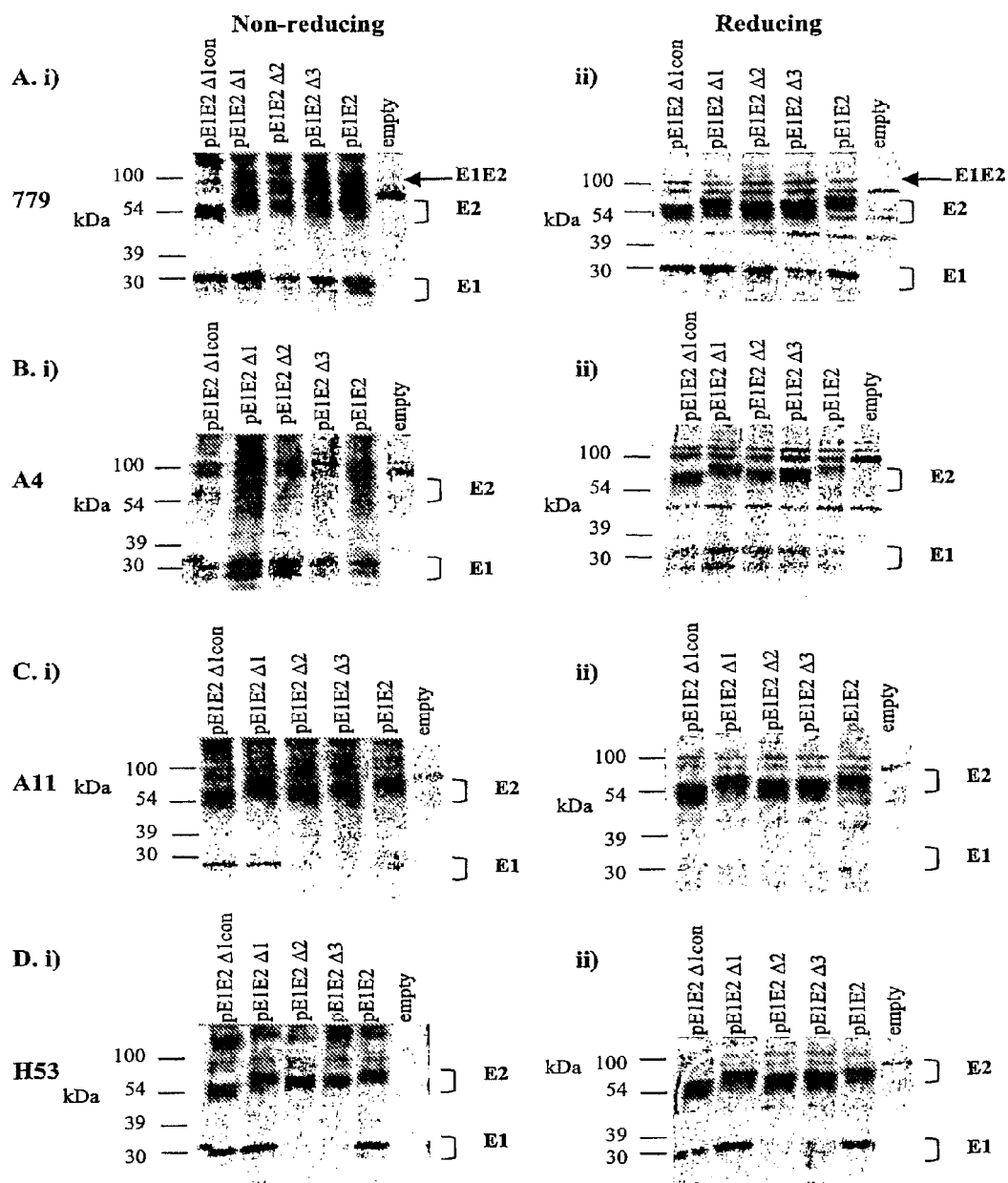
FIG. 1 shows the expression and heterodimerization of E1E2 containing single variable region deletions in cell lysates. Metabolically-labelled cell lysates of 293T cells transfected with wild-type (pE1E2), pE1E2 containing one variable region deletion, or empty vector were immunoprecipitated with A. anti-E1E2 polyclonal antibody (779), B. anti-E1 monoclonal antibody (A4), C. anti-E2 monoclonal antibody (A11) and D. anti-E2 conformation-dependent monoclonal antibody (H53) under both i) non-reducing and ii) reducing conditions (+β-mercaptoethanol). All samples were run on 10-15% SDS-PAGE gradient gels visualized using a phosphoimager. This data is representative of two independent experiments.

The modified E2 core structure of the HCV virion in which at least one of the variable regions, and in particular the variable region igVR identified by the inventors, has been modified by removal or deletion of at least a part of the variable region, and optional insertion of a linker sequence, has practical use as a vaccine that can elicit broadly neutralizing antibodies to diverse strains of HCV. The binding efficiency of the modified E2 glycoprotein exhibits wild-type binding to the HCV receptor CD81, and the modified E2 glycoprotein provides a means of treating HCV infection by mimicking complex conformational changes of the E2 ectodomain required for effective CD81 binding, and thereafter initiating an immune response without cell invasion.

In one aspect, the present invention provides a modified hepatitis C virus (HCV) E2 glycoprotein comprising the HCV-E2 receptor-binding domain (RBD) including the HVR1, HVR2 and igVR variable regions, wherein in at least one of said variable regions at least a part of the variable region is replaced with a flexible linker sequence.

In another aspect, the present invention provides a modified hepatitis C virus (HCV) E2 glycoprotein comprising the HCV-E2 receptor-binding domain (RBD) including the HVR1, HVR2 and igVR variable regions, wherein at least a part of the HVR2 variable region is removed or is replaced with a flexible linker sequence.

In yet another aspect, the present invention provides a modified hepatitis C virus (HCV) E2 glycoprotein comprising the HCV-E2 receptor-binding domain (RBD) including the HVR1, HVR2 and igVR variable regions, wherein at least a part of the igVR variable region is removed or is replaced with a flexible linker sequence.

References herein to the "HVR1" and "HVR2" variable regions are to be understood as references to the two variable regions HVR1 (384-410) and HVR2 (461-481), while references herein to the "igVR" variable region are to be understood as references to the intergenotypic variable region igVR (570-580) identified by the inventors.

The term "flexible linker sequence" is used herein to refer to a short, flexible, polypeptide sequence which permits disulfide bond linkages between cysteine residues in the modified glycoprotein leading to retention of the native or "wild-type" disulfide linkages, and in particular retention of the ability to bind to the HCV CD81 receptor and conformation-dependent antibodies. Suitable linker sequences are discussed in review articles by George and Heringa, 2002, and Argos, 1990, and may consist of up to 20 amino acid residues such as Gly and Ser, and include, and comprise amino acids selected from the sequence group consisting of Gly, Ser, Ala, Thr and Arg, more particularly Gly- and Ser-Ser-Gly (GSSG) (SEQ ID NO: 95). Suitable linker sequences include, by way of example, the sequences (Gly)$_2$-Ala-(Gly)$_2$ (SEQ ID NO: 96), (Gly)$_5$ (SEQ ID NO: 97) or (Gly)$_8$ (SEQ ID NO: 98) (see Sabourin et al., 2007), (Gly)$_6$ (SEQ ID NO: 99), (Gly)$_7$ (SEQ ID NO: 100) or (Gly)$_{10}$ (SEQ ID NO: 101) (see Yang and Gruebele, 2006), Gly-Ser-Gly-Ser-Gly (SEQ ID NO: 102) (see Dipti et al., 2006), (Gly)$_4$ (SEQ ID NO: 103) (see Anandarao et al., 2006), Gly-Ala-Gly (see Wyatt et al., 1995), (Gly)$_2$-Arg-(Gly)$_2$-Ser (SEQ ID NO: 104) (see Bellamy-McIntyre et al., 2007), (Gly-Gly-Gly-Gly-Ser)$_{n=3-4}$ (SEQ ID NO: 105) (see Arai et al., 2006), and Ser-(Gly)$_2$-Ser-Gly (SEQ ID NO: 106) (see Bahrami et al., 2007).

A preferred sequence is the sequence Gly-(Ser)$_2$-Gly (SEQ ID NO: 95) disclosed herein. It will be understood that selection of suitable polypeptide linker sequences is a matter of routine experimentation for a person skilled in this field, and the modified HCV E2 glycoproteins of the present invention are not limited to the particular linker sequences disclosed herein. Without wishing to be bound by any theory, by replacing HVR1, HVR2 and igVR with short flexible linkers, disulfide-bond formation between Cys-569 to Cys-581 and between Cys-459 to Cys-486, for example, and the intrinsic folding of conserved E2 core domain, is substantially retained in the modified glycoproteins.

References in this specification to "deletion" of at least part of one of the variable regions of the HCV E2 receptor-binding domain are to be understood as references to deletion or removal of at least part of the sequence of the variable region and optional insertion of a flexible linker sequence to replace the deleted sequence.

The modified HCV E2 glycoproteins of the present invention may be prepared by any suitable method, including in particular preparation of the modified glycoproteins in the form of recombinant products by expression of appropriate DNA deletion constructs as described in the Examples herein.

Preferably at least one of the second and third variable regions of the core E2 receptor-binding domain, HVR2 and igVR, is modified by removal of at least a portion of the residue within the region and inserting a flexible linker sequence. It has been found that deletion of at least part of the HVR2 region, in combination with other variable region deletions, substantially reduces E1E2 heterodimerisation.

In a further embodiment, all three of the variable regions are modified by removal of at least a portion of the residues within these regions and inserting a linker sequence.

Deletion of intergenotypic variable region (igVR) from the E2 glycoprotein that already contains deletions of HVR1 and HVR2 improves binding to CD81 relative to simultaneous deletions of HVR1 and HVR2 alone.

It has been found by the inventors that HVR1, HVR2, and igVR are all required for E1E2-pp mediated viral entry into Huh7 cells. E1E2-pp containing deletions of at least each of HVR1, HVR2, and igVR have been found to retain wild-type levels of recombinant CD81 binding. This represents a significant improvement in the ability to (a) mimic cell binding of the HCV virion, and (b) initiate an immune response without exposing a patient to highly variable immunodominant regions that may be immune decoys.

In a preferred embodiment, all three variable regions can be deleted and retain the core E2 folding domain which is required to assemble at least three discontinuous binding elements involved in the CD81-binding site. A further advantage of various combined deletions of HVR1, HVR2, and igVR from the E2 receptor-binding domain is that a soluble form of the E2 core domain is obtainable, which is suitable for use as an immunogen.

The present invention also provides a composition comprising a modified HCV E2 glycoprotein as broadly described above, together with a pharmaceutically acceptable carrier or diluent.

Such a composition may be formulated as a vaccine composition, preferably including an adjuvant.

Conventional pharmaceutically acceptable carriers, excipients, buffers or diluents, may be included in vaccine compositions of this invention. Generally, a vaccine composition in accordance with the present invention will comprise an immunologically effective amount of the modified HCV E2 glycoprotein, and optionally an adjuvant, in conjunction with one or more conventional pharmaceutically acceptable carriers and/or diluents. An extensive though not exhaustive list of adjuvants can be found in Cox and Coulter, "Advances in Adjuvant Technology and Application", in *Animal Parasite Control Utilizing Biotechnology*, Chapter 4, Ed. Young, W. K., CRC Press 1992, and in Cox and Coulter, "Adjuvants—A Classification and Review of Their Modes of Action", *Vaccine* 15(3), 248-256, 1997. As used herein "pharmaceutically acceptable carriers and/or diluents" include any and all solvents, dispersion media, aqueous solutions, coatings, antibacterial and antifungal agents, isotonic and absorption delaying agents and the like. The use of such media and agents for pharmaceutical active substances is well known in the art and is described by way of example in *Remington's Pharmaceutical Sciences*, $18^{th}$ Edition, Mack Publishing Company, Pennsylvania, U.S.A.

In yet another aspect, the present invention also provides a method of eliciting an immune response in a patient, which comprises administration to the patient of an effective amount of a modified HCV E2 glycoprotein as broadly described above.

In this aspect, the invention includes a method for prophylactic or therapeutic treatment of HCV infection in a patient, which comprises administration to the patient of an effective amount of a modified HCV E2 glycoprotein as broadly described above.

Reference herein to "treatment" is to be understood in its broadest context. Accordingly, the term "prophylactic treatment" includes treatment to protect the patient against infection or to reduce the likelihood of infection. Similarly, the term "therapeutic treatment" of infection does not necessarily imply that the patient is treated until total recovery from infection, and includes amelioration of the symptoms of infection as well as reducing the severity of, or eliminating, the infection.

The modified HCV E2 glycoprotein of this invention is administered in an effective amount. An "effective amount" means an amount necessary at least partly to attain the desired response, or to delay the onset or inhibit progression or halt altogether, the onset or progression of the infection. The amount varies depending upon the health and physical condition of the individual to be treated, the racial background of the individual to be treated, the degree of protection desired, the formulation of the composition, the assessment of the medical situation, and other relevant factors. It is expected that the amount will fall in a relatively broad range that can be determined through routine trials. If necessary, the administration of an effective amount may be repeated one or several times. The actual amount administered will be determined both by the nature of the infection which is being treated and by the rate at which the active immunogen is being administered.

Preferably, the patient is a human, however the present invention extends to treatment and/or prophylaxis of other mammalian patients including primates and laboratory test animals (e.g. mice, rabbits, rats, guinea pigs).

In accordance with the present invention, the modified HCV E2 glycoprotein is preferably administered to a patient by a parenteral route of administration. Parenteral administration includes any route of administration that is not through the alimentary canal (that is, not enteral), including administration by injection, infusion and the like. Administration by injection includes, by way of example, into a vein (intravenous), an artery (intraarterial), a muscle (intramuscular) and under the skin (subcutaneous). The modified HCV E2 glycoprotein may also be administered in a depot or slow release formulation, for example, subcutaneously, intradermally or intramuscularly, in a dosage which is sufficient to obtain the desired pharmacological effect.

Compositions suitable for parenteral administration conveniently comprise a sterile aqueous preparation of the active component which is preferably isotonic with the blood of the recipient. This aqueous preparation may be formulated according to known methods using suitable dispersing or wetting agents and suspending agents. The sterile injectable preparation may also be a sterile injectable solution or suspension in a non-toxic parenterally-acceptable diluent or solvent, for example as a solution in a polyethylene glycol and lactic acid. Among the acceptable vehicles and solvents that may be employed are water, Ringer's solution, suitable carbohydrates (e.g. sucrose, maltose, trehalose, glucose) and isotonic sodium chloride solution. In addition, sterile, fixed oils are conveniently employed as a solvent or suspending medium. For this purpose, any bland fixed oil may be employed including synthetic mono- or di-glycerides. In addition, fatty acids such as oleic acid find use in the preparation of injectables.

In a further aspect, this invention provides the use of a modified HCV E2 glycoprotein as broadly described above in, or in the manufacture of a medicament for, eliciting an immune response in a patient.

In a further aspect, this invention includes the use of a modified HCV E2 glycoprotein as broadly described above in, or in the manufacture of a medicament for, prophylactic or therapeutic treatment of HCV infection in a patient.

In this further aspect, this invention provides an agent for eliciting an immune response in a patient, which comprises a modified HCV E2 glycoprotein as broadly described above.

In this further aspect, the invention includes an agent for prophylactic or therapeutic treatment of HCV infection in a patient, which comprises a modified HCV E2 glycoprotein as broadly described above.

In one embodiment of the invention, it has been found that recombinant E2 glycoprotein in which at least region igVR is subject to deletion of residues in the region and replacement with a flexible linker sequence improves recognition by conformational-dependent antibodies. In addition, it has been found that, in a comparative study with 'wild-type' E2 glycoprotein, modification of the region igVR alone and in various combinations with HVR1 and HVR2 show binding to full-length CD81-LEL (large extracellular loop of human tetraspanin CD81) approaching that of the wild-type.

It has been shown by the inventors that alignment of diverse E2 glycoprotein sequences across the six major genotypes identified a novel third variable region, "igVR," between residues 560 and 581. It is suggested that "igVR" is not strictly a hypervariable region as it exhibits its greatest variability across different genotypes, whereas it is relatively conserved within a genotype and is thus unlikely to be under immune selection pressure. Furthermore, it consists of a series of insertions or deletions that shifts, but always maintains, the glycosylation site located within this region. The inventors have also observed that both variable regions HVR2 and "igVR" are flanked by conserved cysteine residues and proposed that these regions may form solvent-exposed loops stabilised by disulfide-bonding between these residues.

The inventors have proposed that the hypervariable regions form flexible solvent-exposed subdomains that enable the E2 glycoprotein to move between 'open' and 'closed' conformations, the former being more competent for CD81 binding by exposing the conserved CD81-binding determinants located within the core E2 domain as delineated within this study. Indeed, conformational changes within the E2 glycoprotein have been previously observed upon CD81-binding. In addition, binding of non-neutralizing antibodies to the E2 glycoprotein has been demonstrated to reduce its susceptibility to neutralizing antibodies and is consistent with a model where the non-neutralizing antibodies inhibit the flexibility of these surface-exposed hypervariable regions thus blocking access to the conserved epitopes located within the E2 core domain.

Therefore, this suggests that the modified E2 core domain represents a promising vaccine candidate for eliciting neutralizing antibodies to conserved epitopes within the E2 glycoprotein, including the CD81-binding determinants, that are otherwise occluded by these surface-exposed variable regions that may act as immunological decoys at the surface of the glycoprotein complex during HCV replication.

The present invention also provides an isolated antibody raised against a modified HCV E2 glycoprotein as broadly described above.

The term "antibody" is used broadly herein to include both monoclonal and polyclonal antibodies that specifically bind to the modified HCV E2 glycoprotein, as well as antigen binding fragments of such antibodies including, for example, Fab, $F(ab^1)_2$, Fd and Fv fragments of an antibody that retain specific binding activity for the modified HCV E2 glycoprotein.

Antibodies having the desired specificity, both monoclonal and polyclonal, can be obtained using methods which are well known in the art (see, for example, Harlow and Lane, "Antibodies, A laboratory manual", Cold Spring Harbor Laboratory Press, 1988). Methods for preparing antibodies, and antigen binding fragments thereof, are also described in International Patent Publication WO 02/22155.

The invention also provides a method for prophylactic or therapeutic treatment of HCV infection in a patient, which comprises administration to the patient of an effective amount of an antibody as described above. Accordingly, this method provides passive immunotherapy of the patient.

As previously described, the invention also provides the use of an antibody as described above in, or in the manufacture of a medicament for, prophylactic or therapeutic treatment of HCV infection in a patient.

In this aspect also, the invention provides an agent for prophylactic or therapeutic treatment of HCV infection in a patient, which comprises an antibody as described above.

Further, the invention provides the use of an antibody as broadly described above in diagnosis of HCV infection. In this aspect, the invention provides a method of detecting HCV infection in a patient, comprising contacting a biological sample from the patient with an antibody as described above under conditions which allow formation of an antibody-antigen complex, and detecting said complex, wherein formation of said complex is indicative of the presence of HCV in the sample.

Preferably, the antibody is detectably labelled. Suitable labels are well known in the art and include, for example, enzymes, radioisotopes, fluorescent compounds, colloidal metals, and chemiluminescent, phosphorescent and bioluminescent compounds. Preferably, the biological sample is a sample of a body fluid from the patient, such as a blood sample.

The modified HCV E2 glycoproteins of the present invention may also be used in drug discovery techniques, including for example small molecule screening techniques.

The present invention is further illustrated by the following non-limiting Examples.

EXAMPLE 1

Materials and methods used in this Example are described below.
1. Role of the Individual Variable Regions in E1E2 Glycoprotein Structure and Function.

The results for the various variable deletion mutants are summarized in Table 1.
Intracellular E1E2 Precursor Folding and Heterodimerisation To examine the role of the individual variable regions in intracellular E1E2 biosynthesis, metabolically-labelled cell lysates of 293T cells transfected with the single variable region deletion constructs were immunoprecipitated with antibodies reactive to E1 and/or E2 epitopes. These preparations were analysed under both non-reducing and reducing conditions to characterise non-covalently associated E1E2 heterodimers existing within the large intracellular population of covalently-linked aggregate as previously observed.

Immunoprecipitation with the polyclonal anti-E1E2 antibody (779) detected the total intracellular population of E1 (~30 kDa) and E2 (~70 kDa) glycoproteins to show efficient expression and cleavage from the polyprotein occurring for each single variable region deletion construct (see FIG. 1A). The mutant E2 glycoproteins exhibited variably lower molecular weights than wild-type: HVR1con<HVR2 and "igVR"<HVR1<WT. This is consistent with the loss of two glycosylation sites predicted to reside within the HVR1con deletion, one within each of the HVR2 and "igVR" deletions and none within the HVR1 deletion (FIG. 2). However, deglycosylation of these E2 glycoproteins is required to confirm their backbone molecular weights as predicted in Table 2. The band migrating to ~100 kDa represents the E1E2 polyprotein that has not been cleaved by host signal peptidases and is more pronounced in both the single HVR2 and "igVR" deletion constructs (FIG. 1A). This is reflected in the reduced levels of total intracellular E1 and E2 observed for the HVR2 and "igVR" mutants suggesting that these deletions may be effecting polyprotein processing.

The non-conformation-dependent anti-E1 monoclonal antibody (A4) precipitated an E1 doublet at ~30 kDa and ~27 kDa for both the mutant and the wild-type constructs under reducing and non-reducing conditions (FIG. 1B). This doublet represents either alternative E1 glycosylation states or messenger RNA splicing isoforms as previously observed. Furthermore, E1 co-precipitated low levels of the wild-type E2 glycoprotein under non-reducing conditions, whereas it efficiently co-precipitated both wild-type and mutant E2 glycoproteins under reducing conditions. This indicates that A4 recognises an E1 epitope that is more exposed within covalently-linked intracellular E1E2 complexes.

The non-conformation dependent anti-E2 monoclonal antibody (A11) detected intracellular E2 glycoprotein expression for all the individual variable region deletion constructs (FIG. 1C). However, only the mutant E2 glycoproteins containing the HVR1con or HVR1 deletions co-precipitated a detectable amount of E1 under non-reducing and reducing conditions. This indicates that the individual HVR2 and "igVR" deletions are either directly or indirectly disrupting the formation of the intracellular E1E2 heterodimer Notably, this reduced heterodimerisation is not due to the lower total intracellular E1 and E2 observed for the HVR2 and "igVR" deletions as E2 glycoprotein expression was detected at wild-type levels by A11 in both these mutants. In addition, E2 co-precipitated generally low levels of E1, particularly under reducing conditions, suggesting that the A11 epitope is partly occluded in intracellular E1E2 heterodimer complexes.

The conformation-dependent anti-E2 monoclonal antibody (H53) has been shown to recognise native E2 on the surface of HCV virions and thus the amount of E1 co-precipitating with this E2 species is a good indicator of the proportion of functional non-covalently associated E1E2 heterodimers forming. Immunoprecipitation with H53 detected intracellular E2 glycoprotein expression for all individual variable region deletion constructs (FIG. 1D). This indicates that the inserted Gly-Ser-Ser-Gly linker motif (SEQ ID NO: 95) provides sufficient flexibility within these E2 glycoproteins to retain the intrinsic folding of the native E2 glycoprotein required to present this conformation-dependent epitope. However, the intracellular E2 glycoproteins containing HVR2 or "igVR" deletions failed to co-precipitate E1, suggesting that these regions are directly or indirectly required in the intracellular assembly of the non-covalently associated E1E2 heterodimer.
E1E2 Glycoprotein Maturation and Incorporation into Pseudotyped HIV-1 Particles To examine the role of the individual variable regions in E1E2 glycoprotein maturation, the small amount of E1 and E2 escaping from the ER to transit through the secretory pathway was enriched for by the incorporation of these complexes into pseudotyped HIV-1 particles as previously described. These metabolically-labelled E1E2-pseudotyped HIV-1 particles were lysed prior to immunoprecipitation with the conformation-dependent anti-E2 monoclonal antibody (H53) and IgG from an HIV-1 infected individual (IgG14).

Figure 3:
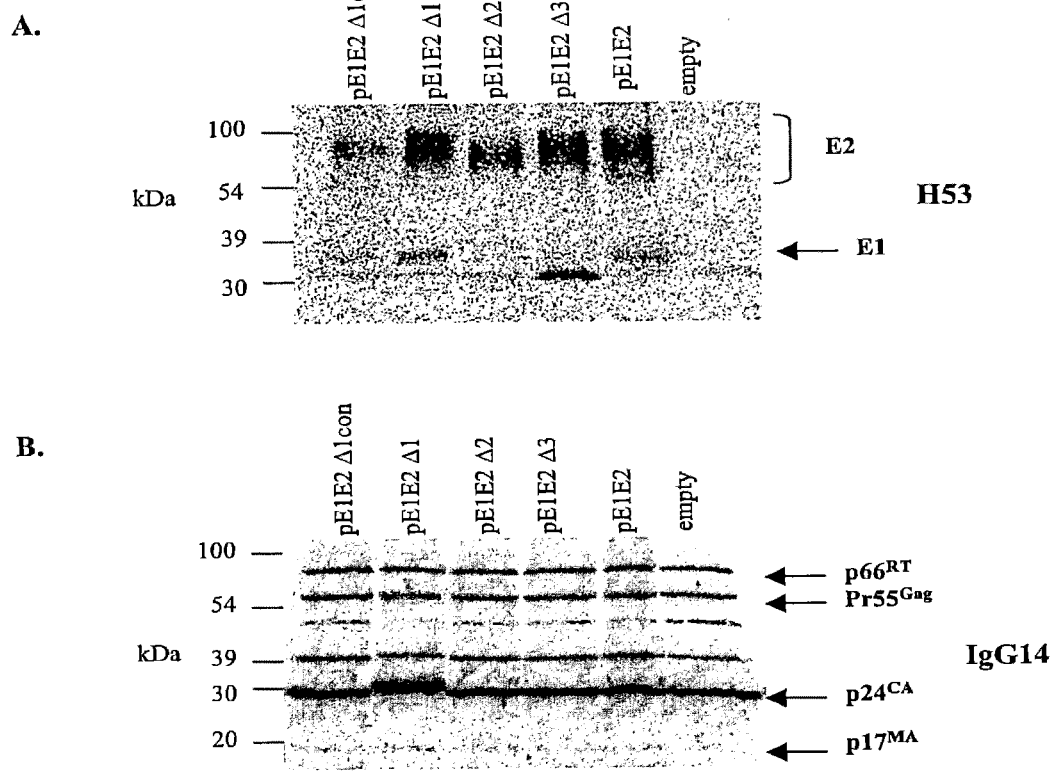
FIG. 3 shows the incorporation of E1E2 glycoproteins containing single variable region deletions into retroviral pseudotyped HIV-1 particles. A. Metabolically labelled HCV glycoprotein pseudotyped HIV-1 particles were pelleted from the tissue culture fluid of 293T cells transfected with wild-type (pE1E2), pE1E2 containing a variable region deletion or empty vector prior to lysis. E1E2 heterodimers were immunoprecipitated with the conformation-dependent anti-E2 monoclonal antibody H53. All samples were separated on a 10-15% SDS-PAGE gradient gel under non-reducing conditions and visualized using a phosphoimager. B. Processing and incorporation of HIV-1 structural proteins into retroviral pseudotyped HIV-1 particles. HIV-1 structural proteins $Pr55^{Gag}$, $p24^{CA}$ $p66^{RT}$ and $p17^{MA}$ from lysed metabolically-labelled HCV glycoprotein pseudotyped HIV-1 particles were immunoprecipitated using IgG from an HIV-1 infected individual (IgG14). All samples were separated on a 7.5-15% SDS-PAGE gradient gel and visualized using a phoshoimager. This data is representative of two independent experiments.

Immunoprecipitation with IgG14 demonstrated that none of the single variable region deletion constructs had affected processing and virion incorporation of the HIV-1 structural proteins Pr55$^{Gag}$, p17$^{MA}$, p24$^{CA}$ or p66$^{RT}$ (FIG. 3B). Immunoprecipitation with H53 detected the virion-incorporated E2 glycoprotein as a diffuse molecular weight band (~70-90 kDa) typical of the mature glycoprotein containing various complex- and hybrid-type carbohydrate modifications as previously described (FIG. 3A). The different mutant E2 glycoproteins exhibited further variation in their relative molecular weights (HVR1con<HVR2 and "igVR"<HVR1<WT) reflecting the loss of glycosylation sites located within these deleted regions as described for the intracellular data. All mutant E2 glycoproteins were incorporated into E1E2-pseudotyped HIV-1 particles at approximately wild-type levels, except for the HVR1con deletion that showed a significantly reduced E2 band. This suggests that the conserved region adjacent to HVR1 is required for the completion of E2 folding, maturation and incorporation into pseudotyped HIV-1 particles.

Immunoprecipitation with H53 also detected a protein species migrating at ~33 kDa and another lower molecular weight band at ~31 kDa initially suggesting that the virion-incorporated E1 glycoprotein also migrates as a doublet (FIG. 3A). However, across two independent experiments, the lower molecular weight band co-migrated with a non-specific band in the negative control (empty) and thus the higher molecular weight band alone is likely to represent E1. The virion-incorporated E1 glycoprotein (~33 kDa) also migrates more slowly than the intracellular species (~30 kDa) reflecting additional carbohydrate modifications at one or two E1 glycosylation sites acquired during transit through the secretory pathway as previously observed. Furthermore, the virion-incorporated E2 glycoproteins containing the individual HVR2 and "igVR" deletions could not co-precipitate E1 at detectable levels indicating that these variable regions are directly or indirectly required in the formation of the functional E1E2 heterodimer.

E1E2-Mediated Entry into Huh7 Cells

Figure 4:
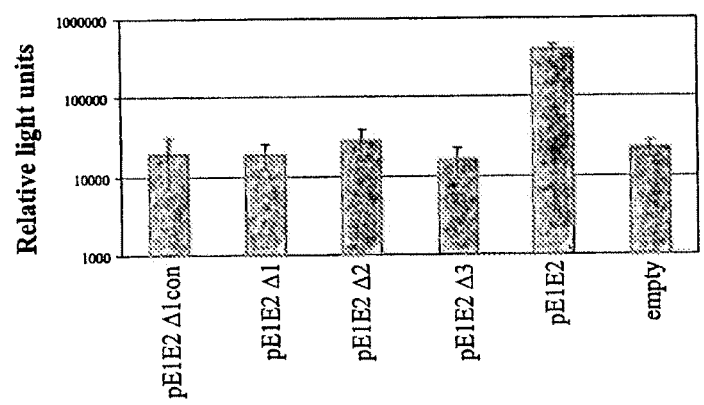
FIG. 4 shows the ability of HCV glycoprotein pseudotyped HIV-1 particles containing single variable region deletions to enter Huh7 cells. The tissue culture fluid from 293T cells co-transfected with the vector NL4-3.LUC.R–E– and either wild-type (pE1E2), pE1E2 containing a deletion in a variable region, or empty vector was used to infect Huh7 cells in triplicate. The Huh7 cells were lysed and the luciferase activity (relative light units) measured using a Fluostar fitted with luminescence optics. Mean and standard deviation was calculated from triplicate infections. Data is representative of three independent experiments.

The formation of the functional non-covalently associated E1E2 heterodimer has been shown to be critical for E1E2-mediated entry into Huh-7 cells. In order to investigate the role of the individual variable regions in viral entry, the single deletion constructs were used to generate E1E2-pseudotyped HIV-1 particles to infect Huh7 cells as previously described. As expected, the HVR1con deletion conferred a total loss of entry due to its retarded incorporation of the E2 glycoprotein into pseudotyped HIV-1 virions as observed above (FIG. 4). Similarly, the HVR2 and "igVR" deletions were not entry competent due to the disruption of the functional E1E2 heterodimer complex. However, the HVR1 deletion also conferred a total loss of entry despite retaining both wild-type heterodimerisation levels and incorporation of E1E2 glycoproteins into HIV-1 virions suggesting that this region may have a direct role in E1E2-mediated viral entry.

CD81-LEL Binding

It has been previously demonstrated that the E2 glycoprotein alone is sufficient to mediate binding to the CD81 receptor and therefore, despite exhibiting a loss of heterodimerisation and/or viral entry, both intracellular and virion-incorporated mutant E2 glycoproteins were examined for their ability to bind to the large-extracellular loop (LEL residues 113-201) of CD81. This involved applying both cell and viral lysates to a solid-phase CD81 MBP-LEL (residues 113-201) binding assay as previously described. This data was normalized for the amount of monomeric E2 expressed from each vector as precipitated with the conformation-dependent anti-E2 monoclonal antibody H53 and observed by SDS-PAGE under non-reducing conditions; FIGS. 1D (intracellular) and 3A (virion-incorporated).

All intracellular E2 glycoprotein precursors containing the single variable region deletions exhibited CD81-LEL binding at wild-type levels, except for HVR1 con that demonstrated a total loss of binding (FIG. 5A). This indicates that the inserted Gly-Ser-Ser-Gly linker motifs (SEQ ID NO: 95) are providing sufficient flexibility within the HVR1, HVR2 and "igVR" deleted E2 glycoproteins to form the E2 CD81-binding site and suggests that these individual variable regions are not required in this function. It also indicates that the intracellular E2 glycoprotein precursor lacking the conserved region adjacent to HVR1 (HVR1 con) cannot form the CD81-LEL binding site despite maintaining the conformation-dependent epitope recognised by H53. Intracellular forms of both the HVR2 and "igVR" deletions displayed an additional enhancement of maximum CD 81-LEL binding compared to wild-type (FIG. 5A) although they did not exhibit a significant shift in the overall binding curve and thus additional independent experiments are required to determine whether these variable regions are modulating CD81-LEL binding.

As expected, the virion-incorporated E2 glycoprotein containing the HVR1con deletion could not mediate CD81-LEL binding, reflecting both its reduced incorporation into E1E2-pseudotyped HIV-1 particles as well as the intracellular data above (FIG. 5B). In contrast, the virion-incorporated E2 glycoproteins containing the HVR1, HVR2 and "igVR" deletions all retained at least wild-type levels of CD81-LEL binding indicating that these mutant E2 glycoproteins retain the CD81-binding site even after maturation. Interestingly, the virion-incorporated E2 glycoprotein containing the HVR1 deletion demonstrated an additional enhancement of maximum CD81-LEL binding compared to wild-type and exhibited an approximately 4-fold increase in the overall binding curve (FIG. 5B). This suggests that HVR1 is negatively modulating CD81-LEL binding within the virion-incorporated E2 glycoprotein despite not being required for this function. The observed absence of this effect in the intracellular E2 glycoprotein precursor containing the same deletion (FIG. 5A) reflects changes in E1E2 folding and the CD81-binding site that occur during glycoprotein maturation through the secretory pathway as previously observed.

2. Effect of the Extended Linker on E1E2 Glycoprotein Structure and Function

Intracellular E1E2 Precursor Folding and Heterodimerisation

In order to enhance the folding of the E2 glycoproteins containing the individual variable region deletions, the Gly-Ser-Ser-Gly linker (SEQ ID NO: 95) was extended by reintroducing several conserved cysteine-proximal residues deleted from the original constructs. Notably, this series of modified deletion constructs does not have a HVR1 counterpart due to the highly variable nature of this region. These constructs were analysed for E1 and E2 glycoprotein expression and heterodimerisation within 293T cells by pulse-chase metabolic-labelling and immunoprecipitation.

Figure 6:
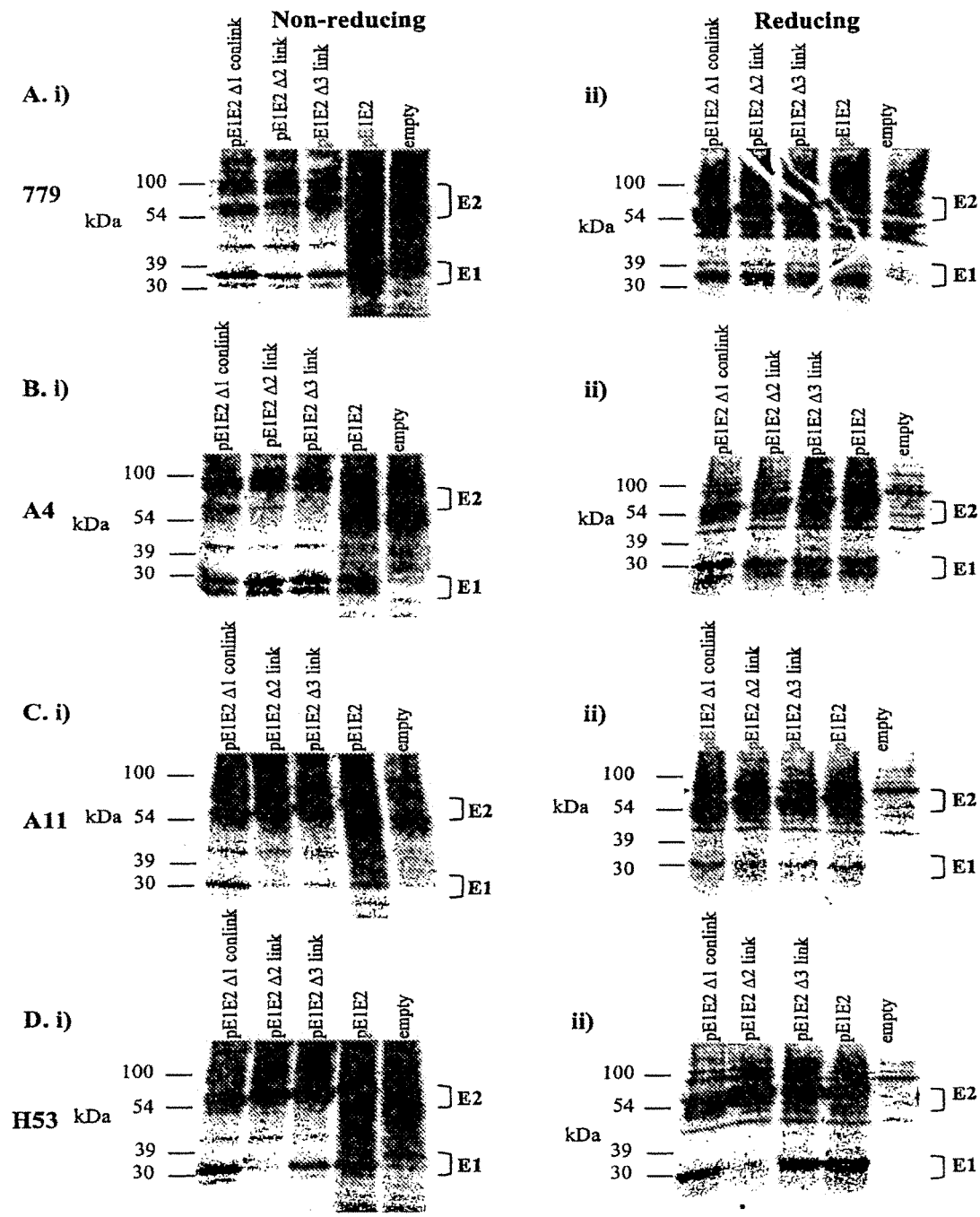
FIG. 6 shows the expression and heterodimerization of E1E2 containing modified single variable region deletions in cell lysates. Metabolically-labelled cell lysates of 293T cells transfected with wild-type (pE1E2), or pE1E2 containing single variable region deletions with an extended linker, or empty vector were immunoprecipitated with A. anti-E1E2 polyclonal antibody (779), B. anti-E1 monoclonal antibody (A4), C. anti-E2 monoclonal antibody (A11) and D. anti-E2 conformation-dependent monoclonal antibody (H53) under both i) non-reducing and ii) reducing conditions (+β-mercaptoethanol). All samples were run on 10-15% SDS-PAGE gradient gels and visualized using a phosphorimager. Data is representative of two independent experiments.

Immunoprecipitation with the anti-E1E2 polyclonal antibody (779) detected intracellular expression and cleavage of the E1 (~30 kDa) and E2 (~70 kDa) glycoproteins from the polyprotein occurring for each extended linker deletion construct (FIG. 6A). Polyprotein cleavage appeared to be slightly less efficient in the HVR2link and "igVR link" constructs suggesting that these deletions may be affecting polyprotein processing. The extended linkers did not restore the glycosylation sites deleted from the original constructs and thus the mutant E2 glycoproteins again exhibited variably lower molecular weights (kDa) than the wild-type conferred by the absence of these glycans: HVR1conlink<HVR2link and "igVR link"<WT. However, deglycosylation of these E2 glycoproteins would be required to verify their backbone molecular weights as predicted in Table 2.

The anti-E1 monoclonal antibody (A4) detected the presence of the E1 doublet (~30 kDa and ~27 kDa) for all extended linker constructs (FIG. 6B). E1 failed to co-precipitate wild-type E2 glycoprotein under non-reducing conditions, whereas it co-precipitated both mutant and wild-type E2 under reducing conditions again reflecting the low sensitivity of the A4 antibody for non-covalently associated E1. Precipitation with the non-conformation dependent anti-E2 monoclonal antibody (A11) detected wild-type E2 glycoprotein expression for each extended linker construct although only the HVR1 conlink deletion co-precipitated detectable amounts of E1 (FIG. 6C). The conformation-dependent monoclonal antibody (H53) also precipitated wild-type levels of the intracellular E2 glycoprotein for each extended linker construct indicating that these mutants retain the intrinsic folding properties of the native E2 glycoprotein required to present this conformation-dependent epitope (FIG. 6D). Furthermore, the extended "igVR" linker recovered co-precipitation with E1 at wild-type levels suggesting that this additional linker region is required, directly or indirectly, for the intracellular assembly of the non-covalently associated E1E2 heterodimer Notably, however, this effect was not observed for the extended HVR2 linker construct.

E1E2 Glycoprotein Maturation and Incorporation into Pseudotyped HIV-1 Particles

To examine whether the extended linkers altered E1E2 glycoprotein maturation and virion incorporation, the modified single deletions were introduced into E1E2-pseudotyped HIV-1 particles prior to lysis and immunoprecipitation with the conformation-dependent anti-E2 monoclonal antibody (H53) and IgG from an HIV-1 infected individual (IgG14) as previously described.

Figure 7:
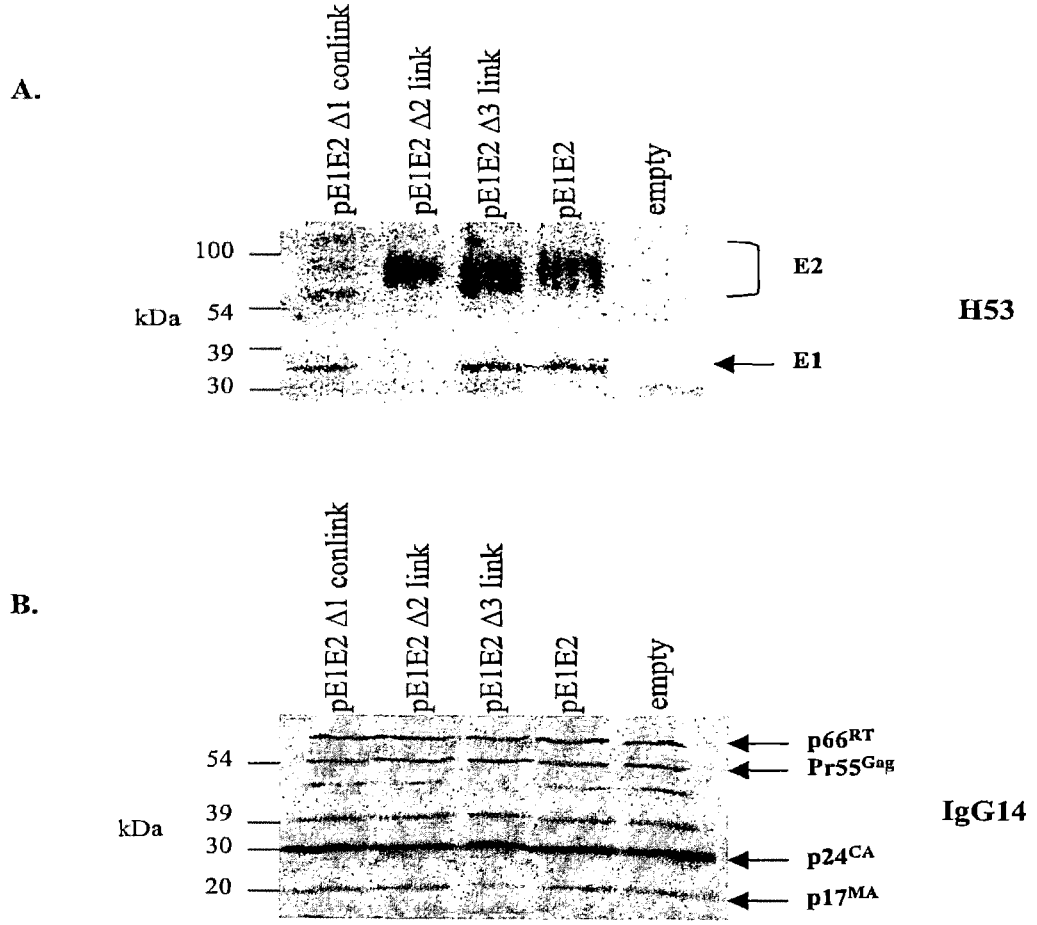
FIG. 7 shows the incorporation of E1E2 glycoproteins containing modified single variable region deletions into HCV glycoprotein pseudotyped HIV-1 particles. A. Metabolically labelled E1E2-pseudotyped HIV-1-particles were pelleted from the tissue culture fluid of 293T cells transfected with NL4-3.LUC.R–E– and wild-type (pE1E2), containing single variable region deletions with an extended linker, or empty vector prior to lysis. E1E2 heterodimers were immunoprecipitated with the conformation-dependent anti-E2 monoclonal antibody H53. All samples were separated under non-reducing conditions on a 10-15% SDS-PAGE gradient gel and visualized using a phosphoimager. B. Processing and incorporation of HIV-1 structural proteins into HCV glycoprotein-pseudotyped HIV-1 particles. HIV-1 structural proteins $Pr55^{Gag}$, $p17^{MA}$, $p24^{CA}$ and $p66^{RT}$ from lysed metabolically-labelled E1E2-pseudotyped HIV-1 particles were immunoprecipitated using IgG from an HIV-1 infected individual (IgG14). All samples were separated on a 7.5-15% SDS-PAGE gradient gel and visualized using a phosphorimager. Data is representative of two independent experiments.

Immunoprecipitation with IgG14 indicated that none of the modified single deletion constructs affected processing and virion incorporation of the HIV-1 structural proteins (FIG. 7B). Precipitation with H53 again detected a diffuse molecular weight band (~70-90 kDa) typical of the mature virion-incorporated E2 glycoprotein (FIG. 7A). The virion-incorporated mutant E2 glycoproteins also exhibited marginally lower molecular weights (kDa) than the wild-type species conferred by the loss of one or two glycosylation sites as described for the intracellular data. Precipitation with H53 again demonstrated reduced virion-incorporation of the E2 glycoprotein containing the HVR1conlink deletion despite the reintroduction of four conserved cysteine-proximal residues absent in the original HVR1con deletion construct. The HVR2link deletion demonstrated wild-type levels of E2 glycoprotein incorporated into pseudotyped HIV-1 particles, yet still failed to co-precipitate a detectable amount of E1 reflective of the intracellular data. In contrast, the virion-incorporated E2 glycoprotein containing the extended "igVR" linker co-precipitated wild-type levels of E1 suggesting that this region is directly or indirectly required in the formation of the functional E1E2 heterodimer.

E1E2-Mediated Entry into Huh7 Cells

Figure 8:
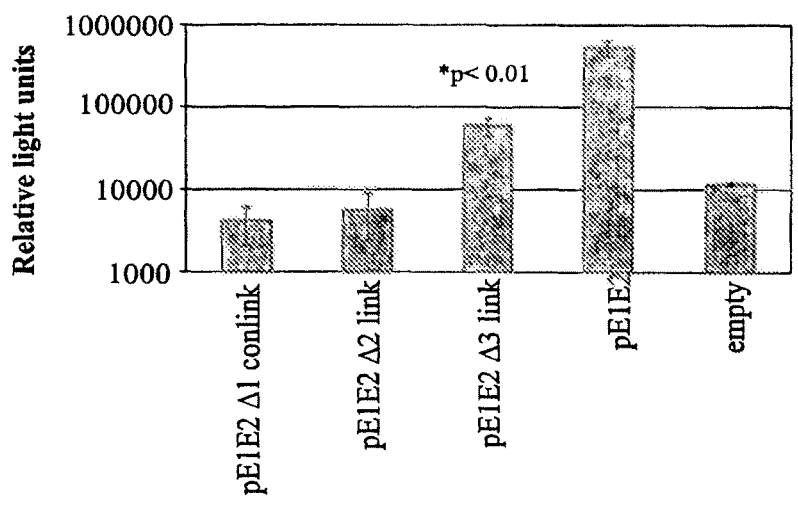
FIG. 8 shows the ability of HCV glycoprotein-pseudotyped HIV-1 particles containing single modified variable region deletions to enter Huh7 cells. The tissue culture fluid from 293T cells co-transfected with NL4-3.LUC.R–E– and either wild-type (pE1E2), containing single variable region deletions with an extended linker, or empty (pCDNA4) vector was used to infect Huh7 cells in triplicate. The Huh7 cells were lysed and the luciferase activity (relative light units) measured using a Fluostar fitted with luminescence optics. Mean and standard deviation was calculated from triplicate infections. p-value was calculated using the student's t-test. Data is representative of three independent experiments.

To examine whether these extended linkers conferred E1E2-mediated entry into Huh-7 cells, these modified single deletion constructs were used to generate E1E2-pseudotyped HIV-1 particles to infect Huh7 cells as previously described. As expected, the extended linkers in the HVR1conlink and HVR2link deletion constructs did not recover any entry activity consistent with the observed failure of these mutant E2 glycoproteins to be incorporated into virions or heterodimerise, respectively (FIG. 8). However, the virion-incorporated E2 glycoprotein containing the extended "igVR" linker demonstrated a significant return of entry activity (~8-fold) compared to the negative control (empty) consistent with its recovered heterodimerisation with E1. Notably, however, "igVR link" still exhibited reduced entry activity compared to wild-type (~10-fold).

CD81-LEL Binding

Figure 9:
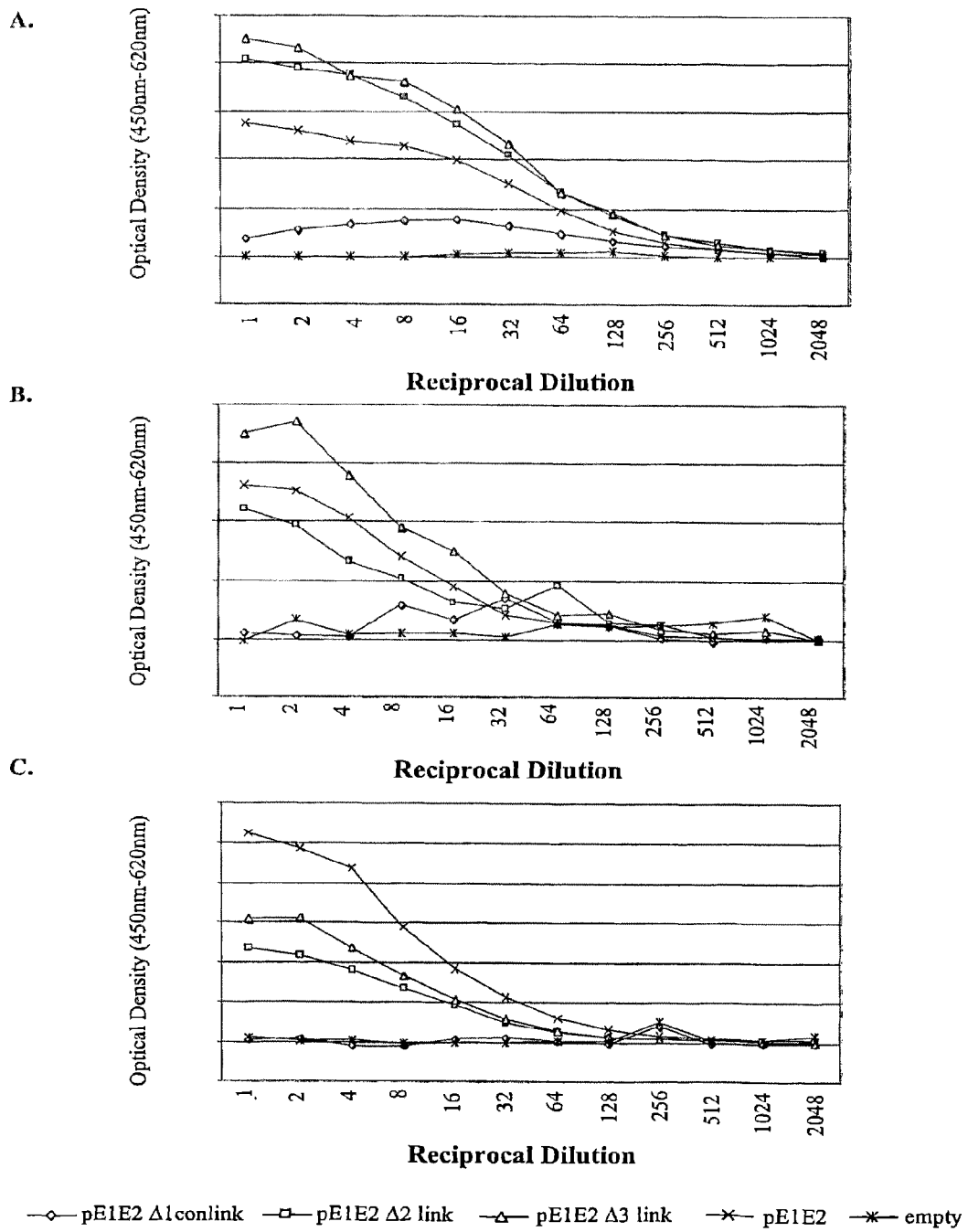
FIG. 9 shows the ability of E2 containing single modified deletions of one variable region to bind CD81-LEL. A. Metabolically-labelled cell lysates of 293T cells transfected with wild-type (pE1E2), pE1E2 containing a modified deletion of one variable region, or empty (pCDNA4) were applied to CD81 MBP-LEL (residues 113-201) coated enzyme immunoassay plates at progressive two-fold dilutions. Bound E2 was detected using the anti-E2 conformation-dependent monoclonal antibody H53 and rabbit anti-mouse horseradish peroxidase (HRP) conjugate. Absorbance values were read at 450 nm-620 nm (background). Data is representative of two independent experiments. B. Virion-incorporated E2 glycoprotein binding to CD81-LEL in viral lysates. Lysates of metabolically-labelled E1E2-pseudotyped HIV-1 particles were applied to CD81 MBP-LEL (residues 113-201) coated enzyme immunoassay plates at progressive two-fold dilutions and bound E2 was detected as described above. Absorbance values were read at 450 nm-620 nm (background) C. Independent repeat of B.

To examine whether the intracellular or virion-incorporated E2 glycoproteins containing these extended linkers altered CD81-LEL binding, both cell and viral lysates were applied to a solid phase CD81 MBP-LEL (residues 113-201) binding assay as previously described. This data was normalized for the amount of monomeric E2 expressed from each vector as precipitated with 1153 and observed by SDS-PAGE under non-reducing conditions; FIGS. 6D (intracellular) and 7A (virion incorporated). The extended linkers did not appear to alter the CD81-LEL binding ability of the intracellular E2 glycoproteins containing the HVR2link or "igVR link" deletions as they still demonstrated wild-type levels, or even slightly enhanced, binding as exhibited by the original HVR2 and "igVR" deletion constructs (FIG. 9A). Notably, the intracellular E2 glycoprotein containing the HVR1conlink deletion demonstrated a marginal recovery in CD81-LEL binding compared to the negative control (empty) suggesting that the conserved cysteine-proximal residues reintroduced into this construct may contribute directly or indirectly to the formation of the CD81-binding site. The virion-incorporated E2 glycoprotein containing HVR1conlink deletion, however, lost even this reduced CD81-LEL binding ability (FIG. 9B) consistent with its retarded incorporation into HIV-1 virions. The virion-incorporated E2 glycoproteins containing the HVR2link and "igVR link" deletion constructs maintained CD81-LEL binding in viral lysates, but generated inconsistent results in regard to their relative CD81-LEL binding ability across two independent assays (FIGS. 9B and 9C) and thus a third independent assay is required to verify these results.

Figure 10:
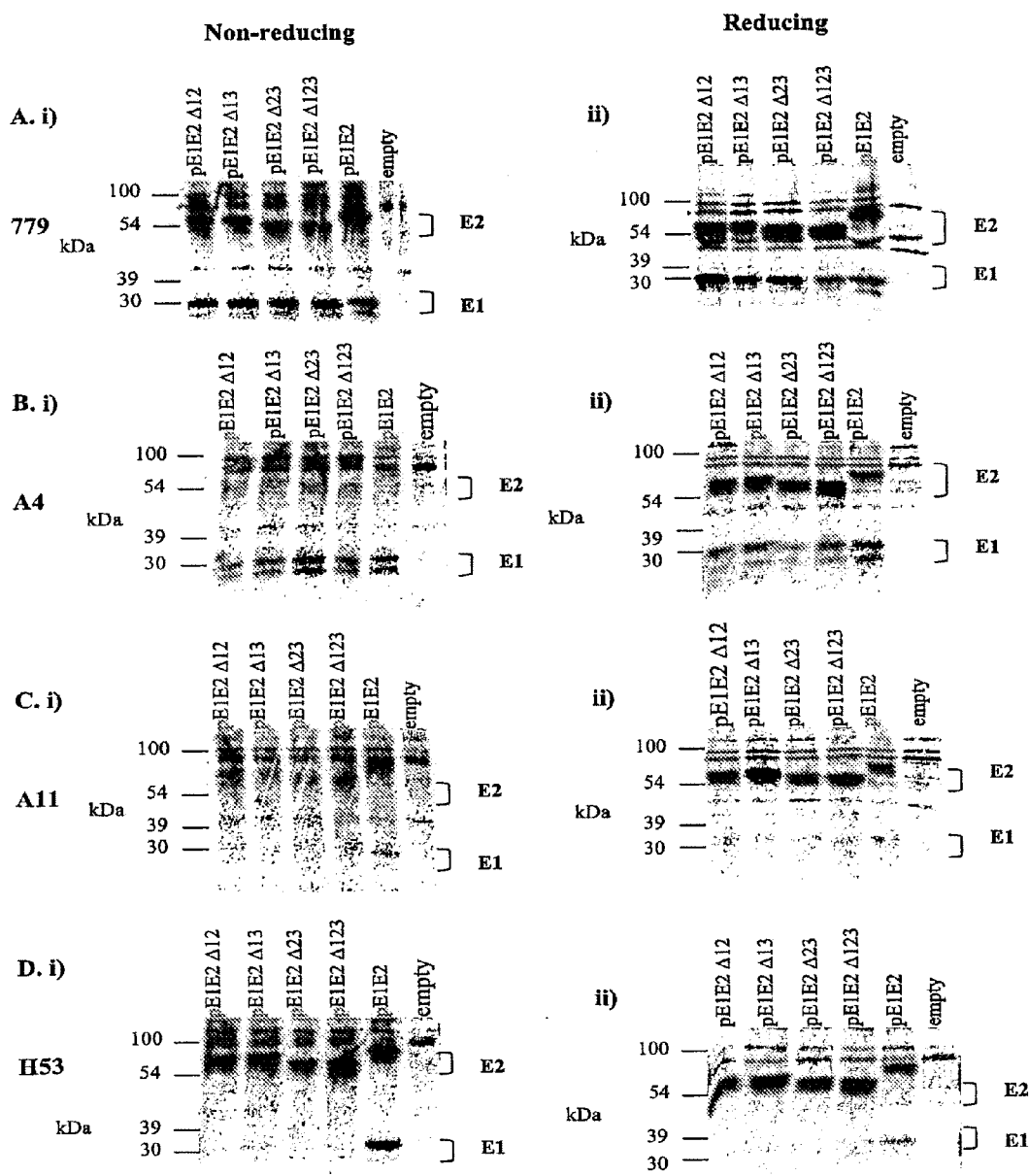
FIG. 10 shows the expression and heterodimerization of immature forms of E1E2 containing multiple variable region deletions. Metabolically-labelled cell lysates of 293T cells transfected with wild-type (pE1E2), pE1E2 containing multiple variable region deletions, or empty vector were immunoprecipitated with A. anti-E1E2 polyclonal antibody (779), B. anti-E1 monoclonal antibody (A4), C. anti-E2 monoclonal antibody (A11) and D. anti-E2 conformation-dependent monoclonal antibody (H53) under both i) non-reducing and ii) reducing conditions (+β-mercaptopethanol). All samples were run on 10-15% SDS-PAGE gradient gels and visualized using a phosphorimager. Data is representative of two independent experiments.

3. Effect of Multiple Variable Region Deletions on E1E2 Glycoprotein Structure and Function Intracellular E1E2 Precursor Folding and Heterodimerisation Despite a loss of heterodimerisation with E1 and/or viral entry, the above findings indicate that HVR1, HVR2 and "igVR" can be individually deleted from both the intracellular and virion-incorporated E2 glycoprotein without disrupting its intrinsic folding properties as recognised by the conformation-dependent monoclonal antibody H53 and binding to the large extracellular loop (LEL) of the CD81 receptor. In order to further characterise these variable regions and delineate a conserved E2 core domain, multiple deletions were introduced into the E1E2 polyprotein and analysed within 293T cells by pulse-chase metabolic-labelling and immunoprecipitation. Precipitation with the anti-E1E2 polyclonal antibody (779) showed efficient expression and cleavage of E1 (~30 kDa) and E2 (~70 kDa) glycoproteins from the polyprotein occurring for each of the multiple variable region deletion constructs (FIG. 10 A). These mutant E2 glycoproteins also migrated faster than the wild-type species corresponding to the loss of a glycosylation site within each HVR2 and/or "igVR" deletion: HVR1+2+igVR and HVR2+igVR<HVR1+2 and HVR1+igVR<WT. However, deglycosylation of these glycoproteins is required to confirm their backbone molecular weights as predicted in Table 3. The anti-E1 monoclonal antibody (A4) again detected an E1 doublet (~30 kDa and ~27 kDa) present for each of the variable region deletion constructs (FIG. 10B). E1 co-precipitated with both wild-type and mutant E2 glycoproteins under reducing conditions demonstrating the formation of covalently-linked E1E2 heterodimers. The failure to detect the wild-type E1E2 heterodimer under non-reducing conditions again reflects the low sensitivity of A4 for the non-covalently associated E1 glycoprotein.

In contrast, the non-conformation dependent anti-E2 monoclonal antibody (A11) did not detect the E2 glycoproteins containing these multiple variable deletions coprecipitating E1 under reducing or non-reducing conditions despite demonstrating wild-type levels of intracellular E2 glycoprotein expression for each of these deletion contructs (FIG. 10C). The conformation-dependent anti-E2 monoclonal antibody H53 also precipitated wild-type levels of the mutants E2 glycoproteins (FIG. 10D). This indicates that the inserted Gly-Ser-Ser-Gly linker motifs (SEQ ID NO: 95) provided sufficient flexibility within these mutant E2 glycoproteins to present this conformation-dependent epitope despite the introduction of multiple variable region deletions (FIG. 10D). These mutant E2 glycoproteins also demonstrated a loss of heterodimerisation with E1 consistent with the absence of HVR2 and/or "igVR" required in the assembly of the E1E2 heterodimer as observed above.

E1E2 Glycoprotein Maturation and Incorporation into Pseudotyped HIV-1 Particles

To examine whether the multiple variable region deletions altered E1E2 glycoprotein maturation, these deletions were introduced into E1E2-pseudotyped HIV-1 particles and lysed prior to immunoprecipitation with the conformation-dependent anti-E2 monoclonal antibody H53 and IgG from an HIV-1 infected individual (IgG14) as previously described.

Figure 11:
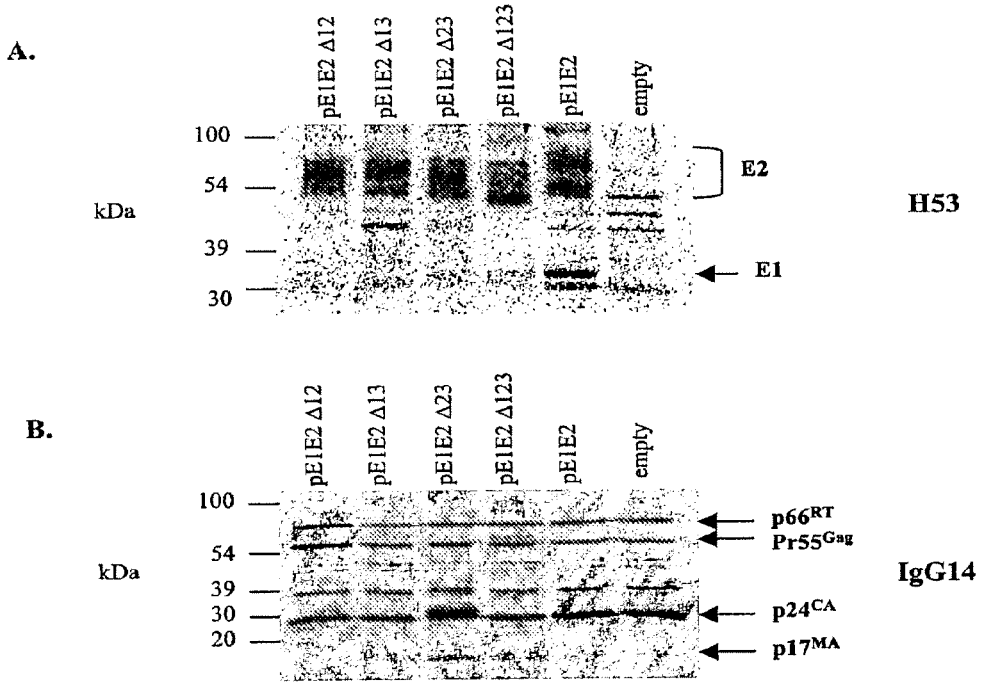
FIG. 11 shows the incorporation of E1E2 glycoproteins containing multiple variable region deletions into HCV glycoprotein-pseudotyped HIV-1 particles. Metabolically labelled E1E2-pseudotyped HIV-1 particles were pelleted from the tissue culture fluid of 293T cells co-transfected with NL4-3.LUC.R–E– and either wild-type (pE1E2), pE1E2 containing multiple variable region deletions, or empty vector prior to lysis. E1E2 heterodimers were immunoprecipitated with conformation-dependent anti-E2 monoclonal antibody H53. All samples were separated under non-reducing conditions on a 10-15% SDS-PAGE gradient gel and visualized using a phosphorimager. B. Processing and incorporation of HIV-1 structural proteins into HCV glycoprotein-pseudotyped HIV-1 particles. HIV-1 structural proteins $Pr55^{Gag}$, $p17^{MA}$, $p24^{CA}$ and $p66^{RT}$ from lysed metabolically-labelled E1E2-pseudotyped HIV-1 particles were immunoprecipitated using IgG from an HIV-1 infected individual (IgG14). Samples were separated under reducing conditions on a 7.5-15% SDS-PAGE gradient gel and visualized using a phosphorimager. Data is representative of two independent experiments.

IgG14 precipitation indicated that none of the multiple variable deletions had affected processing and virion incorporation of the HIV-1 structural proteins (FIG. 11 B). Immunoprecipitation with H53 again detected E2 as a diffuse band (~70-90 kDa) typical of the mature virion-incorporated E2 glycoprotein (FIG. 11A) and demonstrated the E2 glycoproteins containing multiple variable region deletions to be incorporated into HIV-1 virions at wild-type levels. These mutant E2 glycoproteins also migrated marginally faster than the wild-type species reflecting the loss of one or two glycosylation sites within the HVR2 and/or "igVR" deletions as described for the intracellular data. This suggests that the virion-incorporated E2 glycoproteins containing multiple variable region deletions retain the conformation-dependent H53 epitope even after maturation. Again, none of these mutant E2 glycoproteins co-precipitated detectable amounts of E1 as observed in the intracellular data.

E1E2-Mediated Entry into Huh7 Cells

Figure 12:
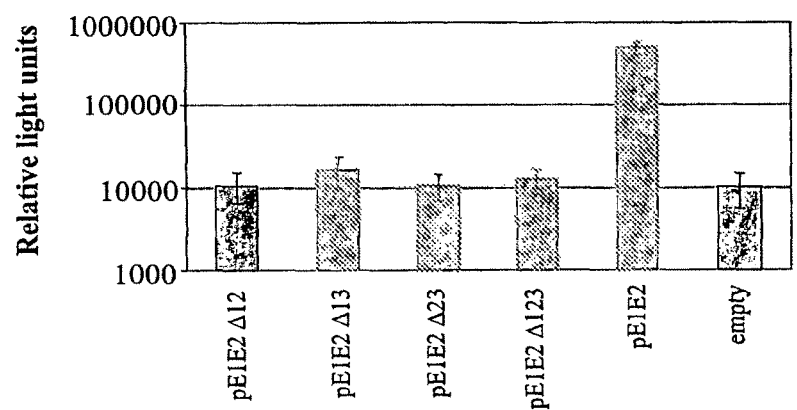
FIG. 12 shows the ability of E1E2-pseudotyped HIV-1 particles containing multiple variable region deletions to enter Huh7 cells. The tissue culture fluid from 293T cells co-transfected with the HIV-1 firefly luciferase vector (NL4-3.LUC.R–E–) and either wild-type (pE1E2), pE1E2 containing multiple variable region deletions, or empty (pCDNA4) vector was used to infect Huh7 cells in triplicate. The Huh7 cells were lysed and the luciferase activity measured using a Fluostar fitted with luminescence optics. The mean and standard deviation was calculated from triplicate infections. Data is representative of three independent experiments.

As expected, E1E2-pseudotyped HIV-1 particles containing multiple variable region deletions were not competent for entry into Huh7 cells (FIG. 12).

CD81-LEL Binding

Despite a loss of heterodimerisation and E1E2-mediated viral entry, both the intracellular and virion-incorporated E2 glycoproteins containing multiple variable region deletions were examined for their ability to bind CD81-LEL by applying both cell and viral lysates to a solid-phase CD81 MBP-LEL (residues 113-201) binding assay as previously described. This data was normalized for the amount of monomeric E2 expressed from each vector as precipitated with H53 and observed by SDS-PAGE under non-reducing conditions; FIGS. 10D (intracellular) and 11A (virion-derived).

The intracellular E2 glycoproteins containing multiple variable region deletions all demonstrated wild-type levels of CD81-LEL binding (FIG. 13A). This indicates that the Gly-Ser-Ser-Gly linker motifs (SEQ ID NO: 95) provide sufficient flexibility within these mutant E2 glycoproteins to form the precursor CD81 receptor-binding site. In addition, the E2 glycoprotein containing the HVR2 and "igVR" double deletion (pE1E2 Δ23) demonstrated a further enhancement of maximum CD81-binding across two independent experiments. This is consistent with this same effect observed in the individual HVR2 and "igVR" mutants although, similarly, the overall binding curve was not increased and thus additional independent assays are required to determine the statistical significance of this effect.

The virion-incorporated E2 glycoproteins containing multiple variable region deletions all maintained CD81-LEL binding (FIG. 13B) again indicating that the inserted linker motifs provide sufficient flexibility within these glycoproteins to present the CD81-binding site even after maturation. This again suggests that HVR1, HVR2 and "igVR" are not required for this function reflecting both the intracellular data and that obtained for the individual variable region deletions. Importantly, this demonstrates that the E2 glycoprotein containing the triple variable deletion encompasses all the structural and functional determinants required in CD81-LEL binding and thus constitutes a minimal E2 core domain. These virion-derived E2 glycoproteins containing double and triple variable region deletions also demonstrated slightly reduced or enhanced maximum CD81-LEL binding activity compared to wild-type, respectively, although again none of these mutants exhibited a significant increase in the overall binding curve.

4. Role of the Variable Regions in E2 Receptor-Binding Domain (E2 $RBD_{661myc}$) Structure and Function Folding and Secretion The above results demonstrate that the simultaneous deletion of all three variable regions does not disrupt the intrinsic folding of the E2 glycoprotein as recognised by the conformation-dependent monoclonal antibody H53 or binding to the CD81-LEL strongly suggesting that this construct constitutes an E2 core domain. However, in the context of the full-length E2 glycoprotein, the presence of both the transmembrane and membrane-proximal regions would make it difficult to crystallize this core E2 structure. Therefore, both single and multiple variable region deletions were introduced into E2 receptor-binding domain (E2 $RBD_{661myc}$) that is both soluble and amenable to high level expression. The E2 $RBD_{661myc}$ glycoproteins containing single and multiple variable region deletions were metabolically labelled within 293T cells and both the intracellular and secreted protein analysed by immunoprecipitation using the conformation-dependent anti-E2 monoclonal antibody (H53).

H53 precipitated wild-type levels of intracellular E2 $RBD_{661myc}$ (~50 kDa) for all single and multiple deletion constructs indicating that each of these mutant glycoproteins is efficiently expressed (FIG. 14A). These intracellular E2 $RBD_{661myc}$ glycoproteins also exhibited variably lower molecular weights than wild-type consistent with the loss of glycosylation sites located within the deleted regions as observed in the context of the full-length E1E2 heterodimer. However, deglycosylation of these truncated glycoproteins is required to confirm their molecular weights as predicted in Table 4. Furthermore, H53 precipitated a diffuse molecular weight band (~55-65 kDa) corresponding to the secreted form of the E2 $RBD_{661myc}$ (FIG. 14B) reflecting the various complex- and hybrid-type carbohydrate modifications acquired during transit through the secretory pathway. All E2 $RBD_{661myc}$ glycoproteins containing single and multiple variable region deletions were shown to be efficiently secreted and again displayed variable molecular weights (kDa) as described for the intracellular data. Together these results confirm that the variable regions can be deleted—individually and in combination—from the E2 $RBD_{661myc}$ and retain the intrinsic folding of both the intracellular and secreted receptor-binding domain as detected by the conformation-dependent anti-E2 monoclonal antibody H53.

CD81-LEL Binding

To determine whether the E2 receptor-binding domain containing single and multiple variable region deletions bind to CD81-LEL, both intracellular and secreted E2 $RBD_{661myc}$ lysates were applied to a solid-phase CD81 MBP-LEL (residues 113-201) binding assay as previously described. This data was normalized for the amount of monomeric E2 expressed from each vector as precipitated with H53 and observed by SDS-PAGE; FIGS. 14 A (intracellular) and 14B (secreted).

Both intracellular and secreted forms of the E2 $RBD_{661myc}$ containing the single variable region deletions demonstrated CD81-LEL binding although, as observed in the context of the full-length E2 glycoprotein, the HVR1con deletion conferred a total loss of CD81-LEL binding (FIGS. 15A and 15B). The secreted form of the E2 glycoprotein containing the single HVR1 deletion also exhibited an additional enhancement of CD81-LEL binding compared to wild-type consistent with the data obtained for the mature virion-derived forms of the full-length E2 glycoprotein. Importantly, both intracellular and secreted forms of the E2 $RBD_{661myc}$ containing the triple variable region deletion (HVR1+2+igVR) retained CD81-LEL binding at wild-type levels (FIGS. 16A and 16B) confirming that this glycoprotein species encompasses all the structural and functional CD81-binding determinants to constitute a minimal or near-minimal E2 core receptor-binding domain.

5. Binding of E2 $RBD_{661}$ Bearing Simultaneous HVR Deletions to Cell Surface Expressed Full-Length CD81.

Figure 17:
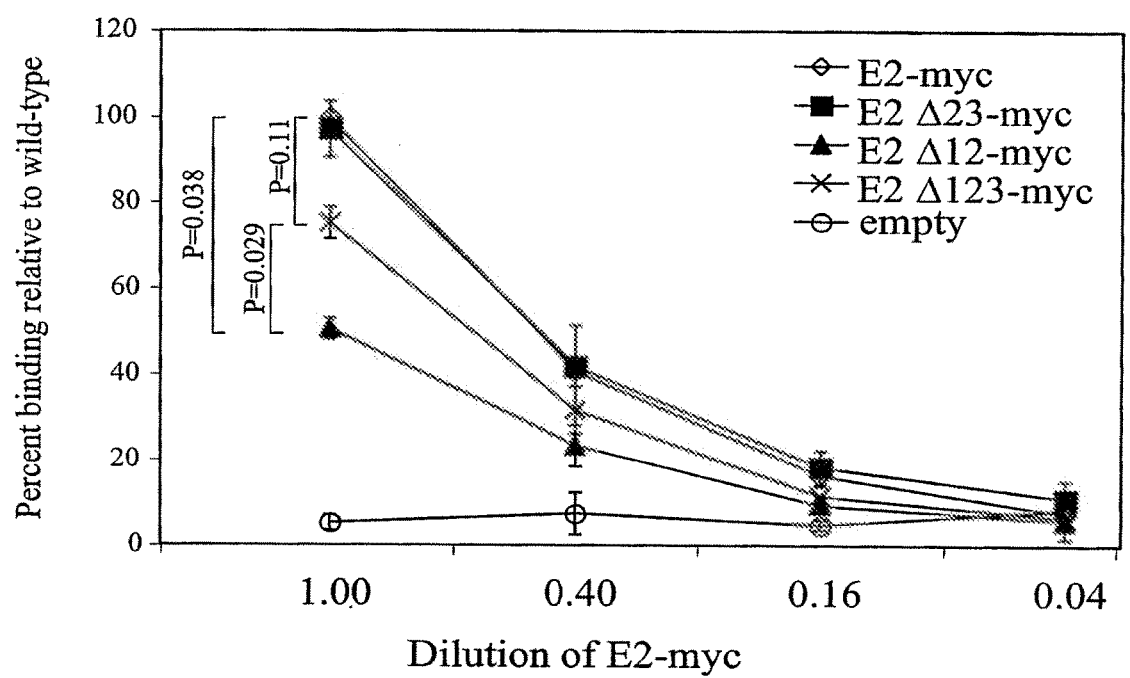
FIG. 17 shows the binding of E2-myc proteins to full length surface expressed CD81. Equivalent amounts of monomeric secreted E2-myc proteins produced from 293T cells were applied to CHO-K1 cells transfected with vector encoding full length CD81. Bound E2-myc was detected with iodinated 9E10 prior to measurement in a gamma counter. Mean of three independent assays±standard error. P values derived by comparison with the E2 Δ23-myc E2 construct using the students t test assuming unequal variances.

The abilities of secreted E2 $RBD_{661}$ proteins with multiple HVR deletions to bind cell surface expressed full length CD81 were determined. CHO-K1 cells were transfected with a vector encoding human CD81. Forty-eight hours after transfection, cells were placed on ice, and equivalent amounts of E2 added to cells. Four hours later, bound E2 was detected with radioiodinated MAb 9E10 and the amount of bound E2 quantitated. The results (FIG. 17) show that wild type and ΔHVR2+igVR-deleted E2 $RBD_{661}$ bound to full length CD81 at similar levels. By contrast, the binding of ΔHVR1+2-E2 $RBD_{661}$ to CD81 was significantly decreased (p=0.038); further deletion of igVR in construct E2 Δ123-myc restored wild type CD81 binding activity (p=0.11). These data indicate that the 3 variable regions can be deleted simultaneously without disruption to the CD81 binding ability of E2. Interestingly, simultaneous deletion of HVR1 and HVR2 from E2 $RBD_{661}$ led to decreased CD81 binding however this defect was rectified by further deletion of igVR.

6. Ability of E2 $RBD_{661}$ Bearing Simultaneous HVR Deletions to be Recognised by Human Conformation Sensitive Monoclonal Antibodies.

Figure 18:
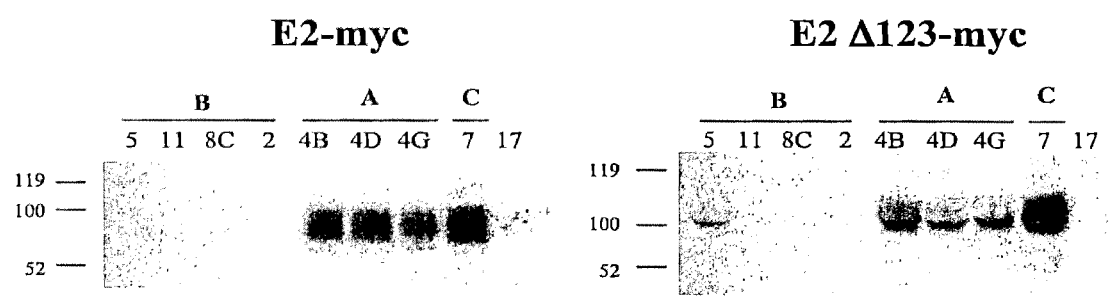
FIG. 18 shows the ability of E2-myc and E2 Δ123-myc to be detected with human conformation sensitive monoclonal antibodies. Wild-type (E2-myc) and E2 Δ123-myc were metabolically labelled and immunoprecipitated with the "CBH" panel of conformation dependent human monoclonal antibodies specific to three immunogenic domains (A, B and C) of E2. Immunoprecipitated proteins were analysed by SDS-PAGE under non-reducing conditions in 10-15% polyacrylamide gradient gels followed by scanning in a phosphorimager.

Wildtype E2-myc and E2 Δ123-myc was radiolabelled with $^{35}$S-Met/Cys and immunoprecipitated with a panel of human conformation sensitive monoclonal antibodies (Keck et al., 2004) and analysed by non-reducing SDS-PAGE. This panel of conformation-dependent MAbs are specific to conformational epitopes representing three distinct immunogenic domains of E2—A, B and C (Keck et al., 2004). The E2 Δ123-myc protein demonstrated a similar immunogenic profile to the wild-type E2-myc protein (FIG. 18) indicating that the E2-myc, lacking all three variable regions, retains the conformational epitopes specific to these three distinct structural and functional domains of E2. This data is consistent with previously published data by Keck et al. that also demonstrated a lack of HVR1 involvement in these domains (Keck et al., 2004). This data extends these observations to suggest that HVR2 and igVR also do not participate in these domains.

7. Discussion

In the course of this study, the two recognized E2 variable regions, HVR1 and HVR2, and the novel variable region "igVR" have been individually deleted to further investigate the role of these regions in E1E2 biosynthesis, heterodimerisation, CD81-binding and viral entry. All E2 glycoproteins containing these variable region deletions were shown to retain the intrinsic folding properties of the wild-type glycoprotein as recognized by the conformation-dependent monoclonal antibody H53. HVR2 and "igVR" were further shown to be required for heterodimerisation and all three variable regions were required in pre- or post-CD81-binding stages in viral entry. It has also been demonstrated that none of the individual variable regions are required for CD81-binding and that all three can be simultaneously deleted from the E2 glycoprotein with the retention of CD81-binding properties.

The envelope glycoproteins E1 and E2 exhibit the greatest genetic heterogeneity in the HCV genome, especially in hypervariable region 1 (HVR1)—a highly variable ~27 amino-acid sequence located at the N-terminus of the E2 glycoprotein. Here, it has been demonstrated that deletion of HVR1 (polyprotein residues 387-408) results in a loss of E1E2-mediated entry despite retaining both wild-type levels of heterodimerisation and incorporation of E1E2 into pseudotyped HIV-1 particles suggesting that this region has a direct role in viral entry. However, it has also been shown that HVR1 is not required for CD81-LEL binding in the context of either the functional E1E2 heterodimer or the E2 receptor-binding domain (E2 $RBD_{661myc}$) indicating that HVR1 is involved in another pre- or post-CD81-binding stage in viral entry. This is consistent with a previous study that has reported the deletion of HVR1 (polyprotein residues 384-410) to ablate E2 binding to the SR-B1 receptor suggesting that this region may be required for essential SR-B1 contacts in viral entry.

However, the present findings contradict several other studies that have demonstrated HCV pseudotyped particles (HCVpp) lacking HVR1 to mediate entry into Huh7 cells, although at reduced levels, inconsistent with an essential role for this region in viral entry. It has also been reported that the enhancement of HCVpp infectivity observed in the presence of the high density lipoprotein (HDL), a natural ligand of SR-B1, is lost upon the deletion of HVR1. This suggests that HVR1 facilitates infectivity rather than being essential for this function, although whether this effect is due to the association of HCV particles with HDL remains undetermined. In addition, a recent study has found that the substitution of all the conserved basic residues within HVR1 significantly reduces HCVpp entry although these residues were not found to be involved in either CD81-LEL binding or to correlate with an HDL enhancement of SR-B1 binding. Therefore the exact role of HVR1 in viral entry remains unclear.

It has also been shown that the deletion of HVR1 significantly enhances CD81-binding (approximately 4-fold) in agreement with previous studies. This suggests that HVR1 negatively modulates the accessibility of the conserved CD81-binding sites within the E2 glycoprotein despite not being required in this function. This is consistent with the recent identification of a conserved CD81-binding determinant $G^{436}$WLAGLFY (SEQ ID NO: 107) located between HVR1 and HVR2. In addition, the broadly neutralizing antibody AP33 has been demonstrated to recognise a conserved epitope directly adjacent to HVR1 (polyprotein residues 412-423) and to inhibit interactions between CD81 and a range of presentations of the E2 glycoprotein. The extension of the HVR1 deletion to include the conserved $I^{411}$ residue has also been shown to confer a reduction, rather than an enhancement, in CD81-binding further implicating this region in this function. Similarly, it has been demonstrated that the extension of the HVR1 deletion to include this adjacent conserved region (HVR1con, polyprotein residues 387-428) disrupts E2 glycoprotein folding and maturation critical in the formation of the CD81-binding site. Furthermore it has been demonstrated that residue $W^{420}$ located in this conserved region is also involved in CD81 binding The location of these highly conserved regions adjacent to HVR1, suggests that this highly variable region performs the dual function of both mediating viral entry and modulating the accessibility of these conserved regions to the host immune system to escape recognition by broadly neutralizing antibodies such as AP33. Indeed, a previous study has found that deletion of HVR1 results in an increased sensitivity of the envelope glycoprotein complex to neutralizing antibodies and sera. Therefore, it has been proposed that HVR1 forms a solvent-exposed subdomain external to a conserved core domain of the E2 glycoprotein consistent with both its modulating role in receptor-binding and its elicitation of an immunodominant response. In order to further characterise this proposed conserved core domain, the remaining E2 variable regions, HVR2 and "igVR"" have also been deleted. As observed for the HVR1 deletion, both E2 glycoproteins lacking the individual HVR2 and "igVR" regions retained the intrinsic folding properties of the wild-type glycoprotein as detected by the conformation-dependent monoclonal antibody H53.

Interestingly, however, both HVR2 and "igVR" were shown to be required for heterodimerisation and, accordingly, the deletion of these regions demonstrated a total loss of E1E2-mediated entry in to Huh7 cells. This suggests that these regions within the E2 glycoprotein are involved in direct heterodimer contacts or, alternatively, modulate allosteric effects that are indirectly required for this function. Therefore to further investigate the role of these regions, several conserved cysteine-proximal residues were reintroduced into the HVR2 and "igVR" deletion constructs affecting to extend their linker motifs and thus enhance E2 glycoprotein folding. The extension of the "igVR" linker was found to recover wild-type levels of heterodimerisation with E1 and a significant level of E1E2-mediated entry (~8-fold) although this effect was not observed for HVR2. This finding may reflect the relatively short length of the "igVR" deletion where two of the five glycine residues lost from this region are further compensated for by the introduction of the Gly-Ser-Ser-Gly linker motif (SEQ ID NO: 95) resulting in only a five amino-acid total deletion within this region. The role of the "igVR" linker in heterodimerisation is also consistent with its observed conservation within genotypes. Notably, the extended "igVR" linker construct still exhibited a reduction in entry activity compared to wild-type (~10-fold) and is perhaps due to absence of a conserved N-linked glycosylation site within this region that has been previously observed to reduce HCVpp entry.

Furthermore, it has been demonstrated that the E2 glycoprotein containing either the HVR2 or "igVR" deletions retains wild-type levels of CD81-binding indicating that these regions, as observed in HVR1, are not required in this function. Previous studies have shown that monoclonal antibodies targeting HVR2 inhibit E2 glycoprotein binding to CD81 and proposed that this region forms a CD81-binding determinant although, based on the present findings, it is more likely that these antibodies are creating a steric effect that occludes the G $^{436}$WLAGLFY (SEQ ID NO: 107) CD81-binding determinant adjacent to this region. Therefore, despite a loss of heterodimerisation and/or viral entry, HVR1, HVR2 and "igVR" can all be individually deleted from the E2 glycoprotein without disrupting its intrinsic folding properties and, indeed, it has been further shown that all three variable regions can be simultaneous deleted with a retention of CD81-binding. This strongly supports the hypothesis that these variable regions form solvent-exposed subdomains external to an E2 core domain encompassing the conserved structural and functional determinants required for binding to the confirmed HCV receptor, CD81.

Interestingly, it has also been observed that the E2 glycoproteins containing the HVR1 deletion in combination with either HVR2 or "igVR" deletions did not exhibit the dramatic enhancement in CD81-LEL binding observed for the individual HVR1 deletion. A previous study has demonstrated that the substitution of HVR1 and HVR2 with corresponding sequences from a different subtype in combination achieves either increased or decreased CD81 binding (depending on the introduced and backbone strains) that is not observed for either of the individual HVR1 or HVR2 substitutions. Together this data suggests that intramolecular interactions are occurring between these regions to modulate CD81-binding and that they are likely to adopt intrinsically flexible structures to entertain these contacts. This is further supported by both the recent identification of a conserved CD81-binding determinant G$^{436}$WLAGLFY$^{443}$ (SEQ ID NO: 107) located directly between HVR1 and HVR2 as well as the immunodominant responses elicited by both HVR1, and to a lesser extent, HVR2 consistent with their position as surface-exposed subdomains that may perform modulating functions in cell attachment. This same effect observed for the HVR1 and "igVR" double deletion suggests that the "igVR" region may also contribute to these cooperative interactions.

One hypothesis to explain this data, proposes that the variable regions form flexible solvent-exposed subdomains that enable the E2 glycoprotein to move between 'open' and 'closed' conformations, the former being more competent for CD81 binding by exposing the conserved CD81-binding determinants located within the core E2 domain as delineated within this study. Indeed, conformational changes within the E2 glycoprotein have been previously observed upon CD81-binding. In addition, binding of non-neutralizing antibodies to the E2 glycoprotein has been demonstrated to reduce its susceptibility to neutralizing antibodies and is consistent with a model where the non-neutralizing antibodies inhibit the flexibility of these surface-exposed variable regions thus blocking access to the conserved epitopes located within the E2 core domain. Therefore, this suggests that the modified E2 core domain represents a promising vaccine candidate for eliciting neutralizing antibodies to conserved epitopes within the E2 glycoprotein, including the CD81-binding determinants, that are otherwise occluded by these surface-exposed variable regions that may act as immunological decoys at the surface of the glycoprotein complex during HCV replication.

The observed loss of heterodimerisation in the E2 glycoproteins containing HVR2 and "igVR" deletions suggests that conformational changes are occurring within these glycoproteins that cannot be recognised by the single conformation-dependent monoclonal antibody H53. Therefore, a panel of conformation-dependent antibodies that have been previously used to identify the three major immunogenic regions within the E2 glycoprotein were obtained to examine more subtle alterations in glycoprotein structure and function mediated by these variable regions. The results show that in the context of E2 RBD$_{661myc}$ monoclonal antibodies to domain A, B and C retain wild-type levels of reactivities to the RBD containing simultaneous deletion of all three variable regions. This further suggests that the E2 Δ123-mycΔ123RBD construct retains the intrinsic core domain folding properties of the native E2 RBD.

Figure 19:
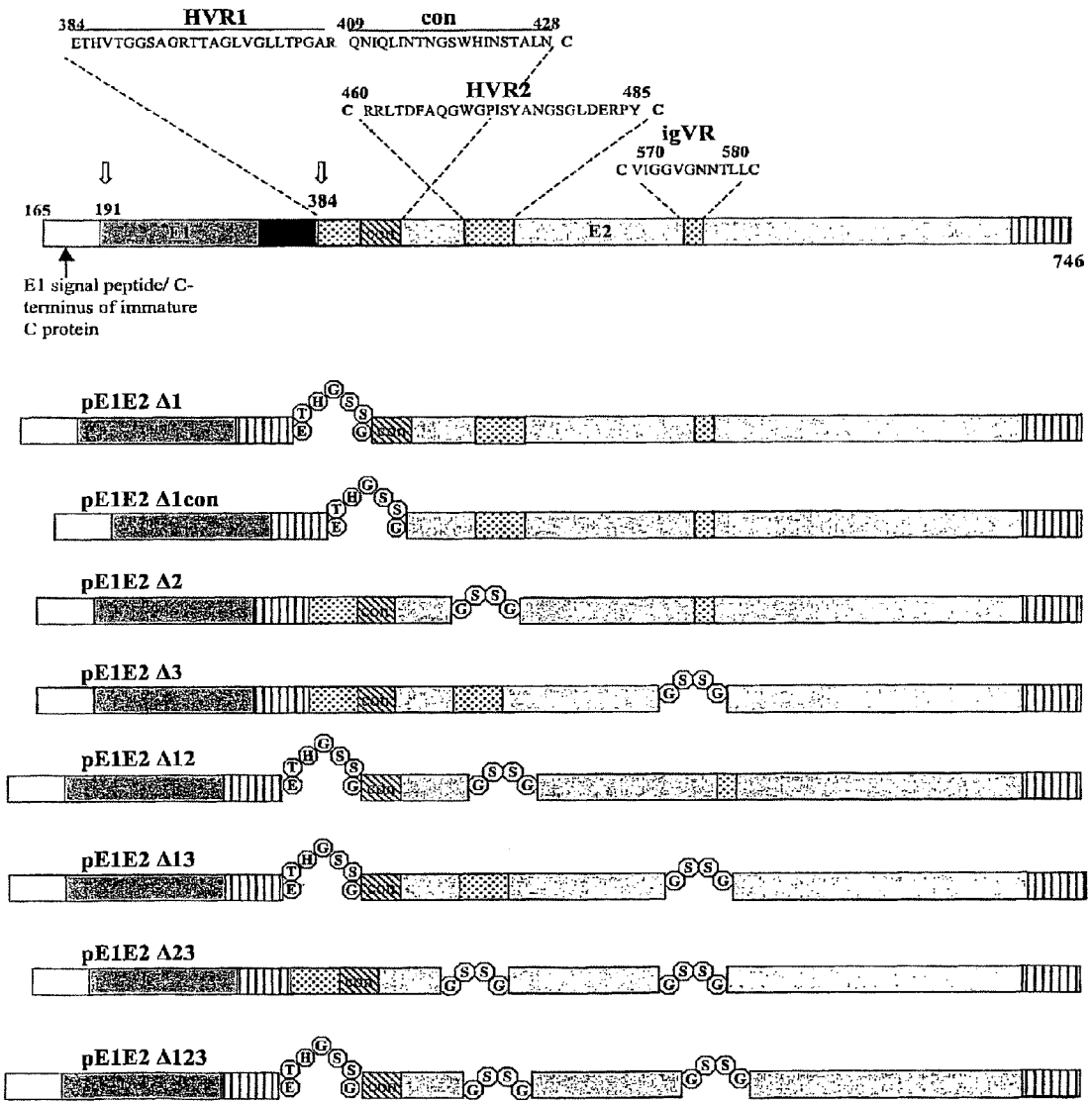
FIG. 19 shows a schematic representation of the E1E2 polyprotein containing single and multiple variable region deletions. The pE1E2 vector encodes the full-length H77c sequence of E1 (dark grey) and E2 (light gray) including their transmembrane domains (horizontal stripes) at the C-terminus of E1 and E2 and the signal peptides with the signal peptidase cleavage sites indicated (arrows). The E2 variable regions (dotted) and the conserved region adjacent to HVR1 (diagonal stripes) are replaced—individually and in combination—with flexible Gly-Ser-Ser-Gly (GSSG) linker motifs (SEQ ID NO: 95) as indicated.

8. Materials and Methods
Construction of the Variable Region Deletion Mutants Vectors In order to introduce the E2 variable region deletions into the E1E2 heterodimer, the HCV-based expression vector pE1E2H77c was obtained (Drummer et al., 2003). The pE1E2H77c vector contains a DNA sequence from the full length pCV-H77c (genotype 1a) infectious clone (Yanagi et al., 1997) encoding the E1E2 polyprotein residues 165-746 as described (Drummer et al., 2003). To ensure efficient ER targeting and glycoprotein cleavage, this sequence includes the E1 signal peptide located at the C-terminus of the immature core protein and both the full-length E1 and E2 polyprotein sequences (FIG. 19). This DNA fragment was cloned into the backbone of the pCDNA4HisMax vector (Invitrogen, Carlsbad, Calif., USA) that contains both a translational enhancer sequence and a cytomegalovirus (CMV) promoter for expression in mammalian systems. It also contains an ampicillin resistance gene for selection in bacterial cells.

The CD81 open reading frame was amplified by PCR from pcDM8-TAPA-1 (Levy et al., 1998)30) using the primers, 5'-CCGAAGCTTCCACCATGGGAGTG-GAGGGCTGC-3' and 5'-GGCTCTAGATTAGTACACG-GAGCTGTTCCG-3'. The PCR product was cloned into pcDNA3 using HindIII and XbaI (shown in bold type) to generate the plasmid pcDNA3-CD81.

To enable characterisation of the variable regions within the soluble E2 receptor-binding domain (E2 RBD$_{661}$), the HCV-based expression vector pE2661 was also obtained (Drummer et al., 2002). The pE2661 vector contains a pCV-H77c DNA sequence encoding HCV polyprotein residues 384-661 as described (Drummer et al., 2006)2002). This sequence encodes an independently folding subdomain of the E2 glycoprotein that has been shown to retain both CD81 and SR-B1 receptor-binding (Pileri et al., 1998, Scarselli et al., 2002, Pileri et al., 1998). This DNA product was cloned into a pCDNA3 vector (Invitrogen) backbone at the C-terminus of a tissue plasminogen-activator (tpa) leader sequence designed to ensure efficient ER targeting and signal cleavage of the E2 RBD$_{661}$ in the absence of E1 (E2-myc). This vector also contains a CMV promoter for expression in mammalian cells and an ampicillin resistance gene to facilitate selection in bacterial cells.

Overlap Extension PCR

Overlap extension PCR is a two step strategy that facilitates the deletion of large segments of DNA (FIG. 20) (Horton et al., 1989). In round one, the pE1E2H77c vector was used as a template to introduce individual variable region deletion into the full-length E1E2 polyprotein. This step required two oligonucleotide pairs (Geneworks, Ann Arbor, Mich., USA); each pair containing one external and one internal primer responsible for amplifying the sequence either upstream (5') or downstream (3') of the variable region. The internal oligonucleotide primers were designed to introduce the Gly-Ser-Ser-Gly linker (SEQ ID NO: 95) as well as a short overlap sequence complementary to the corresponding 5' or 3' fragment (Table 5). Once generated, these first round 5' 3' PCR products were isolated by agarose-gel electrophoresis and purified prior to being added to the second round PCR reaction. Round two allowed annealing of the 5' and 3' fragments via their overlapping, complementary sequences to form a template for extensions and amplification by the relevant external primers. The external primers also contained unique EcoR1/Xba1 restriction endonuclease sites to facilitate cloning back into the template vector.

E1E2 Variable Region Deletion Constructs

Figure 20:
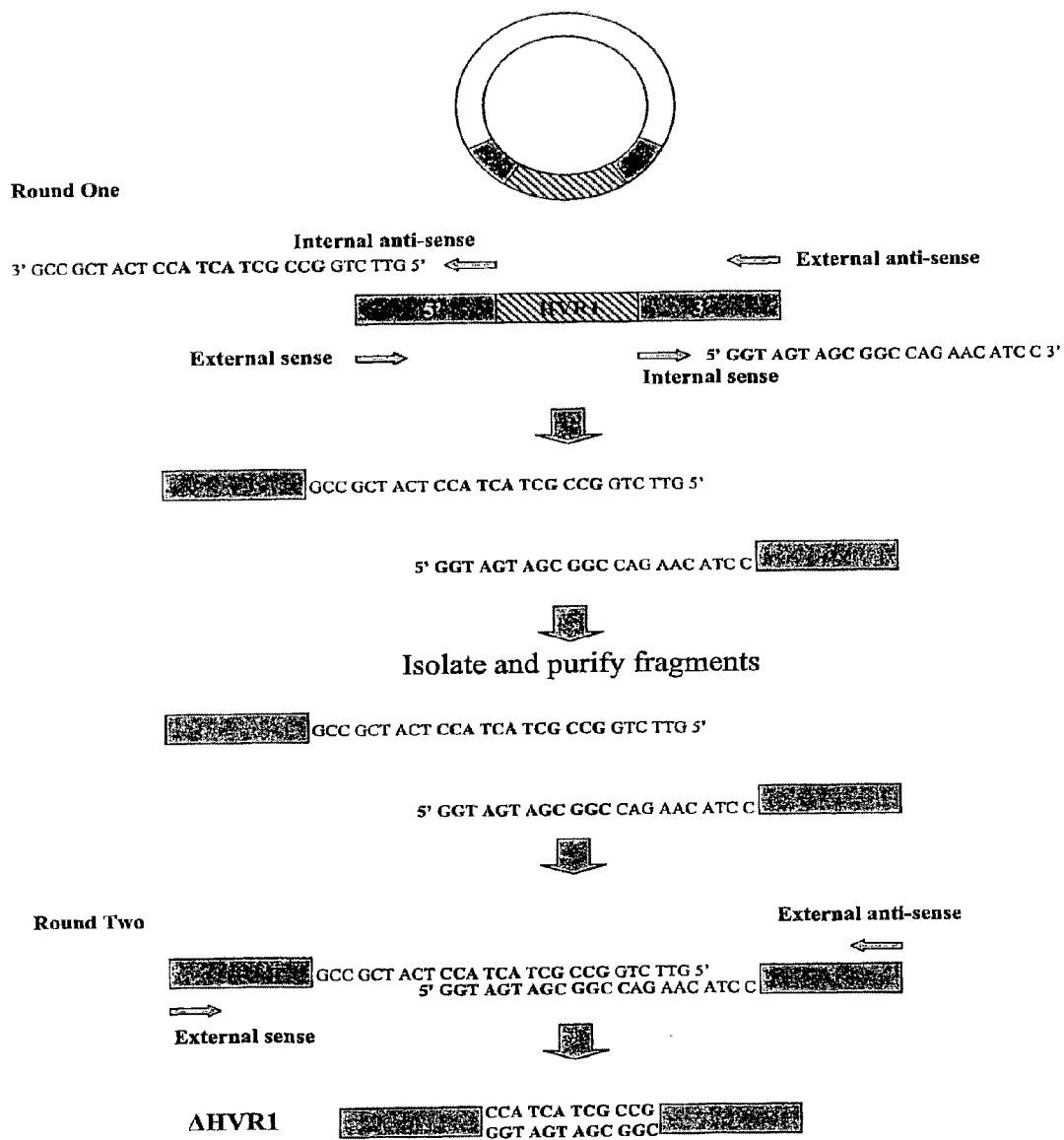
FIG. 20 shows a schematic representation of overlap extension PCR strategy. The variable regions were deleted from the HCV glycoprotein template sequence (diagonal stripes) using two oligonucleotide pairs: each contains one external and one internal primer that amplifies either the 5' or 3' fragment adjacent to HVR1 as shown. The internal primer sequence introduces the Gly-Ser-Ser-Gly linker motif (bold) (SEQ ID NO: 95) and a short 'overlap' sequence complementary to the respective 5' or 3' fragment. These sequences anneal to form the template for the second round of PCR amplification that uses the external primers to amplify the HVR1 deleted glycoprotein sequence.

The overlap extension PCR strategy was used to generate the single variable region deletions as summarized in Table 5 and represented in FIG. 20. Notably, two alternative HVR1 deletion constructs, HVR1 and HVR1con, were designed to further investigate this region. The HVR1 deletion lacks the highly variable segment between polyprotein residues 387 and 408, whereas HVR1con extends this deletion to encompass the adjacent region up to the first conserved cysteine residue in E2 (polyprotein residues 387-428) proposed to anchor this N-terminal region to the rest of the glycoprotein. The first three amino-acids ($E^{384}$TH) of HVR1 were also retained in these constructs to ensure efficient cleavage between E1 and E2 during glycoprotein biosynthesis. HVR2 and "igVR" deletions encompassed polyprotein residues 460-485 and 570-580, respectively.

Figure 21:
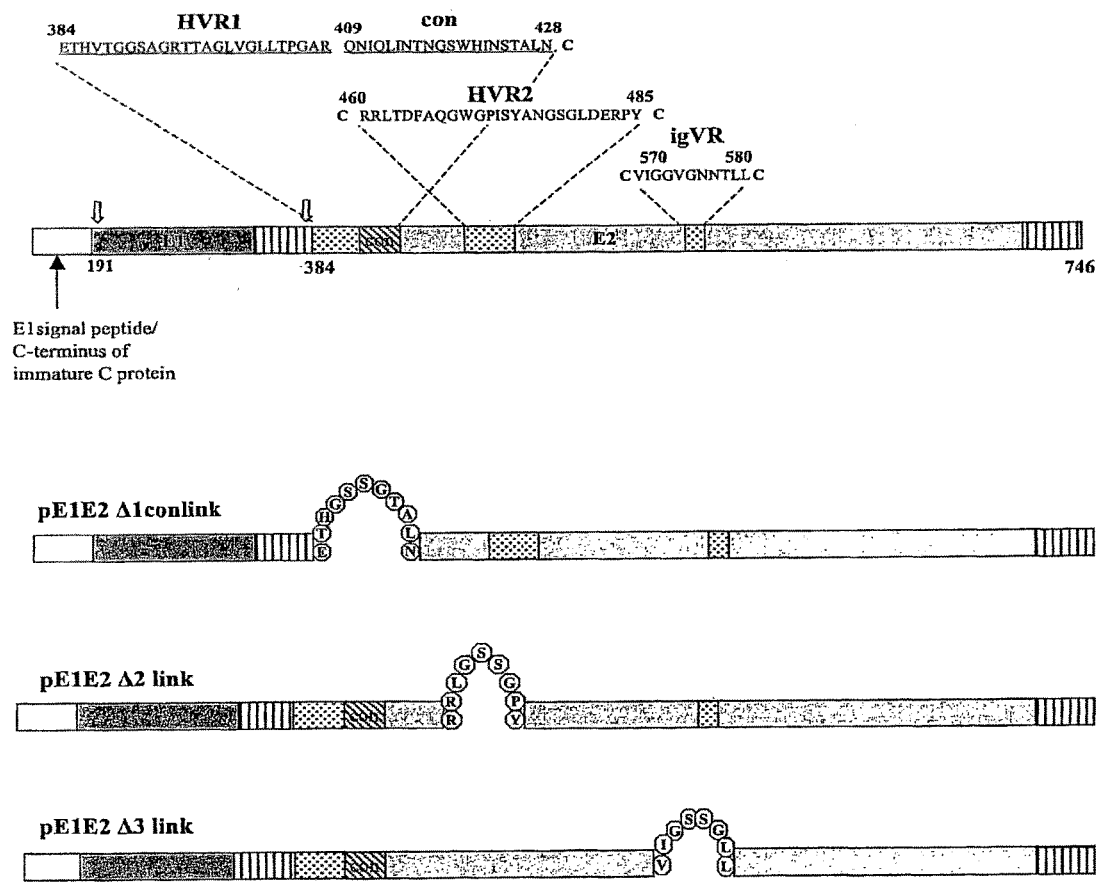
FIG. 21 shows a schematic representation of HCV E1E2 polyprotein containing modified single variable region deletions with extended linkers. The pE1E2 vector encodes the full-length H77c sequence of E1 (dark gray) and E2 (light gray) including their transmembrane domains (vertical stripes) at the C-terminus of E1 and E2. The signal peptidase cleavage sites are also indicated (arrows). The E2 variable regions and the conserved region adjacent to HVR1 (con) are partially deleted and replaced with flexible Gly-Ser-Ser-Gly linker motifs (SEQ ID NO: 95).

To enhance E2 glycoprotein folding, a second series of modified single variable region deletion constructs were generated using overlap extension PCR (FIG. 21). This strategy utilized a set of modified internal oigonucleotide primers to extend Gly-Ser-Ser-Gly linker motif (SEQ ID NO: 95) by reintroducing several conserved cysteine-proximal residues deleted from the original constructs and summarized in Table 2 and represented in FIG. 21. Notably. this modified ΔHVRlink E1E2 series lacks a HVR1 deletion construct due to the lack of any conserved residues located within this region.

In order to delineate a minimal E2 core domain, multiple HVR1, HVR2 and "igVR" deletions were introduced into the context of the E1E2 polyprotein as represented in FIG. 19. These multiple deletion constructs were again generated using overlap extension PCR, but utilized the relevant single or double variable region deletion constructs a template instead of the wild-type pE1E2H77c vector as outlined in Table 3.

E2 RBD$_{661myc}$ Variable Region Deletion Constructs (E2-myc)

Figure 22:
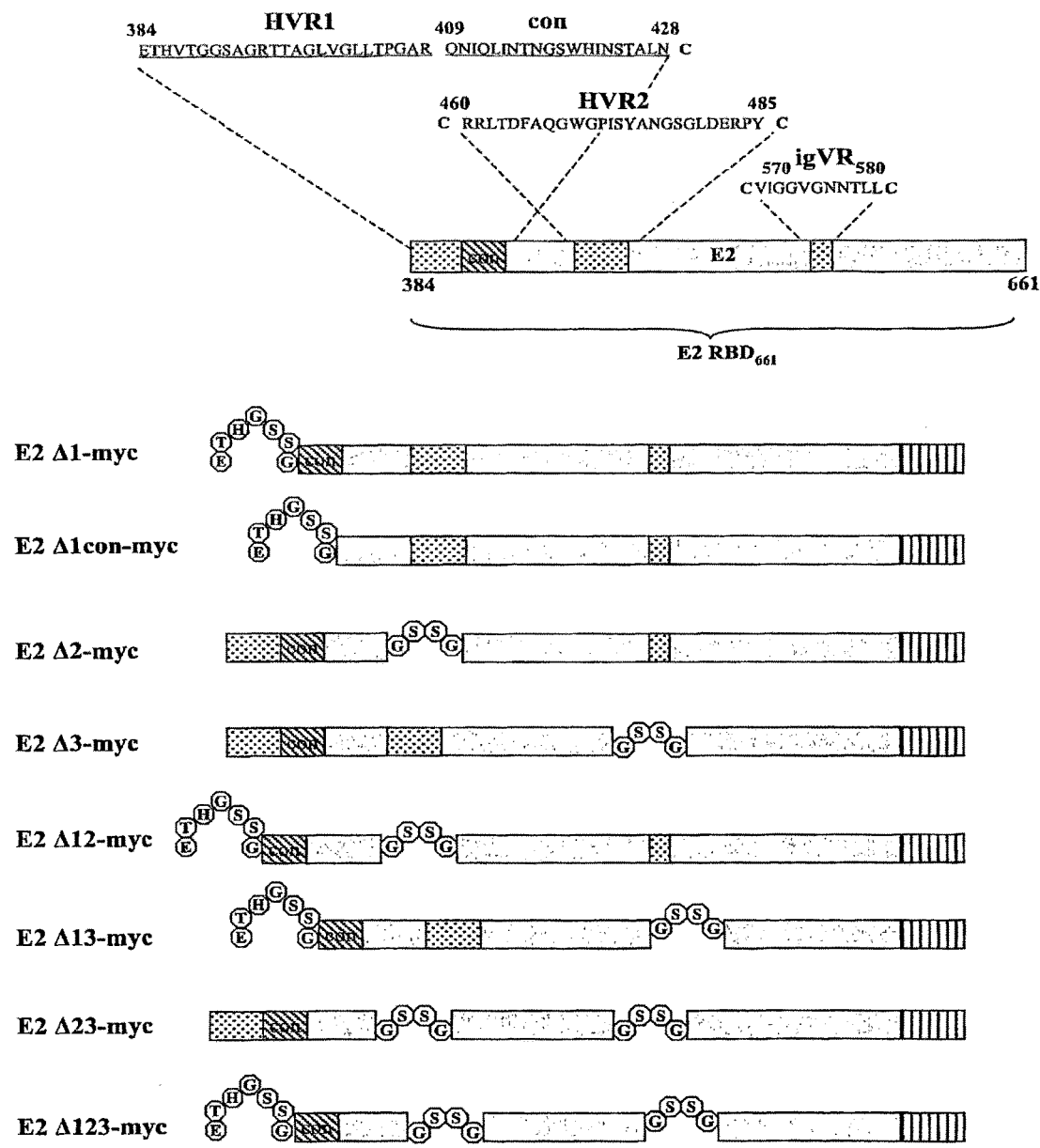
FIG. 22 shows a schematic representation of the E2 receptor-binding domain (E2 RBD$_{661}$) containing single and multiple variable region deletions. The pE2661 vector encodes the E2 RBD encoding residues 384-661 (E2-myc). The variable regions (dotted) and a conserved sequence adjacent to HVR1 (diagonal stripes) were replaced individually and in combination with short flexible Gly-Ser-Ser-Gly (GSSG) linker motifs (SEQ ID NO: 95) as indicated. A myc epitope tag (vertical stripes) was also introduced at the C-terminus of these constructs.

In order to characterise the single and multiple variable region deletions in the context of the soluble E2 receptor-binding domain (E2 RBD$_{661myc}$), standard PCR was used to amplify polyprotein residues 384 to 661 from the full-length E1E2 constructs containing the single and multiple variable region deletions as outlined in Table 4 and represented in FIG. 22. The oligonucleotide primers were designed to introduce a C-terminal myc epitope tag and unique NheI/XbaI restriction endonuclease sites to facilitate the cloning of these PCR products into the pE2661vector.

All PCR reactions were carried out in the Biometra Thermocycler (Biometra, Goettingen, Germany) using the Expand High Fidelity PCR system (Invitrogen) under the conditions summarized in Table 6.

Agarose-Gel Electrophoresis

DNA products were isolated by agarose-gel electrophoresis using Bio-Rad gel tanks (Bio-Rad Laboratories, Hercules, Calif., USA) containing TAE (0.001M EDTA and 0.04M Tris-Acetate). 1% (w/v) DNA-grade agarose in TAE was made up with ethidium bromide (0.5 µg/mL) to enable DNA visualization under UV light (Sambrook and Russel, 2001). DNA samples were made up at 20% (v/v) with Orange G gel-loading dye (1% (w/v) Orange G (Sigma, St Louis, Mo., USA), 50% (v/v) glycerol). Agarose gels were run at 100V, 23 mA for 30-40 min and DNA fragment size was confirmed and quantified using the GelDOC system (Bio-Rad) in reference to a 1 kb Plus DNA Marker (Invitrogen). Confirmed DNA products were subsequently purified from PCR reactions using the Mo Bio PCR Clean-up kit (Mo Bio, Carlsbad, Calif., USA) or from agarose gels with the Mo Bio Gel-Spin kit (Mo Bio) according to the manufacturer's instructions.

Restriction Endonuclease Digestion of DNA

All DNA was digested with New England Biolabs restriction endonucleases according to the manufacturer's instructions (New England Biolabs, Ipswich, Mass., USA). Any digested vectors were de-phosphorylated with Shrimp Alkaline-phosphatase (Invitrogen) for 30 min at 37° C. to reduce self-annealing.

Ligation and Transformation of Plasmid Constructs

Digested insert and vector DNA were ligated together at approximately a 4:1 ratio using the T4 DNA-ligase system (Invitrogen) and incubated at 4° C. for 16 hrs. DNA ligation products were isolated using the sodium-acetate precipitation method (3M Na-Acetate pH 5 and 100% Ethanol) (Sambrook and Russel, 2001) and resuspended for 1 hr in sterile distilled water. Ligation products were transformed into 20 uL of electroporation-competent DH10B E. coli cells (New England Biolabs) using 1 mm electroporation cuvettes (BTX, Holliston, Mass., USA) and a Gene Pulser Electroporator (BioRad) set at 2.0V, 200Ω and 25 µF. The electro-treated DH10B cells were then transferred into Luria Bertani Medium (LB) (1% (w/v) Tryptone, 0.5% (w/v) Yeast Extract, 0.5% (w/v) NaCl) to recover for 1 hr at 37° C. The cells were then spread-plated out onto LB-Agar plates (LB, 5% (w/v) Agar) containing 50 ug/mL ampicillin and incubated at 37° C. for 16 hrs to select for transformed cells (Sambrook and Russel, 2001).

Colony PCR

In order to rapidly screen for transformed colonies containing the desired DNA insert, approximately 20 colonies were selected from each LB-Agar plate for colony PCR (Sambrook and Russel, 2001). Colony PCR was performed using the Taq polymerase system (Invitrogen) and the appropriate external primers in the Biometra Thermocycler (Biometra) under the conditions specified in Table 6. The colonies containing positive inserts were identified by agarose-gel electrophoresis as described above.

Small-Scale Preparation of Plasmid DNA

Small-scale preparations of plasmid DNA from positive colonies were then generated using the Mo Bio Mini-prep kit (Mo Bio) using the alkaline lysis method in accordance with the manufacturer's specifications. Inserts were confirmed by restriction endonuclease digest and agarose-gel electrophoresis as described above.

DNA Sequencing

The sequences of all plasmid DNA inserts were confirmed using the relevant sequencing primers and the PRISM BigDye Terminator Mix (version 3.1) (Applied Biosystems, Foster City, Calif., USA) according to the Micromon Reaction Set-Up Protocol (Micromon, Victoria, Australia). All sequencing reactions were run in a Biometra Thermocycler (Biometra) under the conditions outlined in Table 6 and the resulting DNA prepared according to the Micromon Reaction Clean-Up Protocol (Micromon). Sequence analysis was performed in a 3730S Genetic Analyser (Applied Biosystems) at the Micromon sequencing facility.

Large-Scale Preparation and Quantification of Plasmid DNA

Plasmid DNA from confirmed clones was then isolated on a larger scale using the Qiagen Midi-prep Kit (Qiagen, Hilden, Germany) based on the alkaline lysis method in accordance with the manufacturer's specifications. These large scale plasmid DNA preparations were purified using phenol-chloroform (1:1) and centrifuged at 10 000×g for 3 min to obtain an upper phase containing the DNA and repeated with chloroform (50% (v/v)). Purified DNA was concentrated using sodium-acetate (10% (v/v) and 2.5 volumes of 100% ethanol at 70° C. for 30 min. DNA was pelleted at 10 000×g for 15 mins prior to washing twice in 70% precipitation method and resuspended in 100 uL of TE. All DNA concentrations were determined using a Biophotometer at 260 nm (Eppendorf, Hamburg, Germany).

During this study, all bacterial work utilised an orbital-shaker (Ratek Instruments, Victoria, Australia) or an incubator (Memmet, Schwabach, Germany) set at 37° C.

Biochemical and Functional Assays

Cell Culture 293T human embryo kidney cells (HEK 293T) from a human fibroblast cell line was used in this study to ensure high transfection efficiency and to achieve good levels of cellular protein expression. The human liver hepatocyte is the primary target cell for HCV and thus the human hepatocellular carcinoma cell line, Huh7, was used as a model liver cell system in this study. Furthermore, the Huh7 cell line has been demonstrated to support subgenomic HCV replicons, is highly permissive to HCVpp entry and can support cell culture grown HCV (HCVcc) suggesting that it contains all the cellular factors required for HCV tropism in vivo (ZhongBartosch et al., 2005, Wakita et al., 20052003a, Lindenbach et al., 2005b, Lohmann et al., 1999, LindenbachWakita et al., 2005a, Zhong et al., 2005, Bartosch et al., 2003a).

All cells were maintained in DMF10: Dulbecco's minimal essential medium (Invitrogen), 10% (v/v) heat-inactivated foetal bovine serum (Invitrogen), 2 mM L-glutamine (GE Healthcare, Bukinghamshire, UK), 1M HEPES buffer solution (Invitrogen), Gentamycin (GE Healthcare) and 2 ug/mL minocycline-hydrochloride salt (Sigma). The cells were subcultured every 3-4 days in 75 cm$^2$ or 150 cm$^2$ Falcon flasks (Becton Dickenson, Franklin Lakes, N.J., USA) using 0.025% (v/v) Trypsin in PBS-EDTA (phosphate buffered saline (PBS)-ethylenediaminetetraacetic acid (EDTA)) to detach the monolayer. All cells were incubated in a Thermo Direct Heat $CO_2$ incubator at 37° C. with 5% $CO_2$ (Thermo, Waltham, Mass., USA). During this study, all vectors were transfected into HEK 293T cells seeded in 6-well culture dishes (Nalge Nunc, Rochester, N.Y., USA) using the FuGene6 transfection reagent (Roche) as previously described (Drummer et al., 2003).

Antibodies

The non-conformational anti-E1 monoclonal antibody A4 and non-conformational anti-E2 monoclonal antibody A11 were gifts from Drs. Jean Dubuisson and Harry Greenberg (Dubuisson et al., 1994). The anti-E2 conformation-dependent monoclonal antibody, H53, was also a gift from Dr. Jean Dubuisson (Deleersnyder et al., 1997). The anti-E1E2 polyclonal antibody, 779, purified from the plasma of an HCV genotype 1a-infected individual was obtained (Drummer and Poumbourios, unpublished). Immunoglobulin G from an HIV-1 infected individual (IgG14) and the anti-myc monoclonal antibody 9E10 were also obtained (Drummer et al., 2002, Drummer et al., 2003). A panel of conformation-dependent human MAbs, specific to conformational epitopes representing three distinct immunogenic domains of E2 A, B and C, were obtained from Dr. Steven Foung (Keck et al., 2004).

E1E2 Pseudotyped HIV-1 Particle Entry Assay

Figure 23:
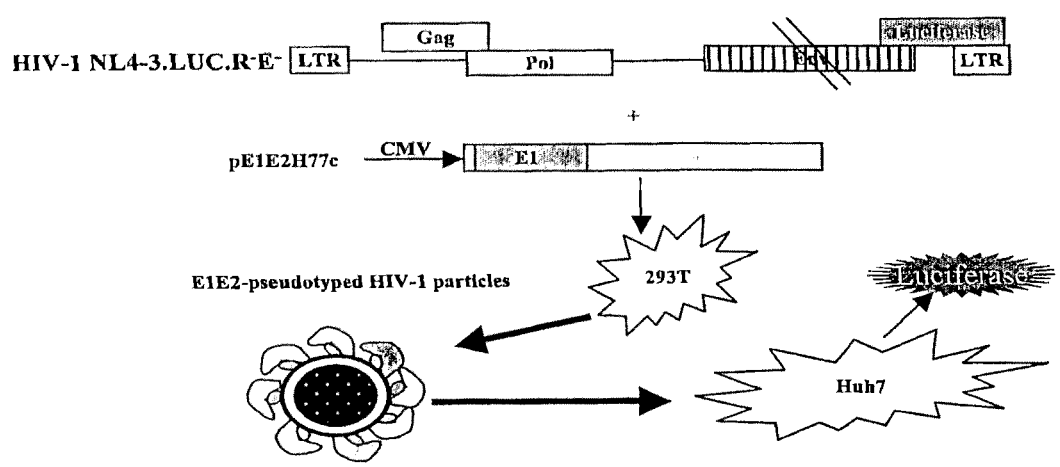
FIG. 23 shows a schematic representation of the strategy used to generate HCV glycoprotein-pseudotyped HIV-1 particles. The HCV glycoprotein expression vector encoding E1E2 (pE1E2) or pE1E2 containing variable region deletions and the retroviral vector (HIV-1 NL4-3.LUC.R⁻E⁻) lacking its native envelope gene and containing a luciferase reporter gene are co-transfected into 293T cells. As the retroviral core proteins assemble within the cell they acquire an envelope by budding from the plasma membrane, incorporating the HCV E1E2 glycoproteins. These virions are then collected and used to undergo one round of infection and replication in Huh7 cells. The level of E1E2-mediated entry is then quantified by the resulting luciferase activity within these infected Huh7 cells.

The incorporation and display of functional HCV envelope glycoproteins by heterologous retro- or lentiviral core particles, called pseudotyping, provides a relatively rapid and simple method for characterising mutant E1E2 glycoproteins without introducing these mutations into the full-length HCV genome (Drummer et al., 2003, Bartosch et al., 2003b)2003a, Drummer et al., 2003). This strategy involves the co-transfection of both an E1E2 expression vector and a retroviral or lentiviral expression vector lacking its native envelope gene and containing a reporter construct (FIG. 23). As the viral core proteins assemble within the cell they acquire an envelope by budding from the plasma membrane and incorporate the HCV envelope glycoproteins present at the cell surface in place of their native envelope complex. These E1E2-pseudotyped particles (HCVpp) can undergo a single round of E1E2-mediated infection and replication that can be quantified by measuring the activity of the reporter gene within the infected cell. During this study, the human immunodeficiency virus (HIV-1) fire-fly luciferase vector, HIV-1 NL4-3.LUC.R$^-$E$^-$ (He and Landau et al., 1995) was used to generate E1E2-pseudotyped virus for infection of Huh-7 cells as previously described (Drummer et al., 2003).

293T cells were seeded at 350 000 cells/well in 6-well culture dishes (Nalge Nunc) and co-transfected with 1 ug of NL4-3.LUC.R⁻E⁻ and 1 ug of either pE1E2H77c (wild-type), pΔHVR E1E2 or the empty pCDNA4HisMax vector (negative control). After three days incubation, the tissue culture fluid containing E1E2-pseudotyped HIV-1 particles was collected and filtered using Minisart 0.45 um sterile syringe filters (Sartorius, Goettingen Germany). The filtered product was then used to infect Huh-7 cells seeded at 30 000 cells/well in 48-well culture plates (Nalge Nunc) in triplicate. Following 4 hr incubation at 37° C., the innoculum was removed and the cells cultured in DMF10 for a further 3 days before being lysed with cell culture lysis reagent (Promega, Madison, Wis., USA). Cell lysates were clarified of cellular debris prior to being transferred into white 96-well plates (BMG Labtech, Offenburg, Germany) to be analysed for luciferase activity using the Steady-Glo luciferase reagent system (Promega) and a Fluostar (BMG Labtech) fitted with luminescence optics. The average luciferase activity (relative light units) was calculated from triplicate infections and the standard deviation calculated accordingly.

Radioimmunoprecipitation (RIP)

Radiolabelling

In order to analyse the role of the variable regions in intracellular E1E2 biosynthesis, 293T cells seeded at 500 000 cells/well in 6-well culture dishes (Nalge Nunc) were transfected with 2 ug of either pE1E2 (wild-type), pE1E2 containing one or more variable region deletions or empty pCDNA4 vector (negative control). 24 hours post-transfection, cells were pulse-chase metabolically labelled for 30 min at 37° C. with 150 µCi Trans-³⁵S-label/well (Santa Cruz Biotechnology, Santa Cruz, Calif., USA) in L-cysteine and L-methionine deficient DMF10: DMEM (MP Biomedicals), 10% (v/v) heat-inactivated fetal bovine serum (Invitrogen) and 2 mM L-glutamine (GE Healthcare). The cells were then chased for 4 hrs in DMF10 at 37° C. prior to being washed in PBS and lysed in RIP lysis buffer (0.6 M KCl, 0.05 M Tris pH 7.4, 1 mM EDTA, 0.02% sodium azide, 1% Triton X-100). The cell lysates were clarified of any remaining cell debris by centrifugation for 10 min at 4° C. in a refrigerated bench-top centrifuge (Heraeus, Hanau, Germany).

To enrich for mature E1E2 heterodimers as incorporated into pseudotyped HIV-1 particles, 293T cells seeded at 350 000 cells/well in 6 well-culture dishes were transfected with 1 ug of pNL4-3.LUC.R–E– plus 1 ug of either pE1E2 (wild-type), pE1E2 containing one or more variable region deletions or empty pCDNA4 vector (negative control). 24 hrs hours post-transfection, the cells were metabolically labelled with 75 µCi Trans-³⁵S label/well (Santa Cruz Biotechnology) in L-cysteine and L-methionine deficient DMF10 for 16 hrs at 37° C. The tissue culture fluid was then collected and filtered through a Minisart 0.2 um syringe filter (Sartorius) prior to being enriched for virions through a sucrose gradient (25% sucrose (v/v) in PBS) using the Beckman L-90 ultracentrifuge (SW41 rotor, Beckman Coulter, Fullerton, Calif., USA) at 25 000×g for 2 hrs at 4° C. The supernatant was removed prior to lysis of the virions in RIP lysis buffer.

To characterise the role of the variable regions in the context of the E2 receptor-binding domain (E2 RBD$_{661myc}$), metabolically labelled 293T cells seeded at 350 000 cells/well in 6-well culture dishes (Nalge Nunc) were transfected with 2 ug of either the E2-myc (wild-type), E2-myc containing one or more variable region deletions por empty pCDNA3 vector (negative control). 6 hrs post-transfection, cells were pulse-chase metabolically labelled with 75 µCi Trans-³⁵S-label/well (Santa Cruz Biotechnology) for 1 hr at 37° C. and chased in OptiMEM serum reduced media (Invitrogen) for 16 hrs to accumulate secreted protein. This tissue culture fluid was then collected and lysed in RIP lysis buffer prior to clarification by centrifugation at 10,000×g at 4° C. The cell monolayer was also washed in PBS, lysed in RIP lysis buffer and clarified as described above.

Immunoprecipitation

Radioimmunoprecipitation was used as a conformational-sensitive strategy to analyse protein expression. All protein preparations above were pre-cleared with Sepharose (GE Healthcare) coupled to BSA (Sigma) in the presence of the relevant antibody for 16 hrs at 4° C. The BSA-Sepharose was pelleted at 8 000×g for 10 min to remove any non-specific protein species. The supernatant containing antibody-bound proteins was then precipitated using 30% (v/v) Protein-G Sepharose (GE Healthcare) in RIP lysis buffer for 1 hr at room temperature and isolated by centrifugation as above prior to washing three times in RIP wash buffer (0.5 M NaCl, 0.05 M Tris pH 7.4, 1 mM EDTA, 0.02% sodium azide and 1% Triton-X 100) and once in PBS.

SDS-Polyacrylamide Gel Electrophoresis (SDS-PAGE) Protein Separation and Analysis All immunoprecipitates were resuspended in sample loading buffer (0.5 M Tris pH 6.8, 5% (v/v) SDS, 10% (v/v) glycerol, 0.05% (w/v) bromophenol blue). Intracellular lysates were run under either reducing (+3% (v/v) β-mercaptoethanol) or non-reducing conditions (no β-mercaptoethanol) to identify non-covalently associated E1E2 species within the large amounts of intracellular covalently-linked E1E2 aggregate as previously observed (Dubuisson et al., 1994). Metabolically-labelled virion-incorporated E1E2 in viral lysates were run under non-reducing conditions, while the HIV-1 structural proteins were run under reducing conditions. All samples were denatured at 100° C. for 5 min prior to separation on 10-15% SDS-PAGE polyacrylamide gradient gels (except IgG14 samples that were separated on a 7.5-15% gradient) using the Miniprotean II SDS-PAGE system (BioRad) in reference to a pre-stained broad-range protein marker (BioRad). Electrophoresis was conducted at 100V, 23 mA for 1.5 hrs in 1× electrode buffer (0.2M Tris-HCl and 2M Glycine). The SDS-PAGE gels were then submerged in 10% (v/v) acetic acid and 10% (v/v) methanol to fix the samples prior to drying at 80° C. using a vacuum slab-gel dryer (Hoefer Scientific, San Francisco, Calif., USA). The broad-range marker positions were marked with ³⁵S-Trans label (Santa Cruz Biotechnology) prior to protein analysis and quantification using the FLA-2000 Phosphoimager and Software (Fuji Film, Tokyo, Japan).

Solid-Phase CD81-LEL Binding Assay

The large extracellular loop of CD81 has been demonstrated to be sufficient to mediate E2 glycoprotein binding (Pileri et al., 1998, Petracca et al., 2000, Pileri et al., 1998)

and contains all the residues that form the E2 interaction site and contains all the residues that form the E2 interaction site (Drummer et al., 2002). Therefore, to rapidly screen for the CD81-LEL binding ability in the variable region deletion mutants, we used a solid-phase binding assay constructed using a chimera composed of the maltose-binding protein (MBP) linked to the CD81 large-extracellular loop residues 113-201 (MBP-LEL) as previously described (Drummer et al., 2002).

Briefly, 96-well maxisorb enzyme linked immunosorbant plates (Nalge Nunc) were coated with 5 ug/mL of dimeric CD81 MBP-LEL in PBS and incubated for 16 hrs at 4° C. The MBP-LEL was removed prior to blocking with $BSA_{10}PBS$ (10 mg/mL BSA (Sigma) in PBS) for 2 hrs at 37° C. to reduce non-specific binding. The plates were then washed four times in PBST (0.05% Tween-20 (Sigma) in PBS) prior to the addition of all the protein lysate preparations at twelve two-fold serial dilutions in $BSA_5PBST$ (5 mg/mL BSA in PBST). Plates were incubated for 2 hrs at room temperature, washed again, and probed for bound E2 with the conformation-dependent anti-E2 monoclonal antibody H53 for 1 hr (1:1000 dilution in $BSA_5PBST$). After further washing in PBST, the antibody-bound E2 complexes were detected using a rabbit anti-mouse immunoglobulin—horseradish peroxidise conjugate (DAKO) (1:1000 dilution in $BSA_5PBS$/Tween) and developed with a tetra-methylbenzidine substrate (Sigma) according to the manufacturer's instructions. The resulting absorbance values (optical density) were read at 450 nm-620 nm (background) on the Fluostar (BMG technologies). This data was then normalized against monomeric E2 as detected by conformation-dependent antibody H53, visualized and quantified in the previous sections.

E2⁻Myc-CD81 Cell Surface-Binding Assays.

CHO-K1 cells were seeded in 12-well culture plates at $1.25 \times 10^5$ cells/well and transfected with 2 μg pcDNA3-CD81 24 h later. At 48-h post transfection the CD81 transfected CHO-K1 cells were chilled on ice and incubated with serial dilutions of wild-type or E2-myc protein containing variable region deletions in $BSA_{10}PBS$ for 4 h on ice. The cells then were washed twice in $BSA_{10}PBS$ prior to a 1 h incubation with $^{125}$I-MAb 9E10 ($10^6$ cpm) that had been precleared with $10^7$ CHO-K1 cells for 2 h on ice. After 4 further washes with $BSA_{10}PBS$, the cells were lysed in 1% SDS in PBS and counted in a Packard Auto-Gamma counter.

TABLE 1

Summary of results obtained for variable region deletion constructs in both the context of the E1E2 polyprotein and the E2 receptor-binding domain constructs containing a myc epitope tag (E2 -myc).

| | Deletion | Heterodimerization [1] | H53 Recognition | CD81-LEL Binding [2] | Heterodimerization [1] | H53 Recognition | Viral Entry [3] | CD81-LEL binding [2] |
|---|---|---|---|---|---|---|---|---|
| Polyprotein Mutant | | Intracellular E1E2 precursors | | | Mature virion-incorporated E1E2 | | | |
| pE1E2 | Wild-type | + | + | + | + | + | + | + |
| pE1E2 Δ1 | HVR1 | + | + | ++ | + | + | − | ++ |
| pE1E2 Δ1con | HVR1 + conserved region | + | + | − | − | reduced | − | − |
| pE1E2 Δ2 | HVR2 | − | + | ++ | − | + | − | + |
| pE1E2 Δ3 | igVR | − | + | ++ | − | + | − | + |
| pE1E2 Δ1 conlink | HVR1 + conserved region with extended linker | + | + | +/− | − | reduced | − | − |
| pE1E2 Δ2 link | HVR2 with extended linker | − | + | ++ | − | + | − | + |
| pE1E2 Δ3 link | igVR with extended linker | + | + | ++ | + | + | +/− | + |
| pE1E2 Δ12 | HVR1 and 2 | − | + | + | − | + | − | + |
| pE1E2 Δ13 | HVR1 and igVR | − | + | + | − | + | − | + |
| pE1E2 Δ23 | HVR2 + igVR | − | + | ++ | − | + | − | + |
| pE1E2 Δ123 | HVR1, HVR2 + igVR | − | + | + | − | + | − | ++ |
| E2 RBD Mutant | | Intracellular E2 $RBD_{661myc}$ | | | Secreted E2 $RBD_{661myc}$ | | | |
| E2-myc | Wild-type | + | + | | | + | + | |
| E2 Δ1-myc | HVR1 | + | ++ | | | + | ++ | |
| E2 Δ1con-myc | HVR1 + conserved region | + | − | | | + | − | |
| E2 Δ2-myc | HVR2 | + | +/− | | | + | + | |
| E2 Δ3-myc | igVR | + | +/− | | | + | + | |
| E2 Δ12-myc | HVR1 and 2 | + | +/− | | | + | − | |
| E2 Δ13-myc | HVR1 and igVR | + | + | | | + | ++ | |
| E2 Δ23-myc | HVR2 + igVR | + | + | | | + | + | |
| E2 Δ123-myc | HVR1, HVR2 + igVR | + | ++ | | | + | + | |

[1] + represents heterodimerization levels similar to wild-type E1E2. − represents no heterodimerization detected. +/− represents reduced heterodimerization relative to wild-type E1E2.
[2] + represents CD81-LEL binding levels similar to wild-type E1E2. − represents no CD81-LEL binding detected. +/− represents reduced CD81-LEL binding relative to wild-type E1E2.
++ enhanced binding relative to wild-type.
[3] + represents viral entry at levels similar to wild-type E1E2. − represents no detectable viral entry. +/− represents partially entry competent.

TABLE 2

Summary of the overlap extension PCR strategy used to introduce modified single variable region deletions with linker sequences into the HCV E1E2 polyprotein.

| pE1E2 construct | Template Vector | Round 1 PCR Product | External Primer | Internal Primer | RE Site | Epitope Tag | PCR product (bp) | Insert size (bp) | MW (Da) |
|---|---|---|---|---|---|---|---|---|---|
| pE1E2 Δ1conlink | pE1E2H77c | 5' | 5' ggt gga att ctg gca aca ggg aac ctt cct gg 3' | 5' gct ttc att gca att caa ggc cgt GCC GCT ACT ACC gtg ggt ttc cgc gtc gac 3' | EcoR I | none | 716 | 1563 | 36 482 |
| | pE1E2H77c | 3' | 5' ccg tct aga tta cgc ctc cgc ttg gga tat gag 3' | 5' GGT AGT AGC GGC acg gcc ttg aat tgc aat gaa agc ctt aac acc 3' | XbaI | none | 993 | | |
| pE1E2 Δ2 link | pE1E2H77c | 5' | 5' ggt gga att ctg gca acc ggg aac ctt cct gg 3' | 5' gta gtgt cca gca gta ggg GCC GCT ACT ACC aag gcg tcg gca gct ggc ca acct ctc 3' | EcoR I | none | 938 | 1614 | 38 071 |
| | pE1E2H77c | 3' | 5' ccg tct aga tta cgc ctc cgc ttg gga tat gag 3' | 5' GGT AGT AGC GGC ccc tac tgc tgg cac tac cct cca aga cct tgt ggc 3' | XbaI | none | 816 | | |
| pE1E2 Δ3 link | pE1E2H77c | 3' | 5' ggt gga att ctg gca aca ggg aac ctt cct gg 3' | 5' gca atc agt ggg gca gag caa GCC GCT ACT ACC gat gac aca agg ggg cgc tcc gca cac 3' | XbaI | none | 1268 | 1656 | 39 963 |
| | pE1E2H77c | 3' | 5' ccg tct aga tta cgc ctc cgc ttg gga tat gag 3' | 5' GGT AGT AGC GGC ttg ctc tgc ccc act gat tgc ttc cgc 3' | XbaI | none | 531 | | |

Capitalised and underlined primer sequences represent the introduced Gly—Ser—Ser—Gly linker motif and restriction endonuclease sites, respectively.

TABLE 3

Summary of the overlap extension PCR strategy used to introduce multiple variable region deletions into the HCV E1E2 polyprotein.

| pE1E2 construct | Template Vector | Round1 PCR Product | External Primer | Internal Primer | RE Site | Epitope Tag | PCR product (bp) | Insert size (bp) | MW (Da) |
|---|---|---|---|---|---|---|---|---|---|
| pE1E2 Δ12 | pE1E2 Δ2 | 5' 5' | 5' ggt gga att ctg gca aca ggg aac ctt cct gg 3' | 5' ttg gat gtt ctg GCC GCT ACT ACC gtg ggt ttc cgc gtc gac 3' | EcoRI | none | 704 | 1545 | 35 697 |
|  | pE1E2 Δ2 | 3' 5' | 5' ccg tct aga tta cgc ctc cgc ttg gga tat gag 3' | 5' GGT AGT AGC GGC cag aac atc caa ctg atc aac acc 3' | XbaI | none | 981 |  |  |
| pE1E2 Δ13 | pE1E2 Δ3 | 5' 5' | 5' ggt gga att ctg gca aca ggg aac ctt cct gg 3' | 5' ttg gat gtt ctg GCC GCT ACT ACC gtg ggt ttc cgc gtc gac 3' | EcoRI | none | 704 | 1590 | 37 566 |
|  | pE1E2 Δ3 | 3' 5' | 5' ccg tct aga tta cgc ctc cgc ttg gga tat gag 3' | 5' GGT AGT AGC GGC cag aac atc caa ctg atc aac acc 3' | XbaI | none | 1041 |  |  |
| pE1E2 Δ23 | pE1E2 Δ3 | 5' 5' | 5' ggt gga att ctg gca aca ggg aac ctt cct gg 3' | 5' gta gtg cca gca GCC GCT ACT ACC gca gct ggc caa cct ctc 3' | EcoRI | none | 932 | 1578 | 36 561 |
|  | pE1E2 Δ3 | 3' 5' | 5' ccg tct aga tta cgc ctc cgc ttg gga tat gag 3' | 5' GGT AGT AGC GGC tgc tgg cac tac cct cca aga cct tgt ggc 3' | XbaI | none | 810 |  |  |
| pE1E2 Δ123 | pE1E2 Δ12 | 5' 5' | 5' ggt gga att ctg gca aca ggg aac ctt cct gg 3' | 5' gca atc agt ggg gca GCC GCT ACT ACC aca agg ggg cgc tcc gca ca 3' | EcoRI | none | 1256 | 1524 | 34 962 |
|  | pE1E2 Δ12 | 3' 5' | 5' ccg tct aga tta cgc ctc cgc ttg gga tat gag 3' | 5' GGT AGT AGC GGC tgc ccc act gat tgc ttc cgc 3' | XbaI | none | 525 |  |  |

Capitalized and underlined primer sequences represent the introduced Gly-Ser-Ser-Gly linker motif and restriction endonuclease sites, respectively.

TABLE 4

Summary of the standard PCR strategy used to construct single and multiple variable region deletions into the E2 receptor-binding domain (residues 384-661).

| E2-myc construct | Template Vector | External sense primer | External anti-sense primer | RE Sites | Epitope Tag | Insert Size (bp) | MW (Da) |
|---|---|---|---|---|---|---|---|
| E2 Δ1con-myc | pE1E2 Δ1con | 5' cca gct agc gaa acc cac ggt agt agc ggc 3' | 5' ccg tct aga cta att cag atc ctc ttc tga gat gag ttt ttg ttc agt act ctc gga ct gtc cct gtc 3' | NheI/ XbaI | myc | 783 | 29,385 |
| E2 Δ1-myc | pE1E2 Δ1 | 5' caa gct agc gaa acc cac ggt agt agc ggc 3' | 5' ccg tct aga cta att cag atc ctc ttc tga gat gag ttt ttg ttc agt act ctc gga cct gtc cct gtc 3' | NheI/ XbaI | myc | 843 | 31,623 |
| E2 Δ2-myc | pE1E2 Δ2 | 5' cca gct agc gaa acc cac gtc acc ggg gga aat gc 3' | 5' ccg tct aga cta att cag atc ctc ttc tga gat gag ttt ttg ttc agt act ctc gga cct gtc cct gtc 3' | NheI/ XbaI | myc | 831 | 31,282 |
| E2 Δ3-myc | pE1E2 Δ3 | 5' caa gct agc gaa acc cac gtc acc ggg gga aat gc 3' | 5' ccg tct aga cta att cag atc ctc ttc tga gat gag ttt ttg ttc agt act ctc gga cct gtc cct gtc 3' | NheI/ XbaI | myc | 876 | 33,139 |

TABLE 4-continued Summary of the standard PCR strategy used to construct single and multiple variable region deletions into the E2 receptor-binding domain (residues 384-661).

| E2-myc construct | Template Vector | External sense primer | External anti-sense primer | RE Sites | Epitope Tag | Insert Size (bp) | MW (Da) |
|---|---|---|---|---|---|---|---|
| E2 Δ12-myc | pE1E2 Δ12 | 5' caa <u>gct agc</u> gaa acc cac ggt agt agc ggc 3' | 5' ccg <u>tct aga</u> cta att cag atc ctc ttc tga gat gag ttt ttg ttc agt act ctc gga ct gtc cct gtc 3' | NheI/ XbaI | myc | 777 | 28,865 |
| E23 Δ13-myc | pE1E2 Δ13 | 5' caa <u>gct agc</u> gaa acc cac ggt agt agc ggc 3' | 5' ccg <u>tct aga</u> cta att cag atc ctc ttc tga gat gag ttt ttg ttc agt act ctc gga cct gtc cct gtc 3' | NheI/ XbaI | myc | 822 | 30,624 |
| E2 Δ23-myc | pE1E2 Δ23 | 5' cca <u>gct agc</u> gaa acc cac gtc acc ggg gga aat gc 3' | 5' ccg <u>tct aga</u> cta att cag atc ctc ttc tga gat gag ttt ttg ttc agt act ctc gga cct gtc cct gtc 3' | NheI/ XbaI | myc | 811 | 30,381 |
| E2 Δ123-myc | pE1E2 Δ123 | 5' caa <u>gct agc</u> gaa acc cac ggt agt agc ggc 3' | 5' ccg <u>tct aga</u> cta att cag atc ctc ttc tga gat gag ttt ttg ttc agt act ctc gga cct gtc cct gtc 3' | NheI/ XbaI | myc | 756 | 27,964 |

Underlined primer sequences represent introduced restriction endonuclease sites.

TABLE 5

Summary of the overlap extension PCR strategy used to introduce single variable region deletions into the HCV E1E2 polyprotein.

| pE1E2 construct | Template Vector | Round1 PCR Product | External Primer | Internal Primer | RE Site | Epitope Tag | PCR product (bp) | Insert size (bp) | MW (Da) |
|---|---|---|---|---|---|---|---|---|---|
| pE1E2 Δ1con | pE1E2-H77c | 5' | 5' ggt gg<u>a att c</u>tg gca aca ggg aac ctt cct gg 3' | 5' gct ttc att gca GCC GCT ACT ACC gtg ggt ttc cgc gtc gac 3' | EcoRI | none | 704 | 1551 | 36 083 |
| | pE1E2-H77c | 3' | 5' ccg <u>tct aga</u> tta cgc ctc cgc ttg gga tat gag 3' | 5' GGT AGT AGC GGC tgc aat gaa agc ctt ac accc 3' | XbaI | none | 981 | | |
| pE1E2 Δ1 | pE1E2-H77c | 5' | 5' ggt gg<u>a att c</u>tg gca aca ggg acc ctt cct gg 3' | 5' GGT AGT AGC GGC cag ac atc caa ctg atc aac acc 3' | EcoRI | none | 704 | 1611 | 38 301 |
| | pE1E2-H77c | 3' | 5' ccg <u>tct aga</u> tta cgc ctc cgc ttg gga tat gag 3' | 5' GGT AGT AGC GGC cag aac atc caa ctg atc aac acc 3' | XbaI | none | 1041 | | |
| pE1E2 Δ2 | pE1E2-H77c | 5' | 5' ggt gg<u>a att c</u>tg gca aca ggg aac ctt cct gg 3' | 5' gta gtg cca gca GCC GCT ACT ACC gca gct ggc caa cct ctc 3' | EcoRI | none | 932 | 1599 | 37 386 |
| | pE1E2-H77c | 3' | 5' ccg <u>tct aga</u> tta cgc ctc cgc ttg gga tat gag 3' | 5' GGT AGT AGC GGC tgc tgg cac tat cct cca aga cct tgt ggc 3' | XbaI | none | 810 | | |
| pE1E2 Δ3 | pE1E2-H77c | 5' | 5' ggt gg<u>a att c</u>tg gca aca ggg aac ctt cct gg 3' | 5' gca atc agt ggg gca GCC GCT ACT ACC aca agg ggg cgc tcc tca cac 3' | EcoRI | none | 1256 | 1644 | 39 255 |
| | pE1E2-H77c | 3' | 5' ccg <u>tct aga</u> tta cgc ctc cgc ttg gga tat gag 3' | 5' GGT AGT AGC GGC tgc ccc act gat tgc ttc cgc 3' | XbaI | none | 525 | | |

Capitalized and underlined oligonucleotide sequences represent the introduced Gly-Ser-Ser-Gly linker motif and restriction endonuclease sites, respectively.

TABLE 6

Polymerase chain reaction (PCR) amplification reaction conditions.

Overlapping: Round 1

| | | |
|---|---|---|
| 95° C. | 2 min | |
| 92° C. | 30 sec | |
| 65° C. | 30 sec | X 29 |
| 72° C. | 2 min | |
| 72° C. | 10 min | |

Overlapping: Round 2

| | | |
|---|---|---|
| 95° C. | 2 min | |
| 92° C. | 30 sec | |
| 55° C. | 30 sec | X 29 |
| 72° C. | 4 min | |
| 72° C. | 10 min | |

Standard

| | | |
|---|---|---|
| 95° C. | 2 min | |
| 92° C. | 30 sec | |
| 55° C. | 30 sec | X 29 |
| 72° C. | 2 min | |
| 72° C. | 10 min | |

Colony

| | | |
|---|---|---|
| 94° C. | 2 min | |
| 94° C. | 30 sec | |
| 55° C. | 30 sec | X 29 |
| 72° C. | 1 min | |
| 72° C. | 10 min | |

Sequencing

| | | |
|---|---|---|
| 96° C. | 1 min | |
| 96° C. | 20 sec | |
| 50° C. | 15 sec | X 29 |
| 60° C. | 4 min | |
| 4° C. | 10 min | |

EXAMPLE 2

Figure 24:
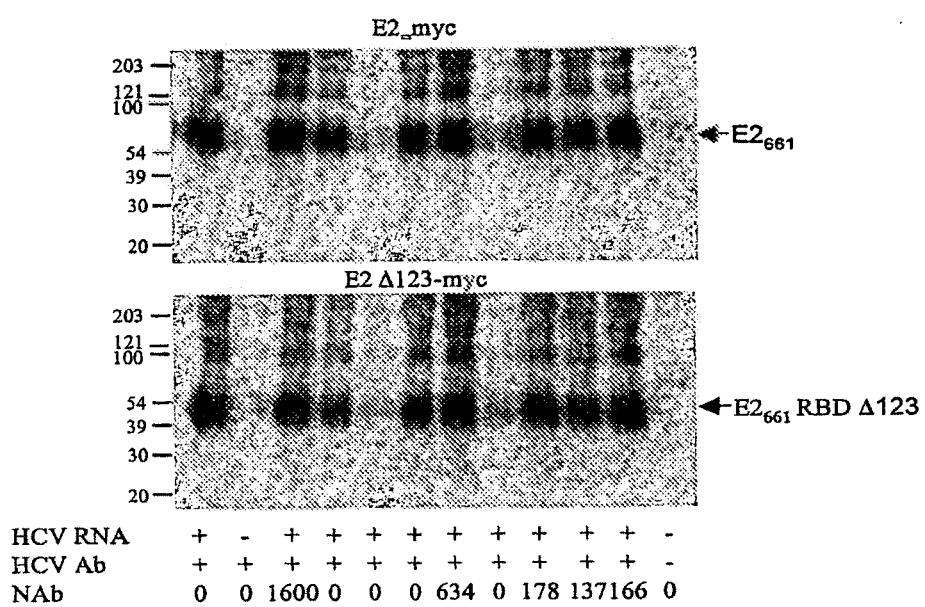
FIG. 24 shows the ability of E2-myc and E2 Δ123-myc proteins to be immunoprecipitated by a panel of human sera obtained from HCV infected individuals. Immunoprecipitated proteins were analysed by SDS-PAGE under non-reducing conditions in 10-15% polyacrylamide gradient gels followed by scanning in a phosphorimager. Below each lane is the HCV RNA status, presence of HCV specific antibody detected using one of BioRad Monolisa, Abbot Murex or Chiron RIBA assays and the 50% neutralizing antibody titre for that serum sample. Molecular weight markers are indicated to the left.

1. Antigenic Structure of E2-Myc and E2 Δ123-myc Probed with a Panel of Sera Obtained from HCV-Infected Individuals A panel of sera obtained from HCV-infected individuals was used to compare the global antigenic profiles of biosynthetically labeled E2-myc and E2 Δ123-myc by immunoprecipitation. The sera were screened for the presence of neutralizing antibodies towards H77c E1E2 pseudotyped retroviral particles as described previously (Grollo et al., 2006), with 50% neutralization titers ranging from 0 to 1,600 observed (Figure. 24, lower panel). The antibody reactivity pattern of E2-myc (FIG. 24, upper panel) was almost identical to that of E2 Δ123-myc (FIG. 24, middle panel), indicating that the gross antigenic structure of the two proteins is similar.

2. CD81 Binding Properties of E2-myc Wild Type and Variant Proteins

Figure 25:
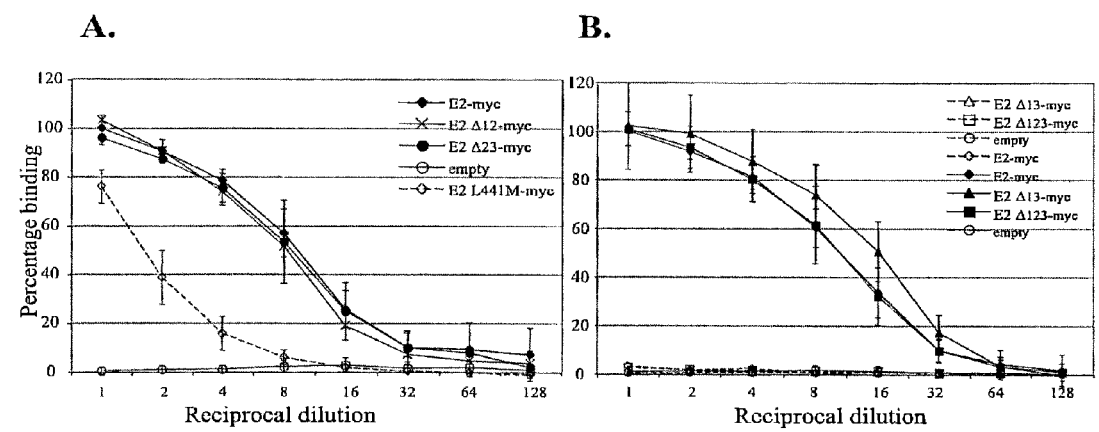
FIG. 25 shows the ability of E2-myc proteins containing variable region deletions to interact with recombinant large extracellular loop of CD81. A. Ability of wild-type E2-myc, E2 Δ12-myc, E2 Δ23-myc and E2-myc protein containing the mutation L441M, that disrupts interaction with CD81, to interact with wild-type recombinant MBP-LEL. E2-myc proteins were serially diluted in MBP-LEL coated enzyme immunoassay plates. Data is the average of two to seven independent experiments and is shown as the mean percentage binding relative to wild-type E2-myc±standard deviation. B. Ability of WT E2-myc, E2 Δ13-myc and E2 Δ123-myc to interact with wild-type recombinant MBP-LEL (solid lines) or recombinant MBP-LEL containing the F186S mutation that disrupts E2 binding (dashed line). Data is the average of two to seven independent experiments and is shown as the mean percentage binding relative to wild-type E2-myc±standard deviation.

The abilities of the secreted E2-myc proteins to interact with the large extracellular loop (LEL) of the HCV cellular receptor CD81 was examined. In this assay, CD81-E2-myc binding was detected using a conformation-dependent E2 monoclonal antibody (H53) in an ELISA employing solid-phase maltose binding protein fused to the large extracellular loop of CD81 (residues 113-201; "CD81-LEL"). E2-myc proteins containing one or more deletions of the variable regions displayed wild-type levels of CD81-LEL binding, again indicating that the E2 global fold was not detectably affected by the deletions (FIG. 25A,B). By contrast, binding between the E2 L441M-myc protein, containing an LEL binding site mutation (L441M), and CD81-LEL was not observed, confirming the specificity of the binding assay (FIG. 25A).

3. Abilities of E2-myc Wild Type and Variant Proteins to Interact with Full-Length CD81 Expressed in CHO-K1 Cells The abilities of E2-myc proteins to interact with full-length CD81 receptor were determined by a cell surface binding assay using CHO-K1 cells transfected with a full-length CD81 expression vector as previously described (Drummer et al., 2002). The secreted E2-myc wild type and variant proteins were serially diluted and incubated with CD81-transfected CHO-K1 cells on ice. After washing, the bound E2-myc proteins were detected by using $^{125}$I-labeled monoclonal antibody 9E10, directed to the C-terminal c-myc epitope tag. The specificity of the assay was confirmed by the lack of binding by E2 L441M-myc, containing the L441M CD81 binding site mutation, to wild-type-CD81-transfected CHO-K1 cells (FIG. 26A).

Figure 26:
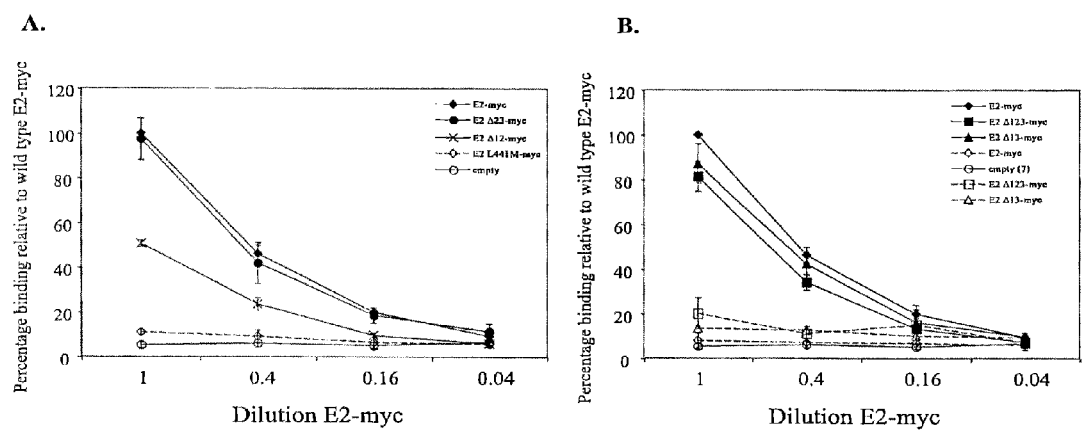
FIG. 26 shows the ability of E2-myc proteins containing variable region deletions to interact with full length surface expressed CD81. A. Ability of WT E2-myc, E2 Δ12-myc, E2 Δ23-myc and E2-myc protein containing the mutation L441M to interact with full length CD81 transfected CHO-K1 cells. Dilutions of wild-type or variable region deleted E2-myc proteins were applied to ice cold, human CD81 transfected CHO-K1 cells and incubated on ice for 4 hrs. After washing, 1×10$^6$ CPM $^{125}$I-9E10 was added and plates incubated for 1 h at room temperature, washed and counted in a Packard Auto GammaCounter. Data shown is the mean percentage binding relative to wild-type±standard error of two to five independent experiments. B. Ability of WT E2-myc, E2 Δ123-myc, and E2 Δ13-myc to interact with full length human CD81 (solid line) or F186S-CD81 (dashed line) transfected CHO-K1 cells. Data shown is the mean percentage binding relative to wild-type±standard error of two to five independent experiments.

The results shown in FIGS. 26A and B indicate that E2-myc, E2 Δ23-myc, E2 Δ13-myc and E2 Δ123-myc have similar CD81 binding properties, whereas the deletion of HVR1 plus HVR2 (E2 Δ12-myc) caused an approximately 50% reduction in CD81 binding compared to binding by E2 Δ23-myc ($p<0.035$). By contrast, the CD81 binding abilities of E2 Δ13-myc (which exhibited a binding curve identical to that of E2-myc) and E2 Δ123-myc were not significantly different ($p=0.62$), indicating that the presence of igVR compromises the CD81 binding function when HVR1 and HVR2 are absent in E2 Δ12-myc. Although HVR1, HVR2, and igVR are not required for the core folding properties of E2 $RBD_{661}$, these data point to a functional interaction between igVR and one or both of HVR1 and HVR2 such that the CD81 binding site is properly formed or becomes fully accessible to the receptor.

Although variations in binding to recombinant CD81-LEL for singly and multiply deleted E2-myc constructs were not detected in FIGS. 25A and 25B, differences in binding to surface-expressed CD81 were observed in FIGS. 26A and 26B, perhaps reflecting subtle differences in LEL structure when it is expressed in isolation versus in native tetraspanin.

4. Materials and Methods

Neutralization Assays

The abilities of immune and control human sera to neutralize a single cycle of infection by HCV glycoprotein-pseudotyped HIV-1 luciferase reporter viruses were determined as follows. HCV glycoprotein-pseudotyped HIV-1 luciferase reporter viruses were prepared by cotransfection of HEK-293T monolayers (350,000 cells per well of 6-well culture dishes) with pE1E2 and pNL4.3LUCR–E– plasmids (Drummer et al., 2003). After 3 days incubation at 37° C. in a humidified atmosphere containing 5% $CO_2$, the culture supernatants were filtered through 0.45 μm sterile syringe filters (Sartorius). Serial dilutions of heat-inactivated immune and control human sera were preincubated with HCV glycoprotein-pseudotyped HIV-1 luciferase reporter viruses (1 h) and then added to quadruplicate Huh7 cell monolayers in 48-well tissue culture plates. Following a 4 h incubation (37° C., 5% $CO_2$) the cells were washed with PBS and fresh medium replaced. After an additional 3-day incubation (37° C. in 5% $CO_2$), the cells were lysed, the lysates clarified by centrifugation and then assayed for luciferase activity (Promega) in a Fluostar (BMG) fitted with luminescence optics. The neutralization titres of individual sera were determined as the serum dilution giving 50% neutralization compared to HCV glycoprotein-pseudotyped HIV-1 luciferase reporter virus preincubated with medium alone.

Radioimmunoprecipitation.

293T cells seeded at 500,000 cells/well in 6-well culture dishes were transfected with E2-myc expression vectors using Fugene 6 (Roche). At 24 hours post-transfection, the cells were labelled with 150 μCi Trans-$^{35}$S-label/well (Santa Cruz Biotechnology, Santa Cruz, Calif., USA) in L-cysteine and L-methionine deficient DMF10 (DMEM [MP Biomedicals], 10% (v/v) heat-inactivated fetal bovine serum [Invitrogen] and 2 mM L-glutamine [GE Healthcare]). After harvesting the cell supernatent, the labelled secreted proteins were adjusted to 0.6 M KCl, 0.05 M Tris pH 7.4, 1 mM EDTA, 0.02% sodium azide, 1% Triton X-100 and precleared with CNBr-activated Sepharose (GE Healthcare) coupled to BSA (Sigma) in the presence of the relevant antibody for 16 h at 4° C. Antibody-antigen complexes within the clarified supernatants were then immunoprecipitated using 30% (v/v) Protein-G Sepharose (GE Healthcare) prior to washing three times in RIP wash buffer (0.5 M NaCl, 0.05 M Tris pH 7.4, 1 mM EDTA, 0.02% sodium azide and 1% Triton-X 100) and once in PBS. The immunoprecipitated proteins were subjected to SDS-PAGE in 10-15% polyacrylamide gradient gels under nonreducing conditions and visualized by scanning in a phosphorimager.

Transient Expression of E2-myc Proteins

HEK 293T cells (350,000 cells per well of 6-well culture plates) were transfected with E2-myc expression vectors using Fugene 6 (Roche). At 8-h post transfection, the transfection medium was replaced with Optimem (Invitrogen) and the cells incubated for 3 days at 37° C. in a humidified atmosphere containing 5% $CO_2$. The tissue culture fluid was clarified through 0.45-μm-pore-size filters and then concentrated by approximately 10-fold in Centricon YM30 concentrators (Amersham).

Recombinant CD81 Large Extracellular Loop (CD81-LEL) Binding Properties.

The abilities of the E2-myc proteins to interact with the HCV cellular receptor CD81 were examined using a solid phase enzyme immunoassay. Enzyme immunoassay plates (Nunc Maxisorb®) were coated with maltose binding protein fused to the recombinant large extracellular loop of CD81 (residues 113-201) at 5 μg/ml in PBS overnight at 4° C. Coating solution was removed and unoccupied sites blocked with bovine serum albumin (10 mg/ml) in PBS ($BSA_{10}PBS$) for 1 h at room temperature. Plates were washed 4 times with PBS containing 0.05% Tween 20 (PBST). The secreted E2-myc proteins were serially diluted in a 50 μl PBS containing 5 mg/ml bovine serum albumin ($BSA_5PBST$) and incubated for 2 h. Bound E2-myc proteins were detected using an E2 specific monoclonal antibody followed by rabbit anti-mouse immunoglobulins coupled to horseradish peroxidase (Dako). Plates were developed using tetramethylbenzidine hydrochloride substrate and stopped by the addition of 1M HCl. Absorbance values were measured at 450 nm and the background at 620 nm subtracted in a Fluostar plate reader (BMG technologies).

CD81 Binding Properties.

CHO-K1 cells were seeded in 12-well culture plates at $1.25 \times 10^5$ cells/well and transfected with 2 μg pcDNA3-CD81 24 h later. At 48-h post transfection the CD81 transfected CHO-K1 cells were chilled on ice and incubated with serial dilutions of wild-type E2-myc or E2-myc proteins containing variable region deletions in $BSA_{10}PBS$ for 4 h on ice. The cells then were washed twice in $BSA_{10}PBS$ prior to a 1-h incubation with $^{125}$I-MAb 9E10 ($10^6$ cpm) that had been precleared with $10^7$ CHO-K1 cells for 2 h on ice. After 4 further washes with $BSA_{10}PBS$, the cells were lysed in 1% SDS in PBS and counted in a Packard Auto-Gamma counter.

EXAMPLE 3

1. SDS-PAGE Analysis of Purified E2-his Wild Type and Variant Proteins

Figure 27:
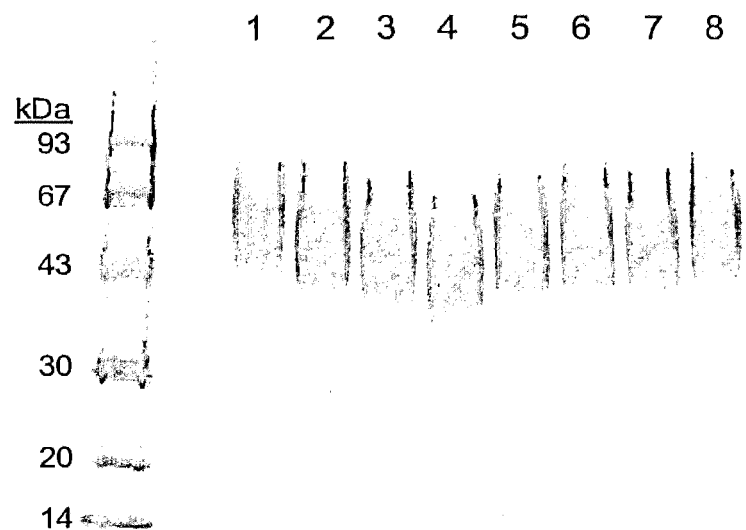
FIG. 27 shows an SDS-PAGE of purified HCV E2 protein variants in 4-20% polyacrylamide gradient gel of the E2-his proteins containing none (wild-type) one or more variable region deletions. The proteins were visualized by staining with Coomassie brilliant blue.
Figure 28:
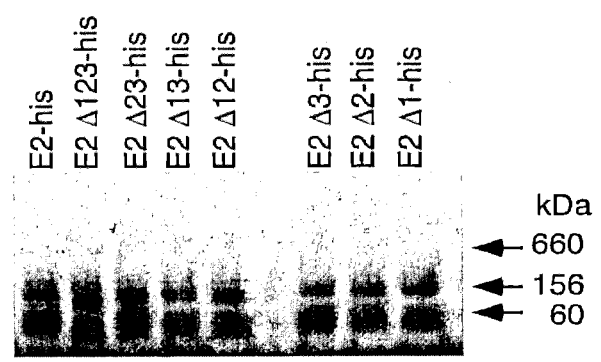
FIG. 28 shows a blue-native PAGE analysis of E2-his proteins. The purified proteins (10 µg) were electrophoresed in 5-15% polyacrylamide gradient gels under native conditions. After electrophoresis, the gels were destained overnight and scanned in a Licor Odyssey scanner at 680 nm. The migration position of protein standards is shown on the right.
Figure 29:
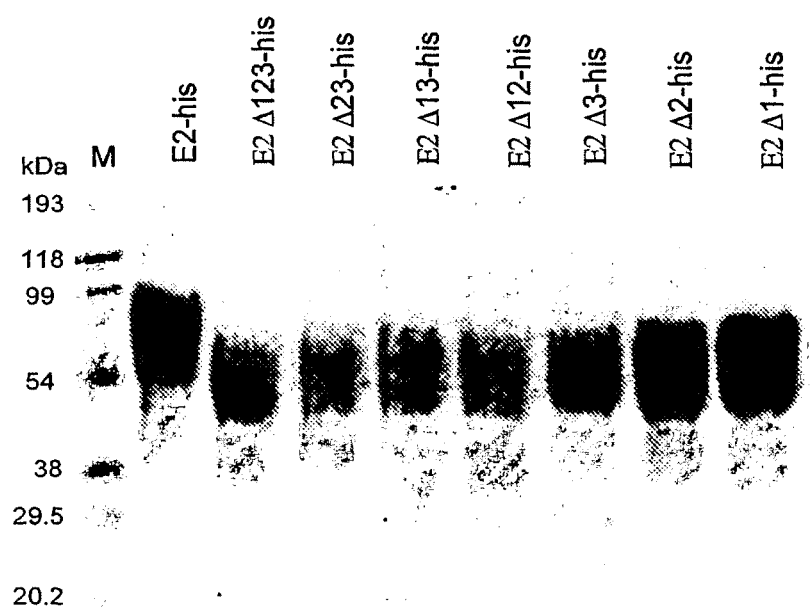
FIG. 29 shows a Western blot analysis of purified E2-his proteins. Samples of the purified proteins were subjected to reducing SDS-PAGE followed by electrophoretic transfer to nitrocellulose membrane. E2 proteins were detected with a non-conformation dependent E2 specific monoclonal antibody followed by goat anti-mouse immunoglobulin coupled to Alexafluor 680 nm (Invitrogen). Immunoblots were scanned in an Licor Odyssey scanner. Molecular weight markers are shown on the left (kDa).

The purity of E2-his wild type and variant proteins was assessed by SDS-PAGE under reducing conditions. FIG. 27 indicates a single band for each purified protein species. The migration of each species was consistent with the number of variable regions deleted. For example, E2 Δ123-his, lacking 3 variable regions, exhibited the fastest migration. The diffuse nature of the protein bands is consistent with glycosylation of E2.

2. Blue-Native PAGE of Purified E2-his Proteins

The oligomerization status of the purified E2-his wild type and variant proteins was analysed using blue native polycrylamide gel electrophoresis. FIG. 28 shows two major bands for each E2-his protein corresponding in molecular weight to monomer and dimer.

3. Immunodetection of E2-his Proteins

The purified E2-his wild type and variant proteins were detected by a non-conformation dependent E2 specific monoclonal antibody (H52) in a western blot. A major protein species migrating at the expected molecular mass was revealed for each E2-his protein variant (FIG. 29).

4. CD81 Binding Properties of E2-his Wild Type and Variant Proteins

The ability of the purified E2-his proteins to interact with the large extracellular loop (LEL) of the HCV cellular receptor CD81 was examined. In this assay, CD81-E2-his binding was detected using a conformation-dependent E2 monoclonal antibody (H53) in an ELISA employing solid-phase maltose binding protein fused to the large extracellular loop of CD81 (residues 113-201; "CD81-LEL"). E2-his proteins containing one or more deletions of the variable regions displayed wild-type levels of CD81-LEL binding, indicating that the E2 global fold was not detectably affected by the deletions (FIG. 30A). By contrast, binding between the E2-his proteins and CD81-LEL containing an E2 binding site mutation (F186S) was not observed, confirming the specificity of the binding assay (FIG. 30B).

Figure 31:
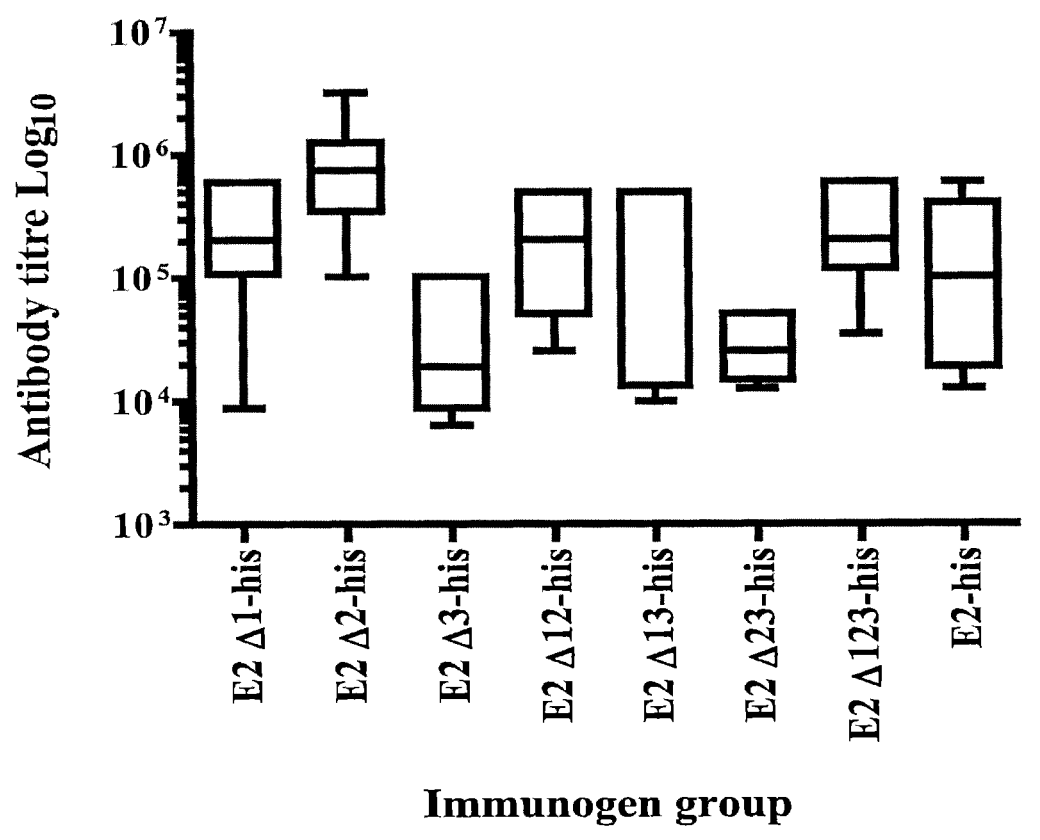

5. Immunoreactivity Towards Homologous E2-his Antigen of Mouse Sera Obtained after 2 Immunizations with E2-his Protein Variants The immunoreactivity of mouse sera obtained after 2 immunizations with the E2-his wild type and variant proteins towards solid-phase "homologous antigen" (i.e. that antigen used to immunize a particular mouse group) was examined by ELISA. Substantial antibody binding activity towards the homologous solid-phase antigen was demonstrated in each of the vaccinated animals (FIG. 31). By contrast, antibody reactivity towards solid-phase E2-his proteins was not detected in the mice vaccinated with adjuvant alone, nor in two representative control sera obtained prior to immunization (prebleed) from each vaccination group (data not shown), confirming that the animals receiving E2-his protein elicited antibodies specific to the immunogen.

Figure 32:
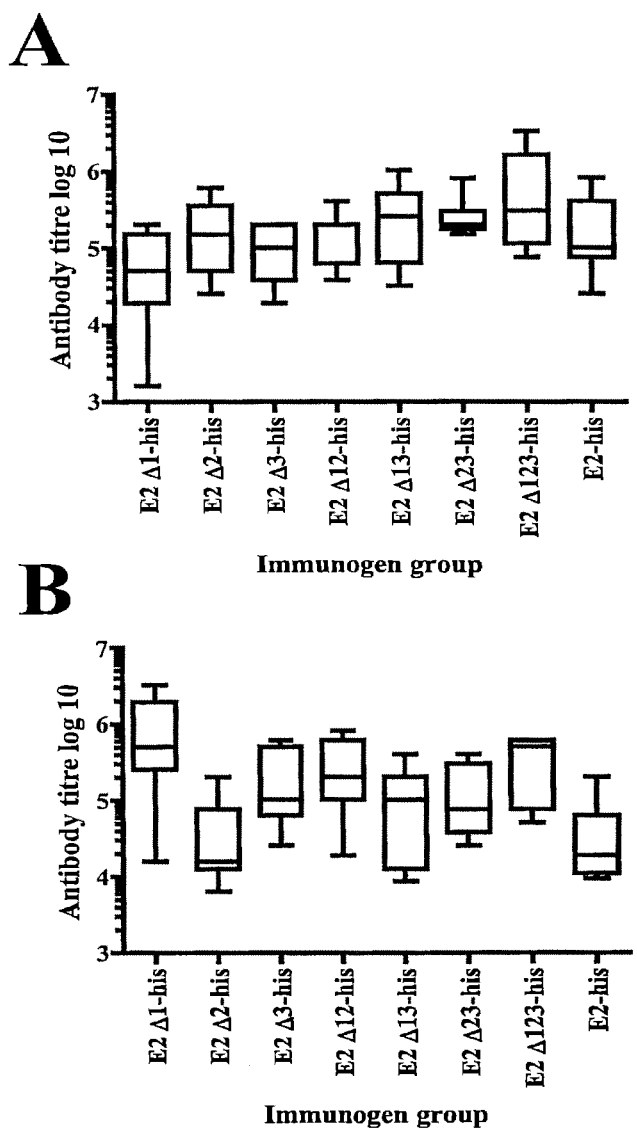
FIG. 32 shows the immunoreactivity towards E2-his (A) and E2 Δ123-his (B) antigens of mouse sera obtained after 2 immunizations with E2 protein variants. E2-his and E2 Δ123-his proteins were captured on 96 well Maxisorb microtitre plates and antibody titres of individual sera determined as described in FIG. 31. The maximum (upper error bar), 75$^{th}$ and 25$^{th}$ percentile (upper and lower edges of box, respectively), median (horizontal line within box) and minimum (lower error bar) titres for each immunogen group are shown.

6. Immunoreactivity Towards E2-his and E2Δ123-his Antigens of Mouse Sera Obtained after 2 Immunizations with E2-his Protein Variants The ability of the antibodies in immune sera from each vaccination group to bind to solid-phase E2-his (containing the three variable regions) was compared to the antibody reactivity towards solid-phase E2 Δ123-his (lacking the three variable regions) in ELISA. Substantial binding titres against solid phase E2-his (FIG. 32A) and E2 Δ123-his (FIG. 32B) were observed for all immunization groups (except adjuvant alone; data not shown).

Pair-wise statistical analyses of the antibody binding titres obtained for the various immunization groups were performed in order to determine whether apparent differences in binding titre were significant. Table 7 indicates that the antibody titres against solid-phase E2-his calculated for the E2-his-immunization group were not significantly different to those of the other immunization groups ($p>0.06$). However, statistically significant differences in antibody reactivity against solid-phase E2-his were observed between the E2 Δ1-his immunization group versus E2 Δ13-his, E2 Δ23-his and E2 Δ123-his ($p<0.04$).

A pair-wise statistical analysis of antibody binding titres against solid-phase E2 Δ123-his for the various immunization groups revealed a highly significant increase in antibody reactivity for the E2 Δ123-his immunization group compared with the E2-his immunization group ($p=0.003$, Table 8). Statistically significant increases in antibody reactivity for the E2 Δ1-his, E2 Δ3-his, and E2 Δ12-his immunization groups versus E2-his were observed, and also for E2 Δ1-his relative to E2 Δ2-his immunization groups ($p<0.04$).

Figure 33:
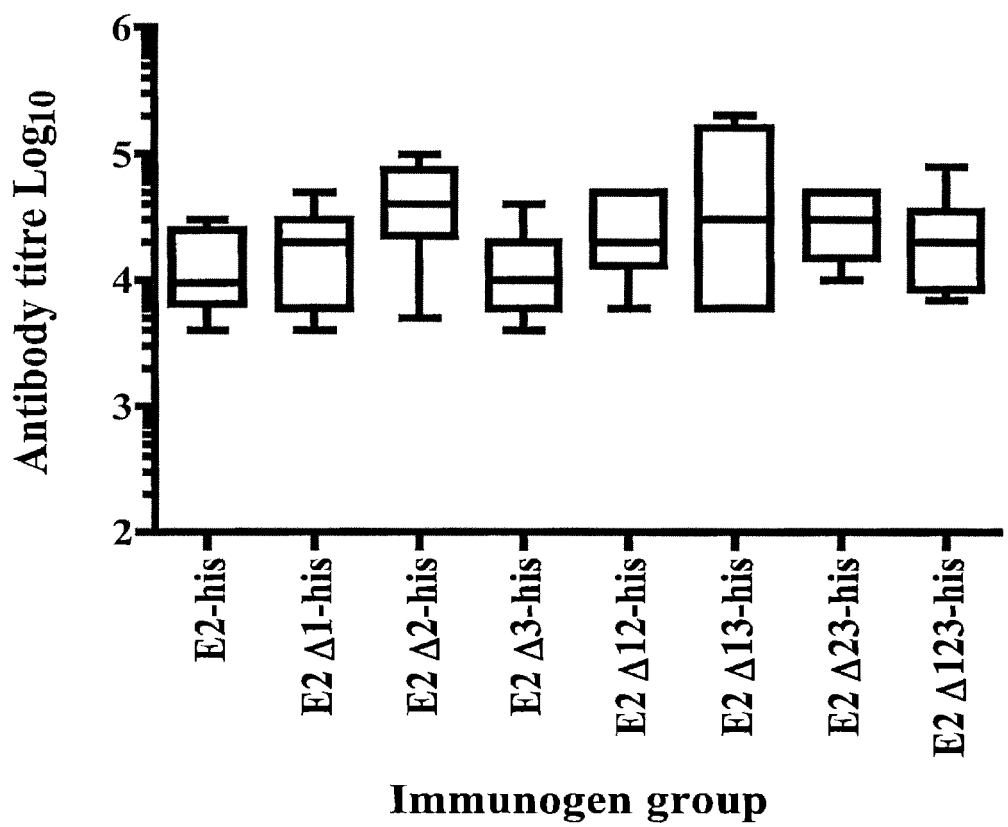
FIG. 33 shows the immunoreactivity towards homologous E2-his antigen of mouse sera obtained after 3 immunizations with E2-his proteins. E2-his proteins were captured on 96 well Maxisorb microtitre plates and antibody titres of individual sera determined as described in FIG. 31. The maximum (upper error bar), $75^{th}$ and $25^{th}$ percentile (upper and lower edges of box, respectively), median (horizontal line within box) and minimum (lower error bar) titres for each immunogen group are shown.

7. Immunoreactivity Towards Homologous E2-his Antigen of Mouse Sera Obtained after 3 Immunizations with E2-his Protein Variants The immunoreactivity of mouse sera obtained after 3 immunizations with the E2-his wild type and variant proteins towards solid-phase "homologous antigen" (i.e. that antigen used to immunize a particular mouse group) was examined by ELISA. Substantial antibody binding activity towards the homologous solid-phase antigen was demonstrated in each of the vaccinated animals (FIG. 33), but not in two representative control sera obtained prior to immunization (prebleed) from each vaccination group (data not shown). Furthermore, antibody reactivity towards solid-phase E2-his proteins was not detected in the mice vaccinated with adjuvant alone (data not shown), confirming that the animals receiving E2-his protein elicited antibodies specific to the immunogen.

Figure 34:
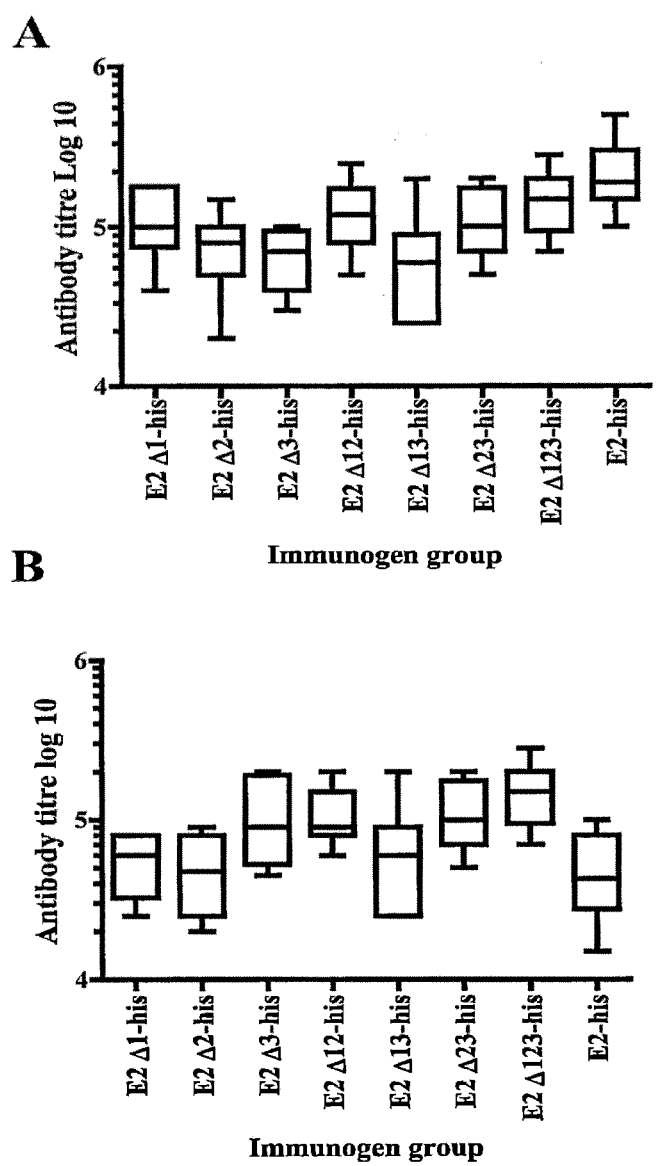
FIG. 34 shows the immunoreactivity towards E2-his (A) and E2 Δ123-his (B) antigens of mouse sera obtained after 3 immunizations with E2 protein variants. E2-his and E2 Δ123-his proteins were captured on 96 well Maxisorb microtitre plates and antibody titres of individual sera determined as described in FIG. 31. The maximum (upper error bar), $75^{th}$ and $25^{th}$ percentile (upper and lower edges of box, respectively), median (horizontal line within box) and minimum (lower error bar) titres for each immunogen group are shown.

8. Immunoreactivity Towards E2-his and E2Δ123-his Antigens of Mouse Sera Obtained after 3 Immunizations with E2-his Protein Variants The ability of the antibodies in immune sera from each vaccination group to bind to solid-phase E2-his (containing the three variable regions) was compared to the antibody reactivity towards solid-phase E2 Δ123-his (lacking the three variable regions) in ELISA. Substantial binding titres against solid phase E2-his (FIG. 34A) and E2 Δ123-his (FIG. 34B) were observed for all immunization groups (except adjuvant alone, data not shown).

Pair-wise statistical comparisons of the antibody binding titres obtained for the various immunization groups were performed in order to determine whether apparent differences in binding titre were significant. In contrast to the data obtained after the second immunization, Table 9 indicates that the antibody titres against solid-phase E2-his calculated for the E2-his-immunization group were significantly higher than those of 6 of 7 other immunization groups ($p=0.003$ to 0.04), excepting the E2 Δ123-his ($p=0.11$).

A pair-wise statistical analysis of antibody binding titres against solid-phase E2 Δ123-his for the various immunization groups revealed a highly significant increase in antibody reactivity for the E2 Δ123-his immunization group compared with the E2-his immunization group ($p=0.0007$, Table 10). Statistically significant differences were also observed between the E2-his versus E2 Δ3-his, E2 Δ12-his, and E2 Δ23-his immunization groups, and also between the E2 Δ1-his versus E2 Δ3-his, E2 Δ12-his, E2 Δ23-his and E2 Δ123-his immunization groups ($p=0.009$ to $0.022$).

Finally, the mean binding titres obtained for each immunization group against solid-phase wild type E2-his antigen (i.e. containing HVR1, HVR2 and IgVR) were compared with the binding titres towards solid-phase E2 Δ123-his antigen (i.e. lacking HVR1, HVR2 and igVR and representing the conserved glycoprotein core). This analysis was performed in order to gauge the relative abilities of the immunogens to elicit antibodies reactive with the conserved core of the $E2_{RBD}$. Table 11 shows significantly lower antibody titres to solid-phase E2 Δ123-his antigen relative to solid-phase E2-his antigen for antisera elicited by E2-his immunogen (~4.4-fold reduction; $p=0.0009$) and E2 Δ1-his immunogen 2-fold reduction; $p=0.005$).

9. Immunoreactivity Towards Solid-Phase Con1 $E2_{RBD}$-his and JFH1 $E2_{RBD}$-Myc Antigens of Mouse Sera Obtained after 3 Immunizations with E2-his Protein Variants The abilities of the E2-his wild type and variant proteins, which are derived from the genotype 1a H77c isolate, to elicit cross-genotype reactive antibodies was determined by comparing the immunoreactivity of immune sera with solid-phase Con1 E2$_{RBD}$-his (genotype 1b) and JFH1 E2$_{RBD}$-myc (genotype 2a) antigens in ELISA. Substantial binding titres against solid phase Con1 E2$_{RBD}$-his (FIG. 35A) and JFH1 E2$_{RBD}$-myc (FIG. 35B) were observed for all immunization groups (except adjuvant alone, data not shown).

A pair-wise statistical analysis of antibody binding titres against solid-phase Con1 E2$_{RBD}$-his for the various immunization groups revealed significantly higher binding titres for E2 Δ2-his, E2 Δ3-his, E2 Δ12-his, and E2 Δ123-his immunization groups compared with the E2-his immunization group (p<0.05, Table 12). The Con1 E2$_{RBD}$-his-binding titre elicited in the E2 Δ123-his immunization group was also significantly higher than the Con1 E2$_{RBD}$-his binding titres elicited by E2 Δ1-his and E2 Δ23-his (p<0.05).

By contrast, a similar pair-wise statistical analysis of antibody binding titres against solid-phase JFH1 E2$_{RBD}$-myc for the various immunization groups did not reveal significantly different binding titres between groups (Table 13). Despite this lack of significance, the trends observed above were also apparent in these analyses.

10. Neutralization

Figure 36:
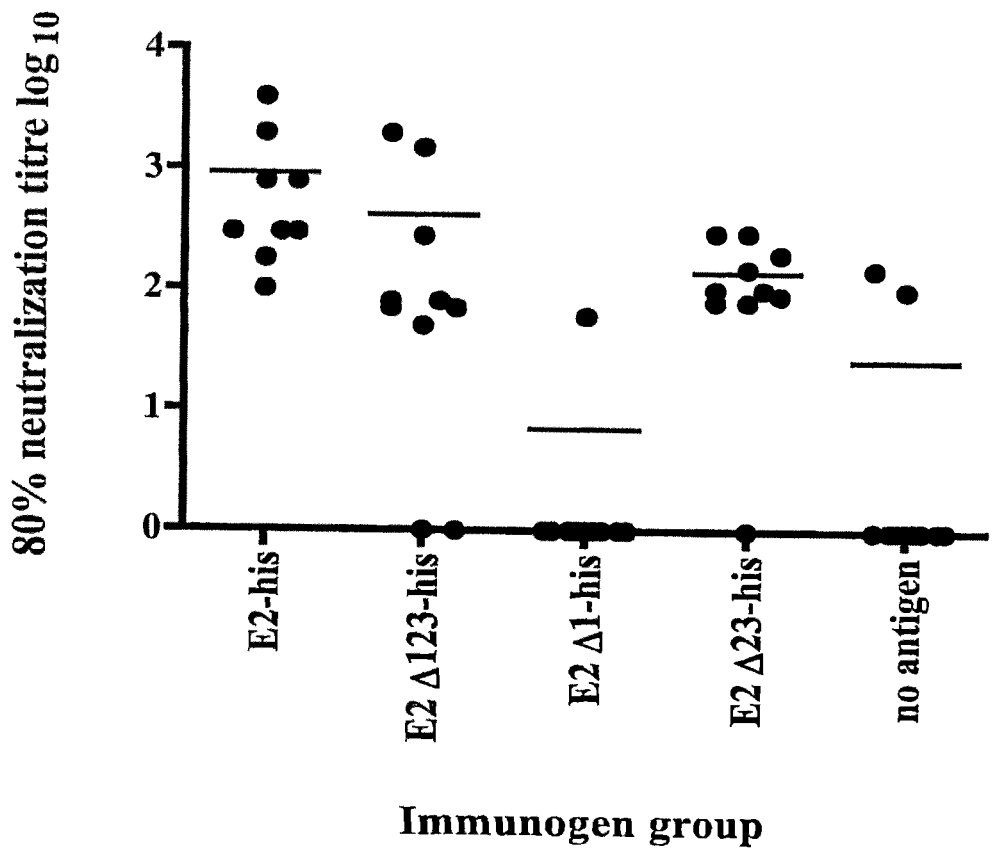
FIG. 36 shows the eighty-percent neutralization titres ($\log_{10}$) of mouse sera obtained after 3 immunizations with E2-his proteins. Serial 5-fold dilutions of heat-inactivated immune mouse sera preincubated for 1 h at 37° C. with H77c HCV glycoprotein-pseudotyped HIV-1 luciferase reporter viruses (1 h) and then added to quadruplicate Huh7 cell monolayers in 48-well tissue culture plates. Following a 4 h incubation (37° C., 5% CO$_2$) the cells were washed with PBS and the medium replaced. After an additional 3-day incubation (37° C. in 5% CO$_2$), the cells were lysed and luciferase activity assayed in a fluostar fitted with luminescence optics. The neutralization titres of individual sera were determined as the serum dilution giving 80% neutralization compared to HCV glycoprotein-pseudotyped HIV-1 luciferase reporter virus preincubated with medium alone.

The abilities of immune and control mouse sera to neutralize a single cycle of infection by homologous H77c strain E1E2-pseudotyped HIV-1 luciferase reporter viruses were determined. Serial 5-fold dilutions of heat-inactivated immune and control mouse sera were preincubated with E1E2-pseudotyped HIV-1 luciferase reporter viruses (1 h) and then incubated for 4 h with Huh7 cell monolayers. The cells were washed with PBS, fresh culture medium added, and after an additional 3-day incubation (37° C. in 5% $CO_2$), the cells were lysed and assayed for luciferase activity. FIG. 36 shows the 80%-neutralization titres of individual sera, which were determined as the serum dilution giving 80% neutralization compared to HCV glycoprotein-pseudotyped HIV-1 luciferase reporter virus preincubated with medium alone. At least 80% of mice immunised with E2-his, E2 Δ123-his and E2 Δ23-his produced neutralizing antibodies against the E1E2-HIV-1 pseudotypes with mean 80% neutralization titres of 908, 413 and 140, respectively. By contrast, at least 80% of mice immunized with E2 Δ1-his or adjuvant alone lacked 80%-neutralization activity with mean 80% neutralization titres of 7 and 26, respectively (Table 14).

11. Discussion

The E2-his proteins containing one or more deletions of the three variable regions were capable of eliciting antibody reactive towards homologous antigens. The specificity of the antibody response was examined by comparing the ability of the immune sera to react towards intact wild-type E2-his protein containing three variable regions to E2 Δ123-his protein which represents the core E2 folding unit lacking all three variable regions but retaining CD81 binding. This analysis revealed that mice immunized with E2-his protein or E2 lacking HVR1 (E2 Δ1-his) elicited significantly less antibody reactive towards the core domain of E2. By contrast antibodies elicited in mice immunized with E2-his proteins lacking HVR1 and 2 (E2 Δ12-his), HVR1 and igVR (E2 Δ13-his), HVR2 and igVR (E2 Δ23-his) or lacking all three variable regions (E2 Δ123-his) reacted similarly towards wild-type E2-his and E2 Δ123-his antigens. This suggests that HVR2 and the igVR may hinder antibody access to epitopes present in the underlying conserved core domain of E2. To test this hypothesis, E2$_{RBD}$ constructs were synthesised representing heterologous isolates of HCV from genotype 1b (Con1) and genotype 2a (JF-H1). The immunoreactivity of mouse serum obtained after the third vaccination to these heterologous E2$_{RBD}$ constructs revealed that mice immunized with E2 Δ123-his, E2 Δ12-his, E2 Δ3-his, E2 Δ2-his elicited significantly higher levels of cross-reactive antibody to epitopes present in the genotype 1b isolate Con1. Although cross-reactive antibody to the E2$_{RBD}$ of genotype 2a isolate JF-H1 were also elicited, the differences in binding titres between the immunogen groups were not statistically significant although trends similar to those above were observed. These data suggest that deletion of at least one variable region, preferably either HVR2 and/or igVR, may improve the ability of E2-his proteins to elicit cross-reactive antibodies with broader neutralization capacity.

The ability of the immune serum to neutralize homologous virus was examined using HCV E1E2 pseudotyped retroviral particles. The data showed that mice vaccinated with E2 Δ123-his or E2 Δ23-his possessed on average ~59 and 20 fold higher neutralizing antibody titres compared with E2-his lacking HVR1 alone (p=0.11 and 0.002, respectively). HVR1 has previously been shown to be an immunodominant region of the E1E2 glycoprotein complex. Deletion of HVR1 region alone may result in the removal of an important type-specific immunodominant epitope. However, the presence of HVR2 and/or the igVR regions in the HVR1 deleted construct may shield underlying cryptic neutralizing epitopes. It is therefore likely that the antibody response elicited by wild-type E2-his protein may be largely directed towards the HVR1 region and not the conserved core. This is in part reflected by (i) the lower level of antibody reactive to the E2 core domain (FIG. 34B) and (ii) the lower levels of cross-reactive antibody (FIG. 35A).

Together the data suggest that deletion of HVR2 and/or the igVR region is a significant improvement on the use of E2 RBD constructs lacking none of the variable regions or HVR1 alone. It is likely that E2 RBD proteins lacking at least HVR2 and/or igVR and possibly all three variable regions will elicit antibody capable of cross-neutralizing divergent HCV strains from within a genotype as well as cross-genotype neutralization. E2 RBD proteins lacking one or more variable regions may be useful tools for both therapeutic or prophylactic vaccination strategies for the prevention or treatment of HCV infection. In addition these variable region deleted E2 RBD constructs may also be useful to elicit novel specificities of antibodies directed to the conserved E2 core region that neutralize HCV for therapeutic and prophylactic use.

12. Materials and Methods

Construction of Wild Type and Variant HCV E2-his cDNAs and Secreted Expression of the Encoded Proteins in Mammalian Cells.

Generation of cDNA Expression Plasmids Encoding HCV E2-his Variants

A synthetic gene encoding a wild type E2 protein fragment (residues 384-661; strain H77c) was constructed by Geneart AG (Regensburg, Germany). The human trypsinogen signal peptide (MNPLLILTFVAAALA) (SEQ ID NO: 63) was appended in-frame to the N-terminus of the wild type E2 mature protein in order to facilitate secretion of the mature polypeptide into the expression medium. A Kozak sequence was introduced just before the N-terminus to increase translational initiation and a (His)$_6$ sequence (SEQ ID NO: 108) was added in-frame to enable subsequent purification of the secreted proteins by immobilised metal affinity chromatography. Two stop codons were added after the His-tag at the C-terminus to ensure efficient translational termination. This construct is referred to as E2-his. The codon usage of the E2-his cDNA was adapted to the codon bias of *Homo sapiens* genes. An Nhe I restriction site at the 5' end of the cDNA and a Xho I restriction site was introduced at the 3' end in order to ligate the Geneart cDNA into Nhe I-Xho I digested pcDNA3.1 (Invitrogen).

The cDNAs encoding seven variants of the E2-his mature protein where one or more of the variable regions were substituted by linker sequences, were constructed using standard PCR mutagenesis procedures with Accuprime Pfx DNA Polymerase (Invitrogen) according to the manufacturer's instructions and the primers shown in Table 15. The combinations of primers used to construct cDNAs of the E2-his are shown in Table 16.

The specific PCR parameters were as follows: 2 minutes of denaturation at 95° C. was followed by 18 cycles of 95° C. for 15 seconds, 64° C. for 30 seconds and 68° C. for 2 minutes with a final 2 minute incubation at 68° C.

The Geneart wild type E2-his cDNA was used as a PCR template for all the E2-his variant cDNAs. Each deletion variant was constructed using sequential overlap PCR of multiple fragments. Once each cDNA was complete, it was digested with Nhe I and Xho I and ligated into pcDNA3.1. Large scale preparations of plasmid DNA were carried out using a Qiagen Maxi Kit. The nucleotide sequences of all the plasmid constructs were verified by sequencing both strands using Big Dye Terminator v3.1 Cycle Sequencing and an Applied Biosystems Automated Sequencer.

The sequences of the mature wild type and variant E2 proteins are as follows:

E2-his mature protein

ETHVTGGNAGRTTAGLVGLLTPGAKQNIQLINTNGSWHINSTALNCNESLNTGWLAGLFYQHKFNSSGCPERL
ASCRRLTDFAQGWGPISYANGSGLDERPYCWHYPPRPCGIVPAKSVCGPVYCFTPSPVVVGTTDRSGAPTYSW
GANDTDVFVLNNTRPPLGNWFGCTWMNSTGFTKVCGAPPCVIGGVGNNTLLCPTDCFRKHPEATYSRCGSGPW
ITPRCMVDYPYRLWHYPCTINYTIFKVRMYVGGVEHRLEAACNWTRGERCDLEDRDRSE

E2Δ1-his mature protein

ETHQNIQLINTNGSWHINSTALNCNESLNTGWLAGLFYQHKFNSSGCPERLASCRRLTDFAQGQGPISYANGS
GLDERPYCWHYPPRPCGIVPAKSVCGPVYCFTPSPVVVGTTDRSGAPTYSWGANDTDVFVLNNTRPPLGNWFG
CTQMNSTGFTKVCGAPPCVIGGVGNNTLLCPTDCFRKHPEATYSRCGSGPWITPRCMVDYPYRLWHYPCTINY
TIFKVRMYVGGVEHRLEAACNWTRGERCDLEDRDRSE

E2Δ2-his mature protein

ETHVTGGNAGRTTAGLVGLLTPGAKQNIQLINTNGSWHINSTALNCNESLNTGWLAGLFYQHKFNSSGCPERL
ASCGSSGCWHYPPRPCGIVPAKSVCGPVYCFTPSPVVVGTTDRSGAPTYSWGANDTDVFVLNNTRPPLGNWFG
CTWMNSTGFTKVCGA[[CVIGGVGNNTLLCPTDCFRKHPEATYSRCGSGPWITPRCMVDYPYRLWHYPCTINY
TIFKVRMYVGGVEHRLEAACNWTRGERCDLEDRDRSE

E2Δ3-his mature protein

ATHVTGGNAGRTTAGLVGLLTPGAKQNIQLINTNGSWHINSTALNCNESLNTGWLAGLFYQHKFNSSGCPERL
ASCRRLTDFAQGWGPISYANGSGLDERPYCWHYPPRPCGIVPAKSVCGPVYCFTPSPVVVGTTDRSGAPTYSW
GANDTDVFVLNNTRPPLGNWFGCTWMNSTGFTKVCGAPPCGSSGCPTDCFRKHPEATYSRCGSGPWITPRCMV
DYPYRLWHYPCTINYTIFKVRMYVGGVEHRLEAACNWTRGERCDLEDRDRSE

E2Δ12-his mature protein

ETHQNIQLINTNGSWHINSTALNCNESLNTGWLAGLFYQHKFNSSGCPERLASCGSSGCWHYPPRPCGIVPAK
SVCGPVYCFTPSPVVVGTTDRSGAPTYSWGANDTDVFVLNNTRPPLGNWFGCTWMNSTGFTKVCGAPPCVIGG
VGNNTLLCPTDCFRKHPEATYSRCGSGPWITPRCMVDYPYRLWHYPCTINYTIFKVRMYVGGVEHRLEAACNW
TRGERCDLEDRDRSE

E2Δ13-his mature protein

ETHQNIQLINTNGSWHINSTALNCNESLNTGWLAGLFYQHKFNSSGCPERLASCRRLTDFAQGWGPISYANGS
GLDERPYCWHYPPRPCGIVPAKSVCGPVYCFTPSPVVVGTTDRSGAPTYSWGANDTDVFVLNNTRPPLGNWFG
CTWMNSTGFTKVCGAPPCGSSGCPTDCFRKHPEATYSRCGSGPWITPRCMVDYPYRLWHYPCTINYTIFKVRM
YVGGVEHRLEAACNWTRGERCDLEDRDRSE

E2Δ23-his mature protein

ETHVTGGNAGRTTAGLVGLLTPGAKQNIQLINTNGSWHINSTALNCNESLNTGWLAGLFYQHKFNSSGCPERL
ASCGSSGCWHYPPRPCGIVPAKSVCGPVYCFTPSPVVVGTTDRSGAPTYSWGANDTDVFVLNNTRPPLGNWFG

```
CTWMNSTGFTKVCGAPPCGSSGCPTDCFRKHPEATYSRCGSGPWITPRCMVDYPYRLWHYPCTINYTIFKVRM
YVGGVEHRLEAACNWTRGERCDLEDRDRSE
```

E2Δ123-his mature protein

```
ETHQNIQLINTNGSWHINSTALNCNESLNTGWLAGLFYQHKFNSSGCPERLASCGSSGCWHYPPRPCGIVPAK
SVCGPVYCFTPSPVVVGTTDRSGAPTYSWGANDTDVFVLNNTRPPLGNWFGCTWMNSTGFTKVCGAPPCGSSG
CPTDCFRKHPEATYSRCGSGPWITPRCMVDYPYRLWHYPCTINYTIFKVRMYVGGVEHRLEAACNWTRGERCD
LEDRDRSE
```

Cell Culture

FreeStyle™ 293-F cells (Invitrogen) were cultured in FreeStyle™ Expression Medium (Invitrogen) supplemented with penicillin/streptomycin/fungizone (Invitrogen). All cells were maintained at 37° C. in humidified incubators with an atmosphere of 8% $CO_2$.

Transient Protein Expression

Transient expression of each of the E2-his proteins was carried out in FreeStyle™ 293-F cells by transfection with the pcDNA3.1-based expression plasmids and 293fectin transfection reagent (Invitrogen) according to the manufacturer's instructions. The cells in a total volume of 180 ml were transfected at a final concentration of $1 \times 10^6$ viable cells/ml and incubated in a sterile shaker flask (Corning) for 5 days on an orbital shaker (IKA) rotating at 150 rpm in a 37° C. humidified incubator with an atmosphere of 8% $CO_2$. Twenty-four hours after transfection the cell cultures were supplemented with Tryptone N1 (Organotechnie, France) to a final concentration of 0.5% v/v. Typically the cell cultures were harvested 5 days after transfection. Protein expression was examined by electrophoresis of a sample of cell culture supernatant using 4-20% Tris-Glycine SDS polyacrylamide gel and the proteins visualised by staining with Coomassie Blue reagent. For protein purification, cell culture supernatants were harvested by centrifugation at 2500 rpm and then passed through a 0.45 μM filter (Nalgene) prior to chromatography.

Purification of Expressed Wild Type and Variant HCV E2-his Proteins.

Following filtration the cell culture supernatants were subjected to immobilised metal affinity chromatography (IMAC) using Nickel sepharose to purify the wild type and variant E2-his proteins.

The purification procedure is described below:

1. Buffers:

Ni-MAC Buffer A

- 50 mM $NaH_2PO_4$ pH 8.0
- 300 mM NaCl
- 10 mM imidazole

Ni-MAC Buffer B (Elution)

- 50 mM $NaH_2PO_4$ pH 8.0
- 300 mM NaCl
- 500 mM imidazole

2. Protocol:
   1. Procedures 2 to 6 were carried out at 4-8° C.
   2. 1 ml Ni Sepharose 6 Fast Flow resins (GE Healthcare) in a 10 ml Poly-Prep columns (Bio-Rad) were washed with 5 volumes of $ddH_2O$.
   3. The columns were equilibrated with 10 ml Ni-MAC Buffer A.
   4. Samples were loaded onto the columns, and breakthrough (B/T) collected.
   5. The columns were washed with 10 ml Ni-MAC Buffer A.
   6. The proteins were eluted with 5 ml Ni-MAC Buffer B (Elution) and 1 ml fractions collected.
   7. Peak fractions were identified using 96-well plate format Bradford Assay and Coomassie-stained SDS-polyacrylamide gel electrophoresis (SDS-PAGE) gels.
   8. Peak fractions were pooled and dialysed in 1×PBS overnight at 4° C.
   9. Following dialysis protein concentrations were determined using 96-well plate format Bradford Assay and 1 mg/ml BSA for a standard curve.

Construction of Con1 $E2_{RBD}$-his and JFH1 $E2_{RBD}$-myc cDNAs and Secreted Expression of the Encoded Proteins in Mammalian Cells.

Generation of cDNA Expression Plasmids Encoding Con1 $E2_{RBD}$-his and JFH1 $E2_{RBD}$-myc.

cDNAs encoding Con1 E2 (HCV Con1 polyprotein residues 384 to 661; Genbank accession number AJ238799) and JFH1 E2 (HCV JFH1 polyprotein residues 384 to 665; Genbank accession number AB047369), were prepared by PCR using Expand-Hifi polymerase (Roche) and the primers indicated in Table 17. The forward primers encoded an NheI restriction site for incorporation in-frame at the 5' ends of the cDNAs. The reverse primers encoded (His)6 (SEQ ID NO: 108) and c-myc epitope tags for addition in-frame to the 3' ends of Con1 and JFH1 cDNAs, respectively, and for both cases were followed by a TAG translation termination codon and an Xba1 restriction site. The specific PCR parameters were as follows: 5 minutes of denaturation at 95° C. was followed by 30 cycles of 92° C. for 1 min, 55° C. for 1 min and 72° C. for 2 minutes with a final 10 minute incubation at 72° C. The cDNAs were cloned downstream of a tissue plasminogen activator signal peptide in vector pcDNA3 to facilitate secretion of the expressed proteins. The nucleotide sequences of the cloned cDNAs were verified by using Big Dye Terminator v3.1 Cycle Sequencing and an Applied Biosystems Automated Sequencer.

Transient Expression of Con1 $E2_{RBD}$-his and JFH1 $E2_{RBD}$-myc

HEK 293T cells (350,000 cells per well of 6-well culture plates) were transfected with Con1 $E2_{RBD}$-his and JFH1 $E2_{RBD}$-myc expression vectors using Fugene 6 (Roche). At 8-h post transfection, the transfection medium was replaced with Optimem (Invitrogen) and the cells incubated for 3 days at 37° C. in a humidified atmosphere containing 5% $CO_2$. The tissue culture fluid was clarified by centrifugation at 1500 rpm for 10 min followed by filtration through 0.45-μm-pore-size syringe filters.

Biochemical and Functional Analysis of Wild Type and Variant E2-his Proteins.

BLUE-Native PAGE The oligomerization status of the purified E2-his proteins was analysed using blue native polycrylamide gel electrophoresis (BN-PAGE). Ten μg of each protein was added to 10 μl of solubilization buffer and 1.5 μl of sample buffer and loaded onto 5-15% gradient separating gels containing a 4% stacking gel. The gels were electrophoresed at 4° C. at 100 volts until the dye front entered the stacking gel. The voltage was then increased to 200 volts until the dye front migrated to the bottom of the gel. Electrophoresis was conducted for 1.5 h with 1× cathode buffer containing 0.01% Serva G in the upper reservoir, followed by electrophoresis for 1-1.5 h in 1× cathode buffer without Serva G. The lower reservoir contained 1× anode buffer. After electrophoresis, the gels were destained overnight and scanned in an Odyssey scanner at 680 nm.

The solutions used for BN-PAGE are as follows:
Polyacrylamide Gels:

|  | 4% stacker | 5% separating gel | 15% separating gel |
| --- | --- | --- | --- |
| 40% acrylamide | 0.299 ml | 0.262 ml | 0.787 ml |
| 3x gel buffer | 1 ml | 0.7 ml | 0.7 ml |
| 75% Glycerol |  | 0.14 ml | 0.62 ml |
| water | 1.72 ml | 0.978 ml | 0 |
| TEMED | 6 μl | 2 μl | 2 μl |
| 5% ammonium persulphate | 32 μl | 11 μl | 11 μl |

Other Solutions:
- 3× Gel Buffer. 150 mM BisTris-HCl, 0.5M 6-amino caproic acid, pH 7.0
- 10× Cathode buffer. 0.5M Tricine, 150 mM BisTris
- 5× Anode buffer. 0.25M BisTris-HCl, pH 7.0
- 2×BisTrisACA. 200 mM BisTris-HCl, 1M 6-amino-caproic acid, pH 7.0.
- Sample buffer. 50 mg ServaG, 500 μl 2×BisTrisACA, 400 μl 75% sucrose and 1000 water.
- Solubilization buffer. 0.5M 6-amino-caproic acid, 20 mM BisTris, 2 mM EDTA, pH 7.0, 1% Triton X-100, 10% glycerol.
- Destain. 10% acetic acid, 10% methanol, 80% water.

Immunodetection of E2-his Proteins.

Samples of the purified E2-his proteins were subjected to reducing SDS-PAGE followed by electrophoretic transfer to nitrocellulose membrane. E2-his proteins were detected with a non-conformation dependent E2 specific monoclonal antibody followed by goat anti-mouse immunoglobulin coupled to Alexa fluor 680 nm (Invitrogen). Immunoblots were scanned in an Odyssey detection system.

CD81 Binding Properties.

The ability of the E2-his proteins to interact with the HCV cellular receptor CD81 was examined using a solid phase enzyme immunoassay. Enzyme immunoassay plates (Nunc Maxisorb®) were coated with maltose binding protein fused to the recombinant large extracellular loop of CD81 (residues 113-201) at 5 μg/ml in PBS overnight at 4° C. Coating solution was removed and unoccupied sites blocked with bovine serum albumin (10 mg/ml) in PBS (BSA$_{10}$PBS) for 1 h at room temperature. Plates were washed 4 times with PBS containing 0.05% Tween 20 (PBST). 50 ng E2-his proteins were serially diluted in a 50 μl PBS containing 5 mg/ml bovine serum albumin (BSA$_5$PBST) and incubated for 2 h. Bound E2-his protein was detected using an E2 specific monoclonal antibody followed by rabbit anti-mouse immunoglobulins coupled to horse radish peroxidase (Dako). Plates were developed using tetramethylbenzidine hydrochloride substrate and stopped by the addition of 1M HCl. Absorbance values were measured at 450 nm and the background at 620 nm. subtracted in a Fluostar plate reader (BMG technologies).

Immunogenicity in Mice of Wild-Type and Variant E2-his Proteins.

Immunization Protocol.

Groups of 10 7-8 week old female Balb/c mice were immunised with purified E2-his wild type and variant proteins formulated with ISCOMATRIX® adjuvant (Pearse and Drane, 2005) (Table 18). Each mouse dose contained 10 μg specific protein and 5 μg ISCOMATRIX® adjuvant in a 0.1 ml volume. Mice were dosed subcutaneously three times at three-weekly intervals and bleeds taken 1 day prior to the first dose and at one week after both the second and third doses.

Enzyme-Linked Immunosorbent Assay (ELISA)

The immune mouse sera were examined for the presence of anti-E2 antibodies in ELISA. The E2-his, Con1 E2$_{RBD}$-myc or JFH1 E2$_{RBD}$-myc proteins were captured on 96 well Maxisorb microtitre plates (Nunc) using Galanthis nivalis (GNA) lectin. Plates were coated with GNA lectin at 5 μg/ml in PBS overnight at 4° C. Unoccupied sites were blocked with 100 μl BSA$_{10}$PBS for 1 h at room temperature. After washing the plates 4 times with PBST, the E2 proteins were applied in 50 μl BSA$_5$PBST and incubated for 1 h at room temperature. After washing the plates 4 times with PB ST, serial dilutions of mouse sera were applied in a 50 μl volume of BSA$_5$PBST and incubated for 1 h room temperature. Bound immunoglobulins were detected with rabbit anti-mouse immunoglobulin coupled to horseradish peroxidase and developed using tetramethylbenzidine hydrochloride substrate and stopped by the addition of 1M HCl. A Fluostar plate reader (BMG technologies) was used to measure the absorbance at 450 nm and the background at 620 nm. The background was subtracted from the absorbance to generate the binding curves.

Neutralization Assays

The abilities of immune and control mouse sera to neutralize a single cycle of infection by HCV glycoprotein-pseudotyped HIV-1 luciferase reporter viruses were determined as follows. HCV glycoprotein-pseudotyped HIV-1 luciferase reporter viruses were prepared by cotransfection of HEK-293T monolayers (350,000 cells per well of 6-well culture dishes) with pE1E2 and pNL4.3LUCR–E– plasmids (Drummer et al., 2003). After 3 days incubation at 37° C. in a humidified atmosphere containing 5% CO$_2$, the culture supernatants were filtered through 0.45 μm sterile syringe filters (Sartorius). Serial 5-fold dilutions of heat-inactivated immune and control mouse sera were preincubated with HCV glycoprotein-pseudotyped HIV-1 luciferase reporter viruses (1 h) and then added to quadruplicate Huh7 cell monolayers in 48-well tissue culture plates. Following a 4 h incubation (37° C., 5% CO$_2$) the cells were washed with PBS and the medium replaced. After an additional 3-day incubation (37° C. in 5% $CO_2$), the cells were lysed, the lysates clarified by centrifugation and then assayed for luciferase activity (Promega) in a Fluostar (BMG) fitted with luminescence optics. The neutralization titres of individual sera were determined as the serum dilution giving 80% neutralization compared to HCV glycoprotein-pseudotyped HIV-1 luciferase reporter virus preincubated with medium alone.

TABLE 7

Pair-wise statistical comparison of antibody titres reactive to solid-phase E2-his antigen obtained after $2^{nd}$ vaccination.

| | Immunogen Group | | | | | | |
|---|---|---|---|---|---|---|---|
| | E2 Δ1-his | E2 Δ2-his | E2 Δ3-his | E2 Δ12-his | E2 Δ13-his | E2 Δ23-his | E2 Δ123-his |
| E2-his | 0.06 | 0.96 | 0.25 | 0.26 | 0.37 | 0.6 | 0.08 |
| E2 Δ1-his | | 0.06 | 0.27 | 0.09 | 0.034 | 0.014 | 0.04 | p values calculated using student's t test.

TABLE 8

Pair-wise statistical comparison of antibody titres reactive to solid phase E2 Δ123-his protein antigen obtained after $2^{nd}$ vaccination.

| | Immunogen Group | | | | | | |
|---|---|---|---|---|---|---|---|
| | E2 Δ1-his | E2 Δ2-his | E2 Δ3-his | E2 Δ12-his | E2 Δ13-his | E2 Δ23-his | E2 Δ123-his |
| E2-his | 0.04 | 0.96 | 0.02 | 0.02 | 0.09 | 0.077 | 0.003 |
| E2 Δ1-his | | 0.04 | 0.09 | 0.12 | 0.06 | 0.06 | 0.17 | p values calculated using student's t test.

TABLE 9

Pair-wise statistical comparison of antibody titres reactive to solid-phase E2-his protein antigen obtained after $3^{rd}$ vaccination.

| | Immunogen Group | | | | | | |
|---|---|---|---|---|---|---|---|
| | E2 Δ1-his | E2 Δ2-his | E2 Δ3-his | E2 Δ12-his | E2 Δ13-his | E2 Δ23-his | E2 Δ123-his |
| E2-his | 0.02 | 0.003 | 0.002 | 0.04 | 0.002 | 0.02 | 0.11 |
| E2 Δ1-his | | 0.1 | 0.021 | 0.58 | 0.44 | 0.9 | 0.17 | p values calculated using student's t test assuming unequal variances.

TABLE 10

Pair-wise statistical comparison of antibody titres reactive to solid-phase E2 Δ123-his protein antigen obtained after $3^{rd}$ vaccination.

| | Immunogen | | | | | | |
|---|---|---|---|---|---|---|---|
| | E2 Δ1-his | E2 Δ2-his | E2 Δ3-his | E2 Δ12-his | E2 Δ13-his | E2 Δ23-his | E2 Δ123-his |
| E2-his | 0.64 | 1 | 0.016 | 0.004 | 0.31 | 0.003 | 0.0007 |
| E2 Δ1-his | | 0.62 | 0.022 | 0.007 | 0.44 | 0.005 | 0.009 | p values calculated using student's t test assuming unequal variances.

TABLE 11

Statistical comparison of relative antibody titres obtained after 3rd vaccination against E2-his antigen and E2 Δ123-his antigen.

| | Immunogen | | | | | | | |
| --- | --- | --- | --- | --- | --- | --- | --- | --- |
| | E2 Δ1-his | E2 Δ2-his | E2 Δ3-his | E2 Δ12-his | E2 Δ13-his | E2 Δ23-his | E2 Δ123-his | E2-his |
| Mean antibody titre against E2-his ($\times 10^5$) | 1.16 | 0.81 | 0.68 | 1.31 | .71 | 1.19 | 1.54 | 2.26 |
| Mean antibody titre against E2 Δ123-his ($\times 10^5$) | 0.56 | 0.51 | 1.15 | 1.11 | 0.71 | 1.19 | 1.54 | 0.51 |
| p value | 0.005 | 0.045 | 0.06 | 0.46 | 1 | 1 | 1 | 0.0009 | p values calculated using student's t test assuming unequal variances.

TABLE 12

Pair-wise statistical comparison of antibody titres reactive to solid-phase Con1 $E2_{RBD}$-his protein antigen obtained after 3rd vaccination.

| | E2-his | E2 Δ1-his | E2 Δ2-his | E2 Δ3-his | E2 Δ12-his | E2 Δ13-his | E2 Δ23-his | E2 Δ123-his |
| --- | --- | --- | --- | --- | --- | --- | --- | --- |
| E2-his | | | | | | | | |
| E2 Δ1-his | 0.526 | | | | | | | |
| E2 Δ2-his | 0.0453 | 0.072 | | | | | | |
| E2 Δ3-his | 0.043 | 0.061 | 0.883 | | | | | |
| E2 Δ12-his | 0.0123 | 0.091 | 0.926 | 0.797 | | | | |
| E2 Δ13-his | 0.185 | 0.343 | 0.847 | 0.756 | 0.888 | | | |
| E2 Δ23-his | 0.173 | 0.568 | 0.284 | 0.238 | 0.217 | 0.534 | | |
| E2 Δ123-his | 0.0123 | 0.028 | 0.259 | 0.325 | 0.197 | 0.251 | 0.0499 | | p values calculated using student's t test assuming unequal variances.

TABLE 13

Pair-wise statistical comparison of antibody titres reactive to solid-phase JFH1 $E2_{RBD}$-myc protein antigen obtained after 3rd vaccination.

| | E2-his | E2 Δ1-his | E2 Δ2-his | E2 Δ3-his | E2 Δ12-his | E2 Δ13-his | E2 Δ23-his | E2 Δ123-his |
| --- | --- | --- | --- | --- | --- | --- | --- | --- |
| E2-his | | | | | | | | |
| E2 Δ1-his | 0.609 | | | | | | | |
| E2 Δ2-his | 0.148 | 0.511 | | | | | | |
| E2 Δ3-his | 0.159 | 0.253 | 0.371 | | | | | |
| E2 Δ12-his | 0.305 | 0.549 | 0.861 | 0.48 | | | | |
| E2 Δ13-his | 0.392 | 0.624 | 0.916 | 0.484 | 0.970 | | | |
| E2 Δ23-his | 0.123 | 0.287 | 0.492 | 0.652 | 0.705 | 0.702 | | |
| E2 Δ123-his | 0.058 | 0.084 | 0.117 | 0.406 | 0.154 | 0.156 | 0.209 | | p values calculated using student's t test assuming unequal variances.

TABLE 14

Mean 80% Neutralizing antibody titres and statistical comparison. p values were calculated using student's t test assuming unequal variances.

|  | Immunogen group | | | | |
| --- | --- | --- | --- | --- | --- |
|  | E2-his | E2 Δ1-his | E2 Δ23-his | E2 Δ123-his | No antigen |
| Mean neutralizing antibody titre | 908 | 7 | 140 | 413 | 26 |
| p value relative to E2-his |  | 0.044 | 0.08 | 0.29 | 0.048 |
| p value relative to E2 Δ1-his |  |  | 0.002 | 0.11 | 0.31 |

TABLE 15

Primers used for preparation of E2-his protein variant DNA sequences.

| Primer designation | Primer Sequence |
| --- | --- |
| HCV-1 | 5' TATAGCTAGCGCCACCATGAACCCCCTGC 3' |
| HCV-2 | 5' CTGGATGTTCTGGTGGGTCTCGGCCAG 3' |
| HCV-3 | 5' GCCGAGACCCACCAGAACATCCAGCTG 3' |
| HCV-4 | 5' CGCTGCTGCCGCAGGAGGCGAG 3' |
| HCV-4a | 5' GTAGTGCCAGCAGCCGCTGCTGCCGCAGGAGGCGAGCCTCTCGG 3' |
| HCV-5 | 5' GGCAGCAGCGGCTGCTGGCACTAC 3' |
| HCV-5a | 5' CTCGCCTCCTGCGGCAGCAGCGGCTGCTGGCACTACCCCCCAGA 3' |
| HCV-6a | 5' GTCGGTGGGGCAGCCGCTGCTGCCGCAGGGAGGGGCGCCACACA C 3' |
| HCV-7a | 5' GCCCCTCCCTGCGGCAGCAGCGGCTGCCCCACCGACTGCTTTAGG 3' |
| HCV-8 | 5' TCTGCTCGAGTTATCAGTGGTGATGGTGGTGG 3' |
| HCV-11 | 5' CTCTCGTTGCAGTTCAGGGCGGTGCTG 3' |
| HCV-12 | 5' CAGCACCGCCCTGAACTGCAACGAGAG 3' |

TABLE 16

| Primer combinations used for preparation of E2-his protein variant DNA sequences. | |
|---|---|
| E2 protein | Primer combination |
| E2Δ1-his | HCV-1 HCV-3 HCV-8 |
| E2Δ2-his | HCV-1 HCV-11 HCV-12 HCV-8 |
| E2Δ3-his | HCV-1 HCV-6a HCV-7a HCV-8 |
| E2Δ12-his | HCV-1 HCV-2 HCV-3 HCV-4 HCV-5 |
| E2Δ13-his | HCV-1 HCV-6a HCV-7a HCV-8 |
| E2Δ23-his | HCV-1 HCV-5a HCV-4A HCV-6A HCV-7A HCV-8 |
| E2Δ123-his | HCV-1 HCV-6a HCV-7a HCV-8 |

TABLE 17

Primers used for preparation of Con1 $E2_{RBD}$-bis and JFH1 $E2_{RBD}$-myc DNA sequences

| $E2_{RBD}$ construct | | Primer Sequence | RE site | Epitope tag |
|---|---|---|---|---|
| Con1 $E2_{RBD}$-bis | Forward primer | 5'-CAAGCTAGCggaacctatgtgacaggg | NheI | |
| | Reverse primer | 5'-CCCTCTAGATTAGTGGTGGTGGTGGTGGCCGCCCTCTGATCTGTCCCTGTC | XbaI | $His_6$ |
| JFH1 $E2_{RBD}$-myc | Forward primer | 5' CAAGCTAGCggcaccaccaccgttggaggc | NheI | |
| | Reverse primer | 5'CCGTCTAGActaattcagatcctcttctgagatgagtttttgttcagtactCTGACTCCTGTCCCTGTC | XbaI | myc |

TABLE 18

| Immunisation of mice with E2-his wild type and variant proteins formulated with ISCOMATRIX ® adjuvant Antigens | | |
|---|---|---|
| Group | Protein | ISCOMATRIX ® adjuvant |
| 1 | E2Δ1-his | + |
| 2 | E2Δ2-his | + |
| 3 | E2Δ3-his | + |
| 4 | E2Δ123-his | + |
| 5 | E2Δ12-his | + |
| 6 | E2Δ13-his | + |
| 7 | E2Δ23-his | + |
| 8 | E2-his | + |
| 9 | — | + |

REFERENCES

1. Anandarao, R., S. Swaminathan, S. Fernando, A. M. Jana, and N. Khanna (2006), "Recombinant multiepitope protein for early detection of dengue infections". *Clin. Vaccine Immunol.* 13:59-67.
2. Arai, R., W. Wriggers, Y. Nishikawa, T. Nagamune, and T. Fujisawa, (2004), "Conformations of variably linked chimeric proteins evaluated by synchrotron X-ray small-angle scattering". *Proteins* 57:829-38.
3. Argos, P. (1990), "An investigation of oligopeptides linking domains in protein tertiary structures and possible candidates for general gene fusion". *J. Mol. Biol.* 211: 943-58.
4. Bahrami, S., M. Duch, and F. S. Pedersen, (2007), "Ligand presentation on a synthetic flexible hinge in Moloney murine leukemia virus SU supports entry via a heterologous receptor". *Virology, B*363B:303-9.
5. Bartosch, B., Bukh, J., Meunier, J. C., Granier, C., Engle, R. E., Blackwelder, W. C., Emerson, S. U., Cosset, F. L. & Purcell, R. H. (2003a) In Vitro Assay For Neutralizing Antibody To Hepatitis C Virus: Evidence For Broadly Conserved Neutralization Epitopes. *Proc Natl Acad Sci USA,* 100, 14199-204.
6. Bartosch, B., Dubuisson, J. & Cosset, F. L. (2003b) Infectious Hepatitis C Virus Pseudo-Particles Containing Functional E1-E2 Envelope Protein Complexes. *J Exp Med,* 197, 633-642.
7. Bellamy-Mcintyre, A. K., C. S. Lay, S. Baar, A. L. Maerz, G. H. Talbo, H. E. Drummer, And P. Poumbourios, (2007), "Functional Links Between The Fusion Peptide-Proximal Polar Segment And Membrane-Proximal Region Of Human Immunodeficiency Virus Gp41 In Distinct Phases Of Membrane Fusion". *J. Biol. Chem.* 282:23104-16.
8. Deleersnyder, V., Pillez, A., Wychowski, C., Blight, K., Xu, J., Hahn, Y. S., Rice, C. M. & Dubuisson, J. (1997) Formation Of Native Hepatitis C Virus Glycoprotein Complexes. *J Virol,* 71, 697-704.
9. Dipti, C. A., S. K. Jain, And K. Navin, (2006), "A Novel Recombinant Multiepitope Protein As A Hepatitis C Diagnostic Intermediate Of High Sensitivity And Specificity". *Protein Expr. Purif.* 47:319-28.
10. Drummer, H. E., Boo, I., Maerz, A. L. & Poumbourios, P. (2006) A Conserved Gly436-Trp-Leu-Ala-Gly-Leu-Phe-Tyr Motif (SW ID NO: 107) In Hepatitis C Virus Glycoprotein E2 Is a Determinant of Cd81 Binding and Viral Entry. *J Virol,* 80, 7844-53.
11. Drummer, H. E., Maerz, A. & Poumbourios, P. (2003) Cell Surface Expression Of Functional Hepatitis C Virus E1 And E2 Glycoproteins. *Febs Lett,* 546, 385-90.
12. Drummer, H. E., Wilson, K. A. & Poumbourios, P. (2002) Identification Of The Hepatitis C Virus E2 Glycoprotein Binding Site On The Large Extracellular Loop Of Cd81. *J Virol,* 76, 11143-7.
13. Dubuisson, J., Hsu, H. H., Cheung, R. C., Greenberg, H. B., Russell, D. G. & Rice, C. M. (1994) Formation And Intracellular Localization Of Hepatitis C Virus Envelope Glycoprotein Complexes Expressed By Recombinant Vaccinia And Sindbis Viruses. *J Virol,* 68, 6147-60.
14. George, R. A., And J. Heringa, (2002), "An Analysis Of Protein Domain Linkers: Their Classification And Role In Protein Folding". *Protein Eng.* 15:871-9.
15. Grollo, L., J. Torresi, H. Drummer, W. Zeng, N. Williamson, and D. C. Jackson, (2006). "Exploiting information inherent in binding sites of virus specific antibodies:

design of an HCV vaccine candidate cross-reactive with multiple genotypes". *Antivir. Ther.* 11:1005-1014.
16. He, J. & Landau, N. R. (1995) Use Of A Novel Human Immunodeficiency Virus Type 1 Reporter Virus Expressing Human Placental Alkaline Phosphatase To Detect An Alternative Viral Receptor. *J Virol,* 69, 4587-92.
17. Horton, R. M., Hunt, H. D., Ho, S. N., Pullen, J. K. & Pease, L. R. (1989) Engineering Hybrid Genes Without The Use Of Restriction Enzymes: Gene Splicing By Overlap Extension. *Gene,* 77, 61-8.
18. Keck, Z. Y., Op De Beeck, A., Hadlock, K. G., Xia, J., Li, T. K., Dubuisson, J. & Foung, S. K. (2004) Hepatitis C Virus E2 Has Three Immunogenic Domains Containing Conformational Epitopes With Distinct Properties And Biological Functions. *J Virol,* 78, 9224-32.
19. Levy, S., Todd, S. C. & Maecker, H. T. (1998) Cd81 (Tapa-1): A Molecule Involved In Signal Transduction And Cell Adhesion In The Immune System. *Annu Rev Immunol,* 16, 89-109.
20. Lindenbach, B. D., Evans, M. J., Syder, A. J., Wolk, B., Tellinghuisen, T. L., Liu, C. C., Maruyama, T., Hynes, R. O., Burton, D. R., Mckeating, J. A. & Rice, C. M. (2005) Complete Replication Of Hepatitis C Virus In Cell Culture. *Science.*
21. Lohmann, V., Korner, F., Koch, J., Herian, U., Theilmann, L. & Bartenschlager, R. (1999) Replication Of Subgenomic Hepatitis C Virus Rnas In A Hepatoma Cell Line. *Science,* 285, 110-3.
22. Petracca, R., Falugi, F., Galli, G., Norais, N., Rosa, D., Campagnoli, S., Burgio, V., Di Stasio, E., Giardina, B., Houghton, M., Abrignani, S. & Grandi, G. (2000) Structure-Function Analysis Of Hepatitis C Virus Envelope-Cd81 Binding. *J Virol,* 74, 4824-30.
23. Pearse, M. J. and Drane, D, (2005). "ISCOMATRIX® adjuvant for antigen delivery". *Adv. Drug Del. Rev.* 57:465-474.
24. Pileri, P., Uematsu, Y., Campagnoli, S., Galli, G., Falugi, F., Petracca, R., Weiner, A. J., Houghton, M., Rosa, D., Grandi, G. & Abrignani, S. (1998) Binding Of Hepatitis C Virus To Cd81. *Science,* 282, 938-41.
25. Sabourin, M., C. T. Tuzon, T. S. Fisher, And V. A. Zakian, (2007), "A Flexible Protein Linker Improves The Function Of Epitope-Tagged Proteins In *Saccharomyces Cereviseae"*. *Yeast,* 24:39-45.
26. Sambrook, J. & Russel, D. (2001) *Molecular Cloning,* Cshl Press.
27. Scarselli, E., Ansuini, H, Cerino, R., Roccasecca, R. M., Acali, S., Filocamo, G., Traboni, C., Nicosia, A., Cortese, R. & Vitelli, A. (2002) The Human Scavenger Receptor Class B Type I Is A Novel Candidate Receptor For The Hepatitis C Virus. *Embo J,* 21, 5017-25.
28. Wakita, T., Pietschmann, T., Kato, T., Date, T., Miyamoto, M., Zhao, Z., Murthy, K., Habermann, A., Krausslich, H. G., Mizokami, M., Bartenschlager, R. & Liang, T. J. (2005) Production Of Infectious Hepatitis C Virus In Tissue Culture From A Cloned Viral Genome. *Nat Med,* 11, 791-6.
29. Wyatt, R., J. Moore, M. Accola, E. Desjardin, J. Robinson, And J. Sodroski, (1995), "Involvement Of The V1/V2 Variable Loop Structure In The Exposure Of Human Immunodeficiency Virus Type 1 Gp120 Epitopes Induced By Receptor Binding". *J. Virol,* 69:6723-33.
30. Yanagi, M., Purcell, R. H., Emerson, S. U. & Bukh, J. (1997) Transcripts From A Single Full-Length Cdna Clone Of Hepatitis C Virus Are Infectious When Directly Transfected Into The Liver Of A Chimpanzee. *Proc Natl Acad Sci USA,* 94, 8738-43.
31. Yang, W. Y., And M. Gruebele, (2006). "Binary And Ternary Aggregation Within Tethered Protein Constructs". *Biophys. J.* 90:2930-7.
32. Zhong, J., Gastaminza, P., Cheng, G., Kapadia, S., Kato, T., Burton, D. R., Wieland, S. F., Uprichard, S. L., Wakita, T. & Chisari, F. V. (2005) Robust Hepatitis C Virus Infection In Vitro. *Proc Natl Acad Sci USA,* 102, 9294-9.

The invention claimed is:

1. An isolated modified hepatitis C virus (HCV) E2 glycoprotein comprising a modification in the HCV-E2 receptor-binding domain (RBD) ranging from amino acid residues 384 to 661, wherein, in the modified glycoprotein, at least the intergenotypic variable region (igVR) of the HCV-E2 receptor-binding domain is deleted, and wherein the modified glycoprotein binds to the HCV receptor CD81.

2. A modified glycoprotein according to claim 1, wherein the HVR1 variable region also is deleted and is optionally replaced with a flexible linker sequence.

3. A modified glycoprotein according to claim 1, wherein the HVR2 variable region also is deleted and is optionally replaced with a flexible linker sequence.

4. A modified glycoprotein according to claim 1, wherein the variable regions HVR1 and HVR2 also are deleted and each optionally is replaced with a flexible linker sequence.

5. A modified glycoprotein according to claim 2, wherein the HVR1 variable region is replaced with a flexible linker sequence.

6. A modified glycoprotein according to claim 3, wherein the HVR2 variable region is replaced with a flexible linker sequence.

7. A modified glycoprotein according to claim 4, wherein the variable regions HVR1 and HVR2 are replaced with flexible linker sequences.

8. A modified glycoprotein according to claim 5, wherein the flexible linker sequence comprises a Gly-Ser-Ser-Gly (GSSG) sequence (SEQ ID NO: 95).

9. A modified glycoprotein according to claim 5, wherein the flexible linker sequence, comprises a Glu-Thr-His-Gly-Ser-Ser-Gly (ETHGSSG) sequence (SEQ ID NO: 109).

10. A composition comprising a modified HCV E2 glycoprotein according to claim 1, together with a pharmaceutically acceptable carrier or diluent.

11. A composition according to claim 10, further comprising an adjuvant.

12. An agent for eliciting an immune response in a patient, which comprises a modified HCV E2 glycoprotein according to claim 1.

13. An agent for therapeutic treatment of HCV infection in a patient, which comprises a modified HCV E2 glycoprotein according to claim 1.

14. A method of eliciting an immune response in a patient, which comprises administration to the patient of an effective amount of a modified HCV E2 glycoprotein according to claim 1.

15. A method according to claim 14, wherein the patient is a human.

16. A method for therapeutic treatment of HCV infection in a patient, which comprises administration to the patient of an effective amount of a modified HCV E2 glycoprotein according to claim 1.

17. A method according to claim 16, wherein the patient is a human.

* * * * *

SEQUENCE LISTING

<160> NUMBER OF SEQ ID NOS: 118

<210> SEQ ID NO 1
<211> LENGTH: 32
<212> TYPE: DNA
<213> ORGANISM: Artificial Sequence
<220> FEATURE:
<223> OTHER INFORMATION: Description of Artificial Sequence: Synthetic primer

<400> SEQUENCE: 1
ccgaagcttc caccatggga gtggagggct gc                32

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 2
ggctctagat tagtacacgg agctgttccg                30

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
ggtggaattc tggcaacagg gaaccttcct gg                                      32

<210> SEQ ID NO 4
<211> LENGTH: 54
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gctttcattg caattcaagg ccgtgccgct actaccgtgg gtttccgcgt cgac             54

<210> SEQ ID NO 5
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
ccgtctagat tacgcctccg cttgggatat gag                                    33

<210> SEQ ID NO 6
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
ggtagtagcg gcacggcctt gaattgcaat gaaagcctta acacc                       45

<210> SEQ ID NO 7
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
ggtggaattc tggcaacagg gaaccttcct gg                                     32

<210> SEQ ID NO 8
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gtagtgccag cagtaggggc cgctactacc aaggcgtcgg cagctggcca acctctc          57

<210> SEQ ID NO 9
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
ccgtctagat tacgcctccg cttgggatat gag                                  33

<210> SEQ ID NO 10
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ggtagtagcg gcccctactg ctggcactac cctccaagac cttgtggc                  48

<210> SEQ ID NO 11
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
ggtggaattc tggcaacagg gaaccttcct gg                                   32

<210> SEQ ID NO 12
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gcaatcagtg gggcagagca agccgctact accgatgaca caaggggggcg ctccgcacac    60

<210> SEQ ID NO 13
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
ccgtctagat tacgcctccg cttgggatat gag                                  33

<210> SEQ ID NO 14
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
ggtagtagcg gcttgctctg ccccactgat tgcttccgc                            39

```
<210> SEQ ID NO 15
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ggtggaattc tggcaacagg gaaccttcct gg                                    32

<210> SEQ ID NO 16
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
ttggatgttc tggccgctac taccgtgggt ttccgcgtcg ac                         42

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ccgtctagat tacgcctccg cttgggatat gag                                   33

<210> SEQ ID NO 18
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
ggtagtagcg gccagaacat ccaactgatc aacacc                                36

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggtggaattc tggcaacagg gaaccttcct gg                                    32

<210> SEQ ID NO 20
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ttggatgttc tggccgctac taccgtgggt ttccgcgtcg ac                         42

<210> SEQ ID NO 21
```

```
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccgtctagat tacgcctccg cttgggatat gag                                    33

<210> SEQ ID NO 22
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
ggtagtagcg gccagaacat ccaactgatc aacacc                                 36

<210> SEQ ID NO 23
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ggtggaattc tggcaacagg gaaccttcct gg                                     32

<210> SEQ ID NO 24
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
gtagtgccag cagccgctac taccgcagct ggccaacctc tc                          42

<210> SEQ ID NO 25
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
ccgtctagat tacgcctccg cttgggatat gag                                    33

<210> SEQ ID NO 26
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggtagtagcg gctgctggca ctaccctcca agaccttgtg gc                          42

<210> SEQ ID NO 27
<211> LENGTH: 32
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
ggtggaattc tggcaacagg gaaccttcct gg                                    32

<210> SEQ ID NO 28
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
gcaatcagtg gggcagccgc tactaccaca aggggggcgct ccgcacac                   48

<210> SEQ ID NO 29
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
ccgtctagat tacgcctccg cttgggatat gag                                   33

<210> SEQ ID NO 30
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtagtagcg gctgccccac tgattgcttc cgc                                   33

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
caagctagcg aaacccacgg tagtagcggc                                       30

<210> SEQ ID NO 32
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ccgtctagac taattcagat cctcttctga gatgagtttt tgttcagtac tctcggacct      60
gtccctgtc                                                              69

<210> SEQ ID NO 33
```

```
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
caagtcagcg aaacccacgg tagtagcggc                                        30

<210> SEQ ID NO 34
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
ccgtctagac taattcagat cctcttctga gatgagtttt tgttcagtac tctcggacct       60
gtccctgtc                                                               69

<210> SEQ ID NO 35
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
ccagtcagcg aaacccacgt caccggggga aatgc                                  35

<210> SEQ ID NO 36
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
ccgtctagac taattcagat cctcttctga gatgagtttt tgttcagtac tctcggacct       60
gtccctgtc                                                               69

<210> SEQ ID NO 37
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37
ccagctagcg aaacccacgt caccggggga aatgc                                  35

<210> SEQ ID NO 38
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
ccgtctagac taattcagat cctcttctga gatgagtttt tgttcagtac tctcggacct       60
```

```
gtccctgtc                                                            69

<210> SEQ ID NO 39
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
caagtcagcg aaacccacgg tagtagcggc                                     30

<210> SEQ ID NO 40
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
ccgtctagac taattcagat cctcttctga gatgagtttt tgttcagtac tctcggacct    60
gtccctgtc                                                            69

<210> SEQ ID NO 41
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
caagctagcg aaacccacgg tagtagcggc                                     30

<210> SEQ ID NO 42
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ccgtctagac taattcagat cctcttctga gatgagtttt tgttcagtac tctcggacct    60
gtccctgtc                                                            69

<210> SEQ ID NO 43
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43
ccagctagcg aaacccacgt caccggggga aatgc                               35

<210> SEQ ID NO 44
<211> LENGTH: 69
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 44
ccgtctagac taattcagat cctcttctga gatgagtttt tgttcagtac tctcggacct        60
gtccctgtc                                                                69

<210> SEQ ID NO 45
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
caagctagcg aaacccacgg tagtagcggc                                         30

<210> SEQ ID NO 46
<211> LENGTH: 69
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
ccgtctagac taattcagat cctcttctga gatgagtttt tgttcagtac tctcggacct        60
gtccctgtc                                                                69

<210> SEQ ID NO 47
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
ggtggaattc tggcaacagg gaaccttcct gg                                      32

<210> SEQ ID NO 48
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gctttcattg cagccgctac taccgtgggt ttcgcgtcg ac                            42

<210> SEQ ID NO 49
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 49
ccgtctagat tacgcctccg cttgggatat gag                                     33

<210> SEQ ID NO 50
<211> LENGTH: 33
<212> TYPE: DNA

<213> ORGANISM: Artificial Sequence
<220> FEATURE:
<223> OTHER INFORMATION: Description of Artificial Sequence: Synthetic
      primer

<400> SEQUENCE: 50
ggtagtagcg gctgcaatga aagccttaac acc                33

<210> SEQ ID NO 51
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
ggtggaattc tggcaacagg gaaccttcct gg                 32

<210> SEQ ID NO 52
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ttggatgttc tggccgctac taccgtgggt ttccgcgtcg ac       42

<210> SEQ ID NO 53
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
ccgtctagat tacgcctccg cttgggatat gag                33

<210> SEQ ID NO 54
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
ggtagtagcg gccagaacat ccaactgatc aacacc             36

<210> SEQ ID NO 55
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
ggtggaattc tggcaacagg gaaccttcct gg                 32

<210> SEQ ID NO 56
<211> LENGTH: 42
<212> TYPE: DNA
<213> ORGANISM: Artificial Sequence

```
<220> FEATURE:
<223> OTHER INFORMATION: Description of Artificial Sequence: Synthetic
      primer

<400> SEQUENCE: 56
gtagtgccag cagccgctac taccgcagct ggccaacctc tc                          42

<210> SEQ ID NO 57
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ccgtctagat tacgcctccg cttgggatat gag                                    33

<210> SEQ ID NO 58
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
ggtagtagcg gctgctggca ctaccctcca agaccttgtg gc                          42

<210> SEQ ID NO 59
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ggtggaattc tggcaacagg gaaccttcct gg                                     32

<210> SEQ ID NO 60
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gcaatcagtg gggcagccgc tactaccaca aggggcgct ccgcacac                     48

<210> SEQ ID NO 61
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ccgtctagat tacgcctccg cttgggatat gag                                    33

<210> SEQ ID NO 62
<211> LENGTH: 33
<212> TYPE: DNA
<213> ORGANISM: Artificial Sequence
<220> FEATURE:
```

-continued

<223> OTHER INFORMATION: Description of Artificial Sequence: Synthetic
primer

<400> SEQUENCE: 62
ggtagtagcg gctgccccac tgattgcttc cgc                33

<210> SEQ ID NO 63
<211> LENGTH: 15
<212> TYPE: PRT
<213> ORGANISM: Artificial Sequence
<220> FEATURE:
<223> OTHER INFORMATION: Description of Artificial Sequence: Synthetic
peptide

<400> SEQUENCE: 63

Met Asn Pro Leu Leu Ile Leu Thr Phe Val Ala Ala Leu Ala
1               5                   10                  15

<210> SEQ ID NO 64
<211> LENGTH: 278
<212> TYPE: PRT
<213> ORGANISM: Hepatitis C virus

<400> SEQUENCE: 64

Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
                20                  25                  30

Thr Asn Gly Ser Trp His Ile Asn Ser Thr Ala Leu Asn Cys Asn Glu
            35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
            100                 105                 110

Ile Val Pro Ala Lys Ser Val Cys Gly Pro Val Tyr Cys Phe Thr Pro
        115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
            180                 185                 190

Asn Asn Thr Leu Leu Cys Pro Thr Asp Cys Phe Arg Lys His Pro Glu
        195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
            260                 265                 270

```
Asp Arg Asp Arg Ser Glu
        275

<210> SEQ ID NO 65
<211> LENGTH: 256
<212> TYPE: PRT
<213> ORGANISM: Hepatitis C virus

<400> SEQUENCE: 65

Glu Thr His Gln Asn Ile Gln Leu Ile Asn Thr Asn Gly Ser Trp His
1               5                   10                  15

Ile Asn Ser Thr Ala Leu Asn Cys Asn Glu Ser Leu Asn Thr Gly Trp
            20                  25                  30

Leu Ala Gly Leu Phe Tyr Gln His Lys Phe Asn Ser Ser Gly Cys Pro
        35                  40                  45

Glu Arg Leu Ala Ser Cys Arg Arg Leu Thr Asp Phe Ala Gln Gly Trp
    50                  55                  60

Gly Pro Ile Ser Tyr Ala Asn Gly Ser Gly Leu Asp Glu Arg Pro Tyr
65                  70                  75                  80

Cys Trp His Tyr Pro Pro Arg Pro Cys Gly Ile Val Pro Ala Lys Ser
                85                  90                  95

Val Cys Gly Pro Val Tyr Cys Phe Thr Pro Ser Pro Val Val Val Gly
            100                 105                 110

Thr Thr Asp Arg Ser Gly Ala Pro Thr Tyr Ser Trp Gly Ala Asn Asp
        115                 120                 125

Thr Asp Val Phe Val Leu Asn Asn Thr Arg Pro Pro Leu Gly Asn Trp
    130                 135                 140

Phe Gly Cys Thr Trp Met Asn Ser Thr Gly Phe Thr Lys Val Cys Gly
145                 150                 155                 160

Ala Pro Pro Cys Val Ile Gly Gly Val Gly Asn Asn Thr Leu Leu Cys
                165                 170                 175

Pro Thr Asp Cys Phe Arg Lys His Pro Glu Ala Thr Tyr Ser Arg Cys
            180                 185                 190

Gly Ser Gly Pro Trp Ile Thr Pro Arg Cys Met Val Asp Tyr Pro Tyr
        195                 200                 205

Arg Leu Trp His Tyr Pro Cys Thr Ile Asn Tyr Thr Ile Phe Lys Val
    210                 215                 220

Arg Met Tyr Val Gly Gly Val Glu His Arg Leu Glu Ala Ala Cys Asn
225                 230                 235                 240

Trp Thr Arg Gly Glu Arg Cys Asp Leu Glu Asp Arg Asp Arg Ser Glu
                245                 250                 255

<210> SEQ ID NO 66
<211> LENGTH: 255
<212> TYPE: PRT
<213> ORGANISM: Hepatitis C virus

<400> SEQUENCE: 66

Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60
```

```
Asn Ser Ser Gly Cys Pro Glu Arg Leu Ala Ser Cys Gly Ser Ser Gly
 65                  70                  75                  80

Cys Trp His Tyr Pro Pro Arg Pro Cys Gly Ile Val Pro Ala Lys Ser
                 85                  90                  95

Val Cys Gly Pro Val Tyr Cys Phe Thr Pro Ser Pro Val Val Val Gly
            100                 105                 110

Thr Thr Asp Arg Ser Gly Ala Pro Thr Tyr Ser Trp Gly Ala Asn Asp
            115                 120                 125

Thr Asp Val Phe Val Leu Asn Asn Thr Arg Pro Pro Leu Gly Asn Trp
            130                 135                 140

Phe Gly Cys Thr Trp Met Asn Ser Thr Gly Phe Thr Lys Val Cys Gly
145                 150                 155                 160

Ala Pro Pro Cys Val Ile Gly Gly Val Gly Asn Asn Thr Leu Leu Cys
                165                 170                 175

Pro Thr Asp Cys Phe Arg Lys His Pro Glu Ala Thr Tyr Ser Arg Cys
            180                 185                 190

Gly Ser Gly Pro Trp Ile Thr Pro Arg Cys Met Val Asp Tyr Pro Tyr
            195                 200                 205

Arg Leu Trp His Tyr Pro Cys Thr Ile Asn Tyr Thr Ile Phe Lys Val
210                 215                 220

Arg Met Tyr Gly Gly Val Glu His Arg Leu Glu Ala Ala Cys Asn Trp
225                 230                 235                 240

Thr Arg Gly Glu Arg Cys Asp Leu Glu Asp Arg Asp Arg Ser Glu
            245                 250                 255

<210> SEQ ID NO 67
<211> LENGTH: 271
<212> TYPE: PRT
<213> ORGANISM: Hepatitis C virus

<400> SEQUENCE: 67

Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
 65                 70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Arg Pro Cys Gly
            100                 105                 110

Ile Val Pro Ala Lys Ser Val Cys Gly Pro Val Tyr Cys Phe Thr Pro
            115                 120                 125

Ser Pro Val Val Val Gly Thr Thr Asp Arg Ser Gly Ala Pro Thr Tyr
            130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Gly Ser Ser Gly Cys Pro
```

```
                    180                 185                 190
Thr Asp Cys Phe Arg Lys His Pro Glu Ala Thr Tyr Ser Arg Cys Gly
                195                 200                 205

Ser Gly Pro Trp Ile Thr Pro Arg Cys Met Val Asp Tyr Pro Tyr Arg
            210                 215                 220

Leu Trp His Tyr Pro Cys Thr Ile Asn Tyr Thr Ile Phe Lys Val Arg
225                 230                 235                 240

Met Tyr Val Gly Val Glu His Arg Leu Glu Ala Ala Cys Asn Trp
                245                 250                 255

Thr Arg Gly Glu Arg Cys Asp Leu Glu Asp Arg Asp Arg Ser Glu
            260                 265                 270
```

<210> SEQ ID NO 68
<211> LENGTH: 234
<212> TYPE: PRT
<213> ORGANISM: Hepatitis C virus

<400> SEQUENCE: 68

```
Glu Thr His Gln Asn Ile Gln Leu Ile Asn Thr Asn Gly Ser Trp His
1               5                   10                  15

Ile Asn Ser Thr Ala Leu Asn Cys Asn Glu Ser Leu Asn Thr Gly Trp
            20                  25                  30

Leu Ala Gly Leu Phe Tyr Gln His Lys Phe Asn Ser Ser Gly Cys Pro
        35                  40                  45

Glu Arg Leu Ala Ser Cys Gly Ser Ser Gly Cys Trp His Tyr Pro Pro
    50                  55                  60

Arg Pro Cys Gly Ile Val Pro Ala Lys Ser Val Cys Gly Pro Val Tyr
65                  70                  75                  80

Cys Phe Thr Pro Ser Pro Val Val Val Gly Thr Thr Asp Arg Ser Gly
                85                  90                  95

Ala Pro Thr Tyr Ser Trp Gly Ala Asn Asp Thr Asp Val Phe Val Leu
            100                 105                 110

Asn Asn Thr Arg Pro Pro Leu Gly Asn Trp Phe Gly Cys Thr Trp Met
        115                 120                 125

Asn Ser Thr Gly Phe Thr Lys Val Cys Gly Ala Pro Pro Cys Val Ile
    130                 135                 140

Gly Gly Val Gly Asn Asn Thr Leu Leu Cys Pro Thr Asp Cys Phe Arg
145                 150                 155                 160

Lys His Pro Glu Ala Thr Tyr Ser Arg Cys Gly Ser Gly Pro Trp Ile
                165                 170                 175

Thr Pro Arg Cys Met Val Asp Tyr Pro Tyr Arg Leu Trp His Tyr Pro
            180                 185                 190

Cys Thr Ile Asn Tyr Thr Ile Phe Lys Val Arg Met Tyr Val Gly Gly
        195                 200                 205

Val Glu His Arg Leu Glu Ala Ala Cys Asn Trp Thr Arg Gly Glu Arg
    210                 215                 220

Cys Asp Leu Glu Asp Arg Asp Arg Ser Glu
225                 230
```

<210> SEQ ID NO 69
<211> LENGTH: 249
<212> TYPE: PRT
<213> ORGANISM: Hepatitis C virus

<400> SEQUENCE: 69

```
Glu Thr His Gln Asn Ile Gln Leu Ile Asn Thr Asn Gly Ser Trp His
```

```
1               5                   10                  15
Ile Asn Ser Thr Ala Leu Asn Cys Asn Glu Ser Leu Asn Thr Gly Trp
                20                  25                  30
Leu Ala Gly Leu Phe Tyr Gln His Lys Phe Asn Ser Ser Gly Cys Pro
                35                  40                  45
Glu Arg Leu Ala Ser Cys Arg Arg Leu Thr Asp Phe Ala Gln Gly Trp
            50                  55                  60
Gly Pro Ile Ser Tyr Ala Asn Gly Ser Gly Leu Asp Glu Arg Pro Tyr
65                  70                  75                  80
Cys Trp His Tyr Pro Pro Arg Pro Cys Gly Ile Val Pro Ala Lys Ser
                85                  90                  95
Val Cys Gly Pro Val Tyr Cys Phe Thr Pro Ser Pro Val Val Val Gly
                100                 105                 110
Thr Thr Asp Arg Ser Gly Ala Pro Thr Tyr Ser Trp Gly Ala Asn Asp
                115                 120                 125
Thr Asp Val Phe Val Leu Asn Asn Thr Arg Pro Pro Leu Gly Asn Trp
                130                 135                 140
Phe Gly Cys Thr Trp Met Asn Ser Thr Gly Phe Thr Lys Val Cys Gly
145                 150                 155                 160
Ala Pro Pro Cys Gly Ser Ser Gly Cys Pro Thr Asp Cys Phe Arg Lys
                165                 170                 175
His Pro Glu Ala Thr Tyr Ser Arg Cys Gly Ser Gly Pro Trp Ile Thr
                180                 185                 190
Pro Arg Cys Met Val Asp Tyr Pro Tyr Arg Leu Trp His Tyr Pro Cys
                195                 200                 205
Thr Ile Asn Tyr Thr Ile Phe Lys Val Arg Met Tyr Val Gly Gly Val
                210                 215                 220
Glu His Arg Leu Glu Ala Ala Cys Asn Trp Thr Arg Gly Glu Arg Cys
225                 230                 235                 240
Asp Leu Glu Asp Arg Asp Arg Ser Glu
                245

<210> SEQ ID NO 70
<211> LENGTH: 249
<212> TYPE: PRT
<213> ORGANISM: Hepatitis C virus

<400> SEQUENCE: 70

Glu Thr His Val Thr Gly Gly Asn Ala Gly Arg Thr Thr Ala Gly Leu
1               5                   10                  15
Val Gly Leu Leu Thr Pro Gly Ala Lys Gln Asn Ile Gln Leu Ile Asn
                20                  25                  30
Thr Asn Gly Ser Trp His Ile Asn Ser Thr Ala Leu Asn Cys Asn Glu
                35                  40                  45
Ser Leu Asn Thr Gly Trp Leu Ala Gly Leu Phe Tyr Gln His Lys Phe
                50                  55                  60
Asn Ser Ser Gly Cys Pro Glu Arg Leu Ala Ser Cys Gly Ser Ser Gly
65                  70                  75                  80
Cys Trp His Tyr Pro Pro Arg Pro Cys Gly Ile Val Pro Ala Lys Ser
                85                  90                  95
Val Cys Gly Pro Val Tyr Cys Phe Thr Pro Ser Pro Val Val Val Gly
                100                 105                 110
Thr Thr Asp Arg Ser Gly Ala Pro Thr Tyr Ser Trp Gly Ala Asn Asp
                115                 120                 125
```

```
Thr Asp Val Phe Val Leu Asn Asn Thr Arg Pro Pro Leu Gly Asn Trp
            130                 135                 140
Phe Gly Cys Thr Trp Met Asn Ser Thr Gly Phe Thr Lys Val Cys Gly
145                 150                 155                 160
Ala Pro Pro Cys Gly Ser Ser Gly Cys Pro Thr Asp Cys Phe Arg Lys
                165                 170                 175
His Pro Glu Ala Thr Tyr Ser Arg Cys Gly Ser Gly Pro Trp Ile Thr
            180                 185                 190
Pro Arg Cys Met Trp Asp Tyr Pro Tyr Arg Leu Trp His Tyr Pro Cys
        195                 200                 205
Thr Ile Asn Tyr Thr Ile Phe Lys Val Arg Met Tyr Val Gly Gly Val
    210                 215                 220
Glu His Arg Leu Glu Ala Ala Cys Asn Trp Thr Arg Gly Glu Arg Cys
225                 230                 235                 240
Asp Leu Glu Asp Arg Asp Arg Ser Glu
            245

<210> SEQ ID NO 71
<211> LENGTH: 227
<212> TYPE: PRT
<213> ORGANISM: Hepatitis C virus

<400> SEQUENCE: 71

Glu Thr His Gln Asn Ile Gln Leu Ile Asn Thr Asn Gly Ser Trp His
1               5                   10                  15
Ile Asn Ser Thr Ala Leu Asn Cys Asn Glu Ser Leu Asn Thr Gly Trp
            20                  25                  30
Leu Ala Gly Leu Phe Tyr Gln His Lys Phe Asn Ser Ser Gly Cys Pro
        35                  40                  45
Glu Arg Leu Ala Ser Cys Gly Ser Gly Cys Trp His Tyr Pro Pro
    50                  55                  60
Arg Pro Cys Gly Ile Val Pro Ala Lys Ser Val Cys Gly Pro Val Tyr
65                  70                  75                  80
Cys Phe Thr Pro Ser Pro Val Val Gly Thr Thr Asp Arg Ser Gly
                85                  90                  95
Ala Pro Thr Tyr Ser Trp Gly Ala Asn Asp Thr Asp Val Phe Val Leu
            100                 105                 110
Asn Asn Thr Arg Pro Pro Leu Gly Asn Trp Phe Gly Cys Thr Trp Met
        115                 120                 125
Asn Ser Thr Gly Phe Thr Lys Val Cys Gly Ala Pro Pro Cys Gly Ser
    130                 135                 140
Ser Gly Cys Pro Thr Asp Cys Phe Arg Lys His Pro Glu Ala Thr Tyr
145                 150                 155                 160
Ser Arg Cys Gly Ser Gly Pro Trp Ile Thr Pro Arg Cys Met Val Asp
                165                 170                 175
Tyr Pro Tyr Arg Leu Trp His Tyr Pro Cys Thr Ile Asn Tyr Thr Ile
            180                 185                 190
Phe Lys Val Arg Met Tyr Val Gly Gly Val Glu His Arg Leu Glu Ala
        195                 200                 205
Ala Cys Asn Trp Thr Arg Gly Glu Arg Cys Asp Leu Glu Asp Arg Asp
    210                 215                 220
Arg Ser Glu
225

<210> SEQ ID NO 72
```

```
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tatagctagc gccaccatga accccctgc                                          29

<210> SEQ ID NO 73
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
ctggatgttc tggtgggtct cggccag                                            27

<210> SEQ ID NO 74
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gccgagaccc accagaacat ccagctg                                            27

<210> SEQ ID NO 75
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgctgctgcc gcaggaggcg ag                                                 22

<210> SEQ ID NO 76
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gtagtgccag cagccgctgc tgccgcagga ggcgagcctc tcggg                        45

<210> SEQ ID NO 77
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
ggcagcagcg gctgctggca ctac                                               24

<210> SEQ ID NO 78
<211> LENGTH: 44
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
ctcgcctcct gcggcagcag cggctgctgg cactaccccc caga            44

<210> SEQ ID NO 79
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
gtcggtgggg cagccgctgc tgccgcaggg aggggcgcca cacac           45

<210> SEQ ID NO 80
<211> LENGTH: 45
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
gcccctccct gcggcagcag cggctgcccc accgactgct ttagg           45

<210> SEQ ID NO 81
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
tctgctcgag ttatcagtgg tgatggtggt gg                         32

<210> SEQ ID NO 82
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ctctcgttgc agttcagggc ggtgctg                               27

<210> SEQ ID NO 83
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
cagcaccgcc ctgaactgca acgagag                               27

<210> SEQ ID NO 84
<211> LENGTH: 27
<212> TYPE: DNA
```

<213> ORGANISM: Artificial Sequence
<220> FEATURE:
<223> OTHER INFORMATION: Description of Artificial Sequence: Synthetic primer

<400> SEQUENCE: 84
caagctagcg gaacctatgt gacaggg    27

<210> SEQ ID NO 85
<211> LENGTH: 54
<212> TYPE: DNA
<213> ORGANISM: Artificial Sequence
<220> FEATURE:
<223> OTHER INFORMATION: Description of Artificial Sequence: Synthetic primer

<400> SEQUENCE: 85
ccctctagat tagtggtggt ggtggtggtg gccgccctct gatctgtccc tgtc    54

<210> SEQ ID NO 86
<211> LENGTH: 30
<212> TYPE: DNA
<213> ORGANISM: Artificial Sequence
<220> FEATURE:
<223> OTHER INFORMATION: Description of Artificial Sequence: Synthetic primer

<400> SEQUENCE: 86
caagctagcg gcaccaccac cgttggaggc    30

<210> SEQ ID NO 87
<211> LENGTH: 69
<212> TYPE: DNA
<213> ORGANISM: Artificial Sequence
<220> FEATURE:
<223> OTHER INFORMATION: Description of Artificial Sequence: Synthetic primer

<400> SEQUENCE: 87
ccgtctagac taattcagat cctcttctga gatgagtttt tgttcagtac tctgactcct    60
gtccctgtc    69

<210> SEQ ID NO 88
<211> LENGTH: 363
<212> TYPE: PRT
<213> ORGANISM: Hepatitis C virus

<400> SEQUENCE: 88

```
Glu Thr His Val Thr Gly Gly Asn Ala Gly Arg Thr Thr Ala Gly Leu
1               5                   10                  15

Val Gly Leu Leu Thr Pro Gly Ala Lys Gln Asn Ile Gln Leu Ile Asn
            20                  25                  30

Thr Asn Gly Ser Trp His Ile Asn Ser Thr Ala Leu Asn Cys Asn Glu
        35                  40                  45

Ser Leu Asn Thr Gly Trp Leu Ala Gly Leu Phe Tyr Gln His Lys Phe
    50                  55                  60

Asn Ser Ser Gly Cys Pro Glu Arg Leu Ala Ser Cys Arg Arg Leu Thr
65                  70                  75                  80

Asp Phe Ala Gln Gly Trp Gly Pro Ile Ser Tyr Ala Asn Gly Ser Gly
                85                  90                  95

Leu Asp Glu Arg Pro Tyr Cys Trp His Tyr Pro Pro Arg Pro Cys Gly
                100                 105                 110
```

Ile Val Pro Ala Lys Ser Val Cys Gly Pro Val Tyr Cys Phe Thr Pro
                115                 120                 125

Ser Pro Val Val Val Gly Thr Thr Asp Arg Ser Gly Ala Pro Thr Tyr
    130                 135                 140

Ser Trp Gly Ala Asn Asp Thr Asp Val Phe Val Leu Asn Asn Thr Arg
145                 150                 155                 160

Pro Pro Leu Gly Asn Trp Phe Gly Cys Thr Trp Met Asn Ser Thr Gly
                165                 170                 175

Phe Thr Lys Val Cys Gly Ala Pro Pro Cys Val Ile Gly Gly Val Gly
                180                 185                 190

Asn Asn Thr Leu Leu Cys Pro Thr Asp Cys Phe Arg Lys His Pro Glu
                195                 200                 205

Ala Thr Tyr Ser Arg Cys Gly Ser Gly Pro Trp Ile Thr Pro Arg Cys
    210                 215                 220

Met Val Asp Tyr Pro Tyr Arg Leu Trp His Tyr Pro Cys Thr Ile Asn
225                 230                 235                 240

Tyr Thr Ile Phe Lys Val Arg Met Tyr Val Gly Gly Val Glu His Arg
                245                 250                 255

Leu Glu Ala Ala Cys Asn Trp Thr Arg Gly Glu Arg Cys Asp Leu Glu
                260                 265                 270

Asp Arg Asp Arg Ser Glu Leu Ser Pro Leu Leu Leu Ser Thr Thr Gln
    275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Val Gly Ser Ser Ile Ala Ser Trp Ala Ile Lys Trp Glu Tyr Val
                325                 330                 335

Val Leu Leu Phe Leu Leu Leu Ala Asp Ala Arg Val Cys Ser Cys Leu
                340                 345                 350

Trp Met Met Leu Leu Ile Ser Gln Ala Glu Ala
                355                 360

<210> SEQ ID NO 89
<211> LENGTH: 363
<212> TYPE: PRT
<213> ORGANISM: Hepatitis C virus

<400> SEQUENCE: 89

His Thr Leu Thr Thr Gly Gly His Ala Ala His Leu Thr Ser Gly Phe
1               5                   10                  15

Ala Gly Leu Phe Thr Pro Gly Pro Ser Gln Arg Ile Gln Leu Ile Asn
                20                  25                  30

Thr Asn Gly Ser Trp His Ile Asn Arg Thr Ala Leu Asn Cys Asn Asp
                35                  40                  45

Ser Leu Gln Thr Gly Phe Leu Ala Ala Leu Ser Tyr Thr Tyr Arg Phe
    50                  55                  60

Asn Ser Ser Gly Cys Pro Gly Arg Met Ala Ser Cys Arg Ser Ile Asp
65                  70                  75                  80

Lys Phe Asp Gln Gly Trp Gly Pro Ile Thr Tyr Ala Asp Pro Lys Asp
                85                  90                  95

Pro Asp Gln Arg Pro Tyr Cys Trp His Tyr Ala Pro Gln Gln Cys Gly
                100                 105                 110

Ile Ile Pro Arg Ser Glu Ala Cys Gly Pro Val Tyr Cys Ser Thr Pro
                115                 120                 125

-continued

Ser Pro Val Val Gly Thr Thr Asp Arg Phe Gly Ala Pro Thr Tyr
    130                 135                 140

Asn Trp Gly Asp Asn Glu Thr Asp Val Leu Leu Asn Asn Thr Arg
145                 150                 155                 160

Pro Pro Gln Gly Asn Trp Phe Gly Cys Thr Trp Met Asn Ser Thr Gly
                165                 170                 175

Phe Thr Lys Thr Cys Gly Ala Pro Pro Cys Asn Ile Gly Val Gly
            180                 185                 190

Asn Asn Thr Leu Thr Cys Pro Thr Asp Cys Phe Arg Lys His Pro Glu
        195                 200                 205

Ala Thr Tyr Ser Lys Cys Gly Ser Gly Pro Trp Leu Thr Pro Arg Cys
    210                 215                 220

Met Val Asp Tyr Pro Tyr Arg Leu Trp His Tyr Pro Cys Thr Val Asn
225                 230                 235                 240

Phe Ser Ile Phe Lys Val Arg Met Tyr Val Gly Gly Val Glu His Arg
                245                 250                 255

Leu Asn Ala Ala Cys Asn Trp Thr Arg Gly Glu Arg Cys Asp Leu Asp
            260                 265                 270

Asp Arg Asp Arg Ser Glu Leu Ser Pro Leu Leu Leu Ser Thr Thr Glu
        275                 280                 285

Trp Gln Val Leu Pro Cys Ser Phe Thr Thr Leu Pro Ala Leu Ser Thr
    290                 295                 300

Gly Leu Ile His Leu His Gln Asn Ile Val Asp Val Gln Tyr Leu Tyr
305                 310                 315                 320

Gly Ile Gly Ser Ala Val Val Ser Phe Ala Ile Lys Trp Glu Tyr Val
                325                 330                 335

Val Leu Leu Phe Leu Leu Leu Ala Asp Ala Arg Val Cys Ala Cys Leu
            340                 345                 350

Trp Met Met Leu Leu Ile Ala Arg Ala Glu Ala
        355                 360

<210> SEQ ID NO 90
<211> LENGTH: 363
<212> TYPE: PRT
<213> ORGANISM: Hepatitis C virus

<400> SEQUENCE: 90

Glu Thr His Val Ser Gly Ala Ala Val Gly Arg Ser Thr Ala Gly Leu
1               5                   10                  15

Ala Asn Leu Phe Ser Ser Gly Ser Lys Gln Asn Leu Gln Leu Ile Asn
                20                  25                  30

Ser Asn Gly Ser Trp His Ile Asn Arg Thr Ala Leu Asn Cys Asn Asp
            35                  40                  45

Ser Leu Asn Thr Gly Phe Leu Ala Ser Leu Phe Tyr Thr His Lys Phe
    50                  55                  60

Asn Ser Ser Gly Cys Ser Glu Arg Leu Ala Cys Cys Lys Ser Leu Asp
65                  70                  75                  80

Ser Tyr Gly Gln Gly Trp Gly Pro Leu Gly Val Ala Asn Ile Ser Gly
                85                  90                  95

Ser Ser Asp Asp Arg Pro Tyr Cys Trp His Tyr Ala Pro Arg Pro Cys
            100                 105                 110

Gly Ile Val Pro Ala Ser Ser Val Cys Gly Pro Val Tyr Cys Phe Thr
    115                 120                 125

Pro Ser Pro Val Val Val Gly Thr Thr Asp His Val Gly Val Pro Thr

```
                130                 135                 140
Tyr Thr Trp Gly Glu Asn Glu Thr Asp Val Phe Leu Leu Asn Ser Thr
145                 150                 155                 160

Arg Pro Pro His Gly Ala Trp Phe Gly Cys Val Trp Met Asn Ser Thr
                165                 170                 175

Gly Phe Thr Lys Thr Cys Gly Ala Pro Pro Cys Glu Val Asn Thr Asn
                180                 185                 190

Asn Gly Thr Trp His Cys Pro Thr Asp Cys Phe Arg Lys His Pro Glu
                195                 200                 205

Thr Thr Tyr Ala Lys Cys Gly Ser Gly Pro Trp Ile Thr Pro Arg Cys
                210                 215                 220

Leu Ile Asp Tyr Pro Tyr Arg Leu Trp His Phe Pro Cys Thr Ala Asn
225                 230                 235                 240

Phe Ser Val Phe Asn Ile Arg Thr Phe Val Gly Gly Ile Glu His Arg
                245                 250                 255

Met Gln Ala Ala Cys Asn Trp Thr Arg Gly Glu Val Cys Gly Leu Glu
                260                 265                 270

His Arg Asp Arg Val Glu Leu Ser Pro Leu Leu Leu Thr Thr Thr Ala
                275                 280                 285

Trp Gln Ile Leu Pro Cys Ser Phe Thr Thr Leu Pro Ala Leu Ser Thr
                290                 295                 300

Gly Leu Ile His Leu His Gln Asn Ile Val Asp Val Gln Tyr Leu Tyr
305                 310                 315                 320

Gly Val Gly Ser Ala Val Val Ser Trp Ala Leu Lys Trp Glu Tyr Val
                325                 330                 335

Val Leu Ala Phe Leu Leu Leu Ala Asp Ala Arg Val Ser Ala Tyr Leu
                340                 345                 350

Trp Met Met Phe Met Val Ser Gln Val Glu Ala
                355                 360

<210> SEQ ID NO 91
<211> LENGTH: 367
<212> TYPE: PRT
<213> ORGANISM: Hepatitis C virus

<400> SEQUENCE: 91

Gln Thr Met Ile Ala His Gly Val Ser Gln Thr Thr Ser Gly Phe Ala
1               5                   10                  15

Ser Leu Leu Thr Pro Gly Ala Lys Gln Asn Ile Gln Leu Ile Asn Thr
                20                  25                  30

Asn Gly Ser Trp His Ile Asn Arg Thr Ala Leu Asn Cys Asn Asp Ser
                35                  40                  45

Leu Gln Thr Gly Phe Leu Ala Ser Leu Phe Tyr Thr His Lys Phe Asn
                50                  55                  60

Ser Ser Gly Cys Pro Glu Arg Met Ala Ala Cys Lys Pro Leu Ala Glu
65                  70                  75                  80

Phe Arg Gln Gly Trp Gly Gln Ile Thr His Lys Asn Val Ser Gly Pro
                85                  90                  95

Ser Asp Asp Arg Pro Tyr Cys Trp His Tyr Ala Pro Arg Pro Cys Glu
                100                 105                 110

Val Val Pro Ala Arg Ser Val Cys Gly Pro Val Tyr Cys Phe Thr Pro
                115                 120                 125

Ser Pro Val Val Val Gly Thr Thr Asp Lys Arg Gly Asn Pro Thr Tyr
                130                 135                 140
```

```
Thr Trp Gly Glu Asn Glu Thr Asp Val Phe Met Leu Glu Ser Leu Arg
145                 150                 155                 160

Pro Pro Thr Gly Gly Trp Phe Gly Cys Thr Trp Met Asn Ser Thr Gly
                165                 170                 175

Phe Thr Lys Thr Cys Gly Ala Pro Pro Cys Gln Ile Val Pro Gly Asn
            180                 185                 190

Tyr Asn Ser Ser Ala Asn Glu Leu Leu Cys Pro Thr Asp Cys Phe Arg
        195                 200                 205

Lys His Pro Glu Ala Thr Tyr Gln Arg Cys Gly Ser Gly Pro Trp Val
    210                 215                 220

Thr Pro Arg Cys Leu Val Asp Tyr Ala Tyr Arg Leu Trp His Tyr Pro
225                 230                 235                 240

Cys Thr Val Asn Phe Thr Leu His Lys Val Arg Met Phe Val Gly Gly
                245                 250                 255

Thr Glu His Arg Phe Asp Val Ala Cys Asn Trp Thr Arg Gly Glu Arg
            260                 265                 270

Cys Glu Leu His Asp Arg Asn Arg Ile Glu Met Ser Pro Leu Leu Phe
        275                 280                 285

Ser Thr Thr Gln Leu Ser Ile Leu Pro Cys Ser Phe Ser Thr Met Pro
    290                 295                 300

Ala Leu Ser Thr Gly Leu Ile His Leu His Gln Asn Ile Val Asp Val
305                 310                 315                 320

Gln Tyr Leu Tyr Gly Val Ser Thr Asn Val Thr Ser Trp Val Val Lys
                325                 330                 335

Trp Glu Tyr Ile Val Leu Met Phe Leu Val Leu Ala Asp Ala Arg Ile
            340                 345                 350

Cys Thr Cys Leu Trp Leu Met Leu Leu Ile Ser Thr Val Glu Ala
        355                 360                 365

<210> SEQ ID NO 92
<211> LENGTH: 368
<212> TYPE: PRT
<213> ORGANISM: Hepatitis C virus

<400> SEQUENCE: 92

Val Thr Tyr Thr Thr Gly Gly Ser Ala Ala His Ala Thr Arg Gly Leu
1               5                   10                  15

Thr Ser Leu Phe Ser Val Gly Ala Gln Gln Lys Leu Gln Leu Val Asn
                20                  25                  30

Thr Asn Gly Ser Trp His Ile Asn Ser Thr Ala Leu Asn Cys Asn Glu
            35                  40                  45

Ser Ile Asn Thr Gly Phe Ile Ala Gly Leu Phe Tyr Tyr His Arg Phe
50                  55                  60

Asn Ser Thr Gly Cys Pro Gln Arg Leu Ser Ser Cys Lys Pro Ile Thr
65                  70                  75                  80

Phe Phe Lys Gln Gly Trp Gly Pro Leu Thr Asp Ala Asn Ile Ser Gly
                85                  90                  95

Pro Ser Asp Asp Lys Pro Tyr Cys Trp His Tyr Ala Pro Arg Pro Lys
            100                 105                 110

Val Val Pro Ala Ser Gly Val Cys Gly Pro Val Tyr Cys Phe Thr Pro
        115                 120                 125

Ser Pro Val Val Val Gly Thr Thr Asp Ala Lys Gly Val Pro Thr Tyr
    130                 135                 140

Thr Trp Gly Ala Asn Asp Thr Asp Val Phe Leu Leu Glu Ser Leu Arg
145                 150                 155                 160
```

```
Pro Pro Gly Gly Arg Trp Phe Gly Cys Thr Trp Met Asn Ser Thr Gly
                165                 170                 175

Phe Val Lys Thr Cys Gly Ala Ser Pro Cys Asp Ile Tyr Gly Gly Gly
            180                 185                 190

Gly Asn Ser Gly Asn Glu Ser Asp Leu Phe Cys Pro Thr Asp Cys Phe
        195                 200                 205

Arg Lys His Pro Glu Ala Thr Tyr Ser Arg Cys Gly Ala Gly Pro Trp
    210                 215                 220

Leu Thr Pro Arg Cys Met Val Asp Tyr Pro Tyr Arg Leu Trp His Tyr
225                 230                 235                 240

Pro Cys Thr Val Asn Phe Thr Leu Phe Lys Val Arg Met Phe Val Gly
                245                 250                 255

Gly Phe Glu His Arg Phe Thr Ala Ala Cys Asn Trp Thr Arg Gly Glu
            260                 265                 270

Arg Cys Asp Ile Glu Asp Arg Asp Arg Ser Glu Gln His Pro Leu Leu
        275                 280                 285

His Ser Thr Thr Glu Leu Ala Ile Leu Pro Cys Ser Phe Thr Pro Met
    290                 295                 300

Pro Ala Leu Ser Thr Gly Leu Ile His Leu His Gln Asn Ile Val Asp
305                 310                 315                 320

Val Gln Tyr Leu Tyr Gly Val Gly Ser Gly Met Val Gly Trp Ala Leu
                325                 330                 335

Lys Trp Glu Phe Val Ile Leu Ile Phe Leu Leu Leu Ala Asp Arg Arg
            340                 345                 350

Val Cys Val Ala Leu Trp Leu Met Leu Met Ile Thr Gln Ala Glu Ala
        355                 360                 365

<210> SEQ ID NO 93
<211> LENGTH: 363
<212> TYPE: PRT
<213> ORGANISM: Hepatitis C virus

<400> SEQUENCE: 93

Asn Thr Arg Thr Val Gly Gly Ser Ala Ala Gln Gly Ala Arg Gly Leu
1               5                   10                  15

Ala Ser Leu Phe Thr Pro Gly Pro Gln Gln Asn Leu Gln Leu Ile Asn
            20                  25                  30

Thr Asn Gly Ser Trp His Ile Asn Arg Thr Ala Leu Asn Cys Asn Asp
        35                  40                  45

Ser Leu Gln Thr Gly Phe Val Ala Gly Leu Leu Tyr Tyr His Lys Phe
    50                  55                  60

Asn Ser Thr Gly Cys Pro Gln Arg Met Ala Ser Cys Arg Pro Leu Ala
65                  70                  75                  80

Ala Phe Asp Gln Gly Trp Gly Thr Ile Ser Tyr Ala Ala Val Ser Gly
            85                  90                  95

Pro Ser Asp Asp Lys Pro Tyr Cys Trp His Tyr Pro Arg Pro Cys
                100                 105                 110

Gly Ile Val Pro Ala Arg Gly Val Cys Gly Pro Val Tyr Cys Phe Thr
            115                 120                 125

Pro Ser Pro Val Val Val Gly Thr Thr Asp Arg Lys Gly Asn Pro Thr
        130                 135                 140

Tyr Ser Trp Gly Glu Asn Glu Thr Asp Ile Phe Leu Leu Asn Asn Thr
145                 150                 155                 160

Arg Pro Pro Thr Gly Asn Trp Phe Gly Cys Thr Trp Met Asn Ser Thr
```

```
            165                 170                 175
Gly Phe Val Lys Thr Cys Gly Ala Pro Cys Asn Gly Pro Thr Gly
            180                 185                 190

Asn Asn Ser Leu Lys Cys Pro Thr Asp Cys Phe Arg Lys His Pro Asp
            195                 200                 205

Ala Thr Tyr Thr Lys Cys Gly Ser Gly Pro Trp Leu Thr Pro Arg Cys
            210                 215                 220

Leu Val His Tyr Pro Tyr Arg Leu Trp His Tyr Pro Cys Thr Leu Asn
225                 230                 235                 240

Tyr Thr Ile Phe Lys Val Arg Met Tyr Ile Gly Gly Leu Glu His Arg
            245                 250                 255

Leu Glu Val Ala Cys Asn Trp Thr Arg Gly Glu Arg Cys Asp Leu Glu
            260                 265                 270

Asp Arg Asp Arg Ala Glu Leu Ser Pro Leu Leu His Thr Thr Thr Gln
            275                 280                 285

Trp Ala Ile Leu Pro Cys Ser Phe Thr Pro Thr Pro Ala Leu Ser Thr
            290                 295                 300

Gly Leu Ile His Leu His Gln Asn Ile Val Asp Thr Gln Tyr Leu Tyr
305                 310                 315                 320

Gly Leu Ser Ser Ser Ile Val Ser Trp Ala Val Lys Trp Glu Tyr Ile
                325                 330                 335

Val Leu Ala Phe Leu Leu Leu Ala Asp Ala Arg Ile Cys Thr Cys Leu
            340                 345                 350

Trp Ile Met Leu Leu Val Cys Gln Ala Glu Ala
            355                 360

<210> SEQ ID NO 94
<211> LENGTH: 367
<212> TYPE: PRT
<213> ORGANISM: Hepatitis C virus

<400> SEQUENCE: 94

Gly Thr Thr Thr Val Gly Gly Ala Val Ala Arg Ser Thr Asn Val Ile
1               5                   10                  15

Ala Gly Val Phe Ser His Gly Pro Gln Gln Asn Ile Gln Leu Ile Asn
            20                  25                  30

Thr Asn Gly Ser Trp His Ile Asn Arg Thr Ala Leu Asn Cys Asn Asp
        35                  40                  45

Ser Leu Asn Thr Gly Phe Leu Ala Ala Leu Phe Tyr Thr Asn Arg Phe
    50                  55                  60

Asn Ser Ser Gly Cys Pro Gly Arg Leu Ser Ala Cys Arg Asn Ile Glu
65                  70                  75                  80

Ala Phe Arg Ile Gly Trp Gly Thr Leu Gln Tyr Glu Asp Asn Val Thr
                85                  90                  95

Asn Pro Glu Asp Met Arg Pro Tyr Cys Trp His Tyr Pro Pro Lys Pro
            100                 105                 110

Cys Gly Val Val Pro Ala Arg Ser Val Cys Gly Pro Val Tyr Cys Phe
            115                 120                 125

Thr Pro Ser Pro Val Val Val Gly Thr Thr Asp Arg Arg Gly Val Pro
            130                 135                 140

Thr Tyr Thr Trp Gly Glu Asn Glu Thr Asp Val Phe Leu Leu Asn Ser
145                 150                 155                 160

Thr Arg Pro Pro Gln Gly Ser Trp Phe Gly Cys Thr Trp Met Asn Ser
                165                 170                 175
```

```
Thr Gly Phe Thr Lys Thr Cys Gly Ala Pro Pro Cys Arg Thr Arg Ala
            180                 185                 190

Asp Phe Asn Ala Ser Thr Asp Leu Leu Cys Pro Thr Asp Cys Phe Arg
        195                 200                 205

Lys His Pro Asp Ala Thr Tyr Ile Lys Cys Gly Ser Gly Pro Trp Leu
    210                 215                 220

Thr Pro Lys Cys Leu Val His Tyr Pro Tyr Arg Leu Trp His Tyr Pro
225                 230                 235                 240

Cys Thr Val Asn Phe Thr Ile Phe Lys Ile Arg Met Tyr Val Gly Gly
                245                 250                 255

Val Glu His Arg Leu Thr Ala Ala Cys Asn Phe Thr Arg Gly Asp Arg
            260                 265                 270

Cys Asp Leu Glu Asp Arg Asp Arg Ser Gln Leu Ser Pro Leu Leu His
        275                 280                 285

Ser Thr Thr Glu Trp Ala Ile Leu Pro Cys Thr Tyr Ser Asp Leu Pro
    290                 295                 300

Ala Leu Ser Thr Gly Leu Leu His Leu His Gln Asn Ile Val Asp Val
305                 310                 315                 320

Gln Tyr Met Tyr Gly Leu Ser Pro Ala Ile Thr Lys Tyr Val Val Arg
                325                 330                 335

Trp Glu Trp Val Val Leu Leu Phe Leu Leu Leu Ala Asp Ala Arg Val
            340                 345                 350

Cys Ala Cys Leu Trp Met Leu Ile Leu Leu Gly Gln Ala Glu Ala
        355                 360                 365

<210> SEQ ID NO 95
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 95

Gly Ser Ser Gly
1

<210> SEQ ID NO 96
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 96

Gly Gly Ala Gly Gly
1               5

<210> SEQ ID NO 97
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 97

Gly Gly Gly Gly Gly
1               5
```

```
<210> SEQ ID NO 98
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 98

Gly Gly Gly Gly Gly Gly Gly Gly
1               5

<210> SEQ ID NO 99
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 99

Gly Gly Gly Gly Gly Gly
1               5

<210> SEQ ID NO 100
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 100

Gly Gly Gly Gly Gly Gly Gly
1               5

<210> SEQ ID NO 101
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 101

Gly Gly Gly Gly Gly Gly Gly Gly Gly Gly
1               5                   10

<210> SEQ ID NO 102
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 102

Gly Ser Gly Ser Gly
1               5

<210> SEQ ID NO 103
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 103
```

```
Gly Gly Gly Gly
1

<210> SEQ ID NO 104
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 104

Gly Gly Arg Gly Gly Ser
1               5

<210> SEQ ID NO 105
<211> LENGTH: 20
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (1)..(20)
<223> OTHER INFORMATION: This sequence may encompass 3-4 'GGGGS'
      repeating units

<400> SEQUENCE: 105

Gly Gly Gly Gly Ser Gly Gly Gly Ser Gly Gly Gly Gly Ser Gly
1               5                   10                  15

Gly Gly Gly Ser
            20

<210> SEQ ID NO 106
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 106

Ser Gly Gly Ser Gly
1               5

<210> SEQ ID NO 107
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 107

Gly Trp Leu Ala Gly Leu Phe Tyr
1               5

<210> SEQ ID NO 108
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 108
```

His His His His His His
1               5

<210> SEQ ID NO 109
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 109

Glu Thr His Gly Ser Ser Gly
1               5

<210> SEQ ID NO 110
<211> LENGTH: 46
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 110

Glu Thr His Val Thr Gly Gly Ser Ala Gly Arg Thr Thr Ala Gly Leu
1               5                   10                  15

Val Gly Leu Leu Thr Pro Gly Ala Arg Gln Asn Ile Gln Leu Ile Asn
            20                  25                  30

Thr Asn Gly Ser Trp His Ile Asn Ser Thr Ala Leu Asn Cys
        35                  40                  45

<210> SEQ ID NO 111
<211> LENGTH: 28
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 111

Cys Arg Arg Leu Thr Asp Phe Ala Gln Gly Trp Gly Pro Ile Ser Tyr
1               5                   10                  15

Ala Asn Gly Ser Gly Leu Asp Glu Arg Pro Tyr Cys
            20                  25

<210> SEQ ID NO 112
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Cys Val Ile Gly Gly Val Gly Asn Asn Thr Leu Leu Cys
1               5                   10

<210> SEQ ID NO 113
<211> LENGTH: 27
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 113

```
gttctggccg ctactacctc atcgccg                                    27

<210> SEQ ID NO 114
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 114
ggtagtagcg gccagaacat cc                                         22

<210> SEQ ID NO 115
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 115
ccatcatcgc cg                                                    12

<210> SEQ ID NO 116
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Glu Thr His Gly Ser Ser Gly Thr Ala Leu Asn
1               5                   10

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Arg Arg Leu Gly Ser Ser Gly Pro Tyr
1               5

<210> SEQ ID NO 118
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Val Ile Gly Ser Ser Gly Leu Leu
1               5
```